(12) United States Patent
Einav et al.

(10) Patent No.: US 8,938,289 B2
(45) Date of Patent: Jan. 20, 2015

(54) MOTOR TRAINING WITH BRAIN PLASTICITY

(75) Inventors: Omer Einav, Kfar-Monash (IL); Ernesto Korenman, RaAnana (IL); Samuel Faran, Mitzpe Aviv (IL); Richard M. Mahoney, Westmont, NJ (US)

(73) Assignee: Motorika Limited, Hamilton (BM)

( * ) Notice: Subject to any disclaimer, the term of this patent is extended or adjusted under 35 U.S.C. 154(b) by 1428 days.

(21) Appl. No.: 11/660,965

(22) PCT Filed: Aug. 18, 2005

(86) PCT No.: PCT/IL2005/000906
§ 371 (c)(1),
(2), (4) Date: Jan. 8, 2009

(87) PCT Pub. No.: WO2006/021952
PCT Pub. Date: Mar. 2, 2006

(65) Prior Publication Data
US 2009/0221928 A1    Sep. 3, 2009

Related U.S. Application Data

(63) Continuation-in-part of application No. PCT/IL2005/000442, filed on Apr. 28, 2005, and a continuation-in-part of application No. PCT/IL2005/000135, filed on Feb. 4, 2005, and a continuation-in-part of application No. PCT/IL2005/000136, filed on Feb. 4, 2005, and a continuation-in-part of application No. PCT/IL2005/000137, filed on Feb. 4, 2005, and a continuation-in-part of application No. PCT/IL2005/000138, filed on Feb. 4, 2005, and a continuation-in-part of application No. PCT/IL2005/000139, filed on Feb. 4, 2005, and a continuation-in-part of application No. PCT/IL2005/000142, filed on Feb. 4, 2005.

(60) Provisional application No. 60/604,615, filed on Aug. 25, 2004, provisional application No. 60/633,428, filed on Dec. 7, 2004, provisional application No. 60/633,429, filed on Dec. 7, 2004, provisional application No. 60/633,442, filed on Dec. 7, 2004, provisional application No. 60/686,991, filed on Jun. 2, 2005.

(51) Int. Cl.
*A61B 5/0484* (2006.01)

(52) U.S. Cl.
USPC .............................................. 600/544; 601/5

(58) Field of Classification Search
None
See application file for complete search history.

(56) References Cited

U.S. PATENT DOCUMENTS

| | | |
|---|---|---|
| 3,745,990 A | 7/1973 | Neis |
| 3,824,991 A | 7/1974 | Whitaker |
| 3,919,691 A | 11/1975 | Noll |
| 3,929,462 A | 12/1975 | Karmin |
| 4,099,697 A | 7/1978 | Von Schuckmann |
| 4,499,900 A | 2/1985 | Petrofsky et al. |
| 4,582,049 A | 4/1986 | Ylvisaker |
| 4,685,928 A | 8/1987 | Yaeger |
| 4,691,694 A | 9/1987 | Boyd et al. |
| 4,724,842 A | 2/1988 | Charters et al. |
| 4,765,610 A | 8/1988 | Sidwell |
| 4,773,398 A | 9/1988 | Tatom |
| 4,824,104 A | 4/1989 | Bloch |
| 4,883,067 A | 11/1989 | Knispel et al. |
| 4,921,244 A | 5/1990 | Berroth |
| 4,936,299 A | 6/1990 | Erlandson |
| 4,966,413 A | 10/1990 | Palarski |
| 5,048,826 A | 9/1991 | Ryan |
| 5,070,873 A | 12/1991 | Graupe et al. |
| 5,158,074 A | 10/1992 | Grellas |
| 5,179,939 A | 1/1993 | Donovan et al. |
| 5,193,539 A | 3/1993 | Schulman et al. |
| 5,193,540 A | 3/1993 | Schulman et al. |
| 5,201,772 A | 4/1993 | Maxwell |
| 5,211,161 A | 5/1993 | Stef |
| 5,231,998 A | 8/1993 | Rosen et al. |
| 5,244,441 A | 9/1993 | Dempster et al. |
| 5,269,318 A | 12/1993 | Nashner |
| 5,282,460 A | 2/1994 | Boldt |
| 5,311,880 A | 5/1994 | Lancaster et al. |
| 5,312,439 A | 5/1994 | Loëb |
| 5,324,316 A | 6/1994 | Schulman et al. |
| 5,343,856 A | 9/1994 | Proctor |

(Continued)

FOREIGN PATENT DOCUMENTS

| | | |
|---|---|---|
| DE | 10133572 | 4/2002 |
| EP | 0304538 | 1/1989 |

(Continued)

OTHER PUBLICATIONS

Yoo et al (Clinical Neuroscience and Neuropathology, Jul. 2004, 15:1591-1595).*
Weiskopf et al (IEEE Transcations on Biomedical Engineering, Jun. 2004, 51:966-970).*
Harwin et al (Robotica, 1998, 16:523-530).*
Translation of Notification of Reasons for Rejection Dated Dec. 15, 2010 From the Japanese Patent Office Re. Application No. 2009-027772.

(Continued)

*Primary Examiner* — Laura B Goddard

(57) ABSTRACT

A rehabilitation device, comprising a movement element capable of controlling at least one motion parameter of a portion of a patient; a brain monitor which generates a signal indicative of brain activity; and circuitry including a memory having stored therein rehabilitation information and which inter-relates said signal and movement of said movement element as part of a rehabilitation process which utilizes said rehabilitation information.

57 Claims, 12 Drawing Sheets

(56) References Cited

U.S. PATENT DOCUMENTS

| | | | |
|---|---|---|---|
| 5,358,251 A | 10/1994 | Ashton |
| 5,391,128 A | 2/1995 | DeBaer |
| 5,397,865 A | 3/1995 | Park |
| 5,405,367 A | 4/1995 | Schulman et al. |
| 5,411,044 A | 5/1995 | Andolfi |
| 5,413,611 A | 5/1995 | Haslam, II et al. |
| 5,454,774 A | 10/1995 | Davis |
| 5,466,213 A | 11/1995 | Hogan et al. |
| 5,476,103 A | 12/1995 | Nahsner |
| 5,476,428 A | 12/1995 | Potash et al. |
| 5,616,104 A | 4/1997 | Mulenburg et al. |
| 5,662,693 A | 9/1997 | Johnson et al. |
| 5,690,389 A | 11/1997 | Ekman et al. |
| 5,755,645 A | 5/1998 | Miller et al. |
| 5,830,160 A | 11/1998 | Reinkensmeyer |
| 5,836,304 A | 11/1998 | Kellinger et al. |
| 5,846,086 A | 12/1998 | Bizzi et al. |
| 5,853,353 A | 12/1998 | Blümel |
| 5,919,115 A | 7/1999 | Horowitz et al. |
| 5,954,621 A | 9/1999 | Joutras et al. |
| 5,980,435 A | 11/1999 | Joutras et al. |
| 6,004,244 A | 12/1999 | Simonson |
| 6,035,465 A | 3/2000 | Rogozinski |
| 6,051,017 A | 4/2000 | Loeb et al. |
| 6,057,828 A | 5/2000 | Rosenberg et al. |
| 6,061,004 A | 5/2000 | Rosenberg et al. |
| 6,064,912 A | 5/2000 | Kenney |
| 6,246,200 B1 | 6/2001 | Blumenkranz et al. |
| 6,270,445 B1 * | 8/2001 | Dean et al. | 482/4 |
| 6,354,945 B1 | 3/2002 | Furuki et al. |
| 6,379,393 B1 | 4/2002 | Mavroidis et al. |
| 6,478,721 B1 | 11/2002 | Hunter |
| 6,558,304 B1 | 5/2003 | Bardon et al. |
| 6,592,315 B2 | 7/2003 | Osborne, Jr. |
| 6,613,000 B1 | 9/2003 | Reinkensmeyer et al. |
| 6,645,126 B1 | 11/2003 | Martin et al. |
| 6,682,351 B1 | 1/2004 | Abraham-Fuchs et al. |
| 6,774,885 B1 | 8/2004 | Even-Zohar |
| 6,829,510 B2 | 12/2004 | Nathan et al. |
| 6,839,594 B2 | 1/2005 | Cohen et al. |
| 6,852,086 B2 | 2/2005 | Atlas et al. |
| 6,870,438 B1 | 3/2005 | Shino et al. |
| 6,966,882 B2 | 11/2005 | Horst |
| 7,115,078 B1 | 10/2006 | Kalember et al. |
| 7,163,488 B2 | 1/2007 | Anders et al. |
| 7,209,788 B2 * | 4/2007 | Nicolelis et al. | 607/48 |
| 7,381,192 B2 | 6/2008 | Brodard et al. |
| 7,504,577 B2 | 3/2009 | Riopelle |
| 8,012,107 B2 | 9/2011 | Einav et al. |
| 2002/0064438 A1 | 5/2002 | Osborne, Jr. |
| 2002/0094913 A1 | 7/2002 | Valentino |
| 2003/0032524 A1 | 2/2003 | Lamar et al. |
| 2003/0199370 A1 | 10/2003 | Bucay-Bissu |
| 2003/0208109 A1 | 11/2003 | David et al. |
| 2003/0208246 A1 | 11/2003 | Kotlik et al. |
| 2004/0102723 A1 | 5/2004 | Horst |
| 2004/0106881 A1 | 6/2004 | McBean et al. |
| 2004/0172097 A1 | 9/2004 | Brodard et al. |
| 2004/0180768 A1 | 9/2004 | Almada |
| 2004/0245838 A1 | 12/2004 | Chiu |
| 2005/0261114 A1 | 11/2005 | Heitzman et al. |
| 2006/0149338 A1 | 7/2006 | Flaherty et al. |
| 2006/0167564 A1 | 7/2006 | Flaherty et al. |
| 2006/0229164 A1 | 10/2006 | Einav |
| 2006/0277074 A1 | 12/2006 | Einav et al. |
| 2006/0293617 A1 | 12/2006 | Einav et al. |
| 2007/0282228 A1 | 12/2007 | Einav et al. |
| 2007/0299371 A1 | 12/2007 | Einav et al. |
| 2008/0132383 A1 | 6/2008 | Einav et al. |
| 2008/0161733 A1 | 7/2008 | Einav et al. |

FOREIGN PATENT DOCUMENTS

| | | |
|---|---|---|
| EP | 0569489 | 11/1993 |
| EP | 0703752 | 4/1996 |
| EP | 0862930 | 9/1998 |
| EP | 1145682 | 10/2001 |
| EP | 1364636 | 11/2003 |
| FR | 2809615 | 12/2001 |
| GB | 2357848 | 7/2011 |
| JP | 59-160455 | 9/1984 |
| JP | 60-200312 | 10/1985 |
| JP | 61-071984 | 4/1986 |
| JP | 61-217174 | 9/1986 |
| JP | 61-265151 | 11/1986 |
| JP | 01-316815 | 12/1989 |
| JP | 02-102652 | 4/1990 |
| JP | 05-007608 | 1/1993 |
| JP | 05-026209 | 4/1993 |
| JP | 06-505407 | 6/1994 |
| JP | 07-163626 | 6/1995 |
| JP | 08-322189 | 12/1996 |
| JP | 08-511448 | 12/1996 |
| JP | 03-039345 | 4/1997 |
| JP | 09-173499 | 7/1997 |
| JP | 3044600 | 10/1997 |
| JP | 3048540 | 2/1998 |
| JP | 10-207624 | 8/1998 |
| JP | 11-009574 | 1/1999 |
| JP | 11-155836 | 6/1999 |
| JP | 11-253504 | 9/1999 |
| JP | 2000-102523 | 4/2000 |
| JP | 2000-112335 | 4/2000 |
| JP | 2000-279463 | 10/2000 |
| JP | 3126901 | 11/2000 |
| JP | 2001-204850 | 7/2001 |
| JP | 3081786 | 8/2001 |
| JP | 2001-299842 | 10/2001 |
| JP | 2002-065891 | 3/2002 |
| JP | 2002-126019 | 5/2002 |
| JP | 3087709 | 5/2002 |
| JP | 2002-127058 | 8/2002 |
| JP | 2002-263213 | 9/2002 |
| JP | 2002-351993 | 12/2002 |
| JP | 2003-093451 | 4/2003 |
| JP | 2003-164544 | 6/2003 |
| JP | 2003-190235 | 7/2003 |
| JP | 2004-008751 | 1/2004 |
| JP | 2004-174692 | 6/2004 |
| WO | WO 92/13504 | 8/1992 |
| WO | WO 98/37926 | 9/1998 |
| WO | WO 98/43700 | 10/1998 |
| WO | WO 98/43701 | 10/1998 |
| WO | WO 98/46127 | 10/1998 |
| WO | WO 02/13673 | 2/2002 |
| WO | WO 02/35457 | 5/2002 |
| WO | WO 02/092164 | 11/2002 |
| WO | WO 03/023546 | 3/2003 |
| WO | WO 2004/050172 | 6/2004 |
| WO | WO 2005/074369 | 8/2005 |
| WO | WO 2005/074370 | 8/2005 |
| WO | WO 2005/074371 | 8/2005 |
| WO | WO 2005/074372 | 8/2005 |
| WO | WO 2005/074373 | 8/2005 |
| WO | WO 2005/075155 | 8/2005 |
| WO | WO 2005/086574 | 9/2005 |
| WO | WO 2005/087307 | 9/2005 |
| WO | WO 2005/105203 | 11/2005 |
| WO | WO 2006/021952 | 2/2006 |
| WO | WO 2006/061834 | 6/2006 |
| WO | WO 2006/082584 | 8/2006 |

OTHER PUBLICATIONS

Translation of Decision of Rejection Dated Feb. 1, 2011 From the Japanese Patent Office Re. Application No. 2006-552013.

Translation of Notification of Reason for Rejection Dated Feb. 3, 2011 From the Japanese Patent Office Re. Application No. 2006-552009.

(56) References Cited

OTHER PUBLICATIONS

Translation of Notification of Reasons for Rejection Dated Jan. 27, 2011 From the Japanese Patent Office Re. Application No. 2007-510233.
Official Action Dated Mar. 15, 2011 From U.S. Appl. No. 10/597,602.
Response Dated Feb. 22, 2011 to Official Decision of Rejection of Oct. 29, 2010 From the Japanese Patent Office Re. Application No. 2007-529131.
Official Action Dated Mar. 16, 2011 From the US Patent and Trademark Office Re.: U.S. Appl. No. 11/568,463.
Notice of Allowance Dated Feb. 16, 2011 From U.S. Appl. No. 10/597,675.
Translation of Notification of Reason for Rejection Dated Apr. 7, 2011 From the Japanese Patent Office Re. Application No. 2006-552014.
Translation of Notification of Reasons for Rejection Dated Apr. 6, 2011 From the Japanese Patent Office Re. Application No. 2006-215045.
Response Dated Apr. 6, 2011 to Notification of Reasons for Rejection of Jan. 27, 2011 From the Japanese Patent Office Re. Application No. 2007-510233.
Response Dated Apr. 10, 2011 to Notification of Reasons for Rejection of Dec. 15, 2010 From the Japanese Patent Office Re. Application No. 2009-027772.
Official Action Dated May 9, 2011 From U.S. Appl. No. 11/568,463.
Response Dated May 16, 2011 to Official Action of Mar. 15, 2011 From U.S. Appl. No. 10/597,602.
Translation of Questioning Dated May 25, 2011 From the Japanese Patent Office Re. Application No. 2006-552015.
Official Action Dated Jun. 15, 2010 From U.S. Appl. No. 10/597,671.
Translation of Notification of Reasons for Rejection Dated Jun. 6, 2011 From the Japanese Patent Office Re. Application No. 2009-027772.
International Preliminary Report on Patentability Dated May 11, 2006 From the International Preliminary Examining Authority Re.: Application No. PCT/IL2005/000137.
International Search Report and the Written Opinion Dated May 12, 2006 From the International Searching Authority Re.: Application No. PCT/IL05/00136.
International Search Report and the Written Opinion Dated Jul. 17, 2006 From the International Searching Authority Re.: Application No. PCT/IL05/00142.
Official Action Dated Sep. 14, 2010 From U.S. Appl. No. 10/597,756.
Official Action Dated Jun. 15, 2011 From U.S. Appl. No. 10/597,671.
Official Action Dated Dec. 29, 2008 From U.S. Appl. No. 11/792,477.
Response Dated Sep. 20, 2010 to Notice of Reason for Rejection of Jun. 4, 2010 From the Japanese Patent Office Re. Application No. 2007-529131.
Response Dated Sep. 22, 2010 to Notification of Reasons of Rejection of May 26, 2010 From the Japanese Patent Office Re. Application No. 2006-552013.
Response Dated Sep. 26, 2010 to Notification of Reason for Rejection of Jul. 9, 2010 From the Japanese Patent Office Re. Application No. 2006-552014.
Response Dated Sep. 27, 2010 to Notification of Reasons for Rejection of Jul. 12, 2010 From the Japanese Patent Office Re. Application No. 2006-215045.
Response Dated Sep. 27, 2010 to Official Action of Jun. 28, 2010 From U.S. Appl. No. 11/568,463.
Response Dated Jun. 14, 2011 to Notification of Reason for Rejection of Feb. 3, 2011 From the Japanese Patent Office Re. Application No. 2006-552009.
Translation of Decision of Rejection Dated Jun. 30, 2011 From the Japanese Patent Office Re. Application No. 2007-510233.
Translation of Notification of Reasons of Rejection Dated Jul. 4, 2011 From the Japanese Patent Office Re. Application No. 2006-552013.

Response Dated Jul. 6, 2011 to the Notification of Reasons for Rejection of Apr. 6, 2011 From the Japanese Patent Office Re. Application No. 2006-215045.
Response Dated Jun. 9, 2011 to Official Action of May 9, 2011 From U.S. Appl. No. 11/568,463.
Response Dated Jul. 12, 2011 to Official Action of Jun. 15, 2011 From U.S. Appl. No. 10/597,671.
Response Dated Jul. 18, 2011 to Official Action of Mar. 16, 2011 From U.S. Appl. No. 11/568,463.
Official Action Dated Jul. 18, 2011 From U.S. Appl. No. 10/597,602.
Response Dated Aug. 9, 2011 to Questioning of May 25, 2011 From the Japanese Patent Office Re. Application No. 2006-552015.
Official Action Dated Aug. 10, 2011 From U.S. Appl. No. 10/597,633.
Examination Report Dated Aug. 25, 2011 From the Government of India, Patent Office Intellectual Property Building Re.: Application No. 3230/CHENP/2006.
Examination Report Dated Aug. 25, 2011 From the Government of India, Patent Office, Intellectual Property Building Re. Application No. 3232/CHENP/2006.
Response Dated Aug. 24, 2011 to Notification of Reasons for Rejection of Jun. 6, 2011 From the Japanese Patent Office Re. Application No. 2009-027772.
Notice of Reasons for Rejection Dated Aug. 31, 2011 From the Japanese Patent Office Re. Application No. 2006-552009 and Its Translation Into English.
Official Action Dated Sep. 1, 2011 From U.S. Appl. No. 11/568,463.
Official Action Dated Sep. 23, 2011 From U.S. Appl. No. 10/597,671.
Response Dated Sep. 26, 2011 to Notification of Reasons of Rejection of Jul. 4, 2011 From the Japanese Patent Office Re. Application No. 2006-552013.
Response Dated Oct. 5, 2011 to Notification of Reason for Rejection of Apr. 7, 2011 From the Japanese Patent Office Re. Application No. 2006-552014.
Response Dated Oct. 10, 2011 to Official Action of Aug. 10, 2011 From U.S. Appl. No. 10/597,633.
Official Action Dated Oct. 7, 2011 From U.S. Appl. No. 11/568,463.
Response Dated Nov. 9, 2011 to Notice of Reasons for Rejection of Aug. 31, 2011 From the Japanese Patent Office Re. Application No. 2006-552009.
Translation of Notification of Reason for Rejection Dated Aug. 13, 2010 From the Japanese Patent Office Re. Application No. 2006-552009.
International Preliminary Report on Patentability Dated Jan. 23, 2006 From the International Preliminary Examining Authority Re.: Application No. PCT/IL2005/000135.
International Search Report and the Written Opinion Dated Sep. 6, 2006 From the International Searching Authority Re.: Application No. PCT/IL05/01318.
International Search Report Dated Jun. 2, 2005 From the International Searching Authority Re.: Application No. PCT/IL2005/000139.
International Search Report Dated Feb. 3, 2006 From the International Searching Authority Re.: Application No. PCT/IL05/00140.
International Search Report Dated Jun. 8, 2006 From the International Searching Authority Re.: Application No. PCT/IL05/00906.
International Search Report Dated Nov. 17, 2005 From the International Searching Authority Re.: Application No. PCT/IL2005/000137.
International Search Report Dated Oct. 17, 2005 From the International Searching Authority Re.: Application No. PCT/IL05/00138.
International Search Report Dated Aug. 24, 2005 From the International Searching Authority Re.: Application No. PCT/IL2005/000442.
International Search Report Dated Nov. 28, 2005 From the International Searching Authority Re.: Application No. PCT/IL2005/00141.
International Searching Report Dated Jun. 3, 2005 From the International Searching Authority Re.: Application No. PCT/IL2005/000135.
Official Action Dated Feb. 7, 2008 From U.S. Appl. No. 11/389,773.
Official Action Dated May 19, 2008 From U.S. Appl. No. 11/207,655.
Official Action Dated Jul. 26, 2007 From U.S. Appl. No. 11/389,773.

(56) References Cited

OTHER PUBLICATIONS

Official Action Dated Sep. 30, 2008 From U.S. Appl. No. 11/207,655.
Supplementary Partial European Search Report Dated Jan. 29, 2008 From the European Patent Office Re.: Application No. 05774725.5.
Written Opinion Dated Jun. 2, 2005 From the International Searching Authority Re.: Application No. PCT/IL2005/000139.
Written Opinion Dated Feb. 3, 2006 From the International Searching Authority Re.: Application No. PCT/IL05/00140.
Written Opinion Dated Jun. 3, 2005 From the International Searching Authority Re.: Application No. PCT/IL2005/000135.
Written Opinion Dated Jun. 8, 2006 From the International Searching Authority Re.: Application No. PCT/IL05/00906.
Written Opinion Dated Nov. 17, 2005 From the International Searching Authority Re.: Application No. PCT/IL2005/000137.
Written Opinion Dated Oct. 17, 2005 From the International Searching Authority Re.: Application No. PCT/IL05/00138.
Written Opinion Dated Aug. 24, 2005 From the International Searching Authority Re.: Application No. PCT/IL2005/000442.
Written Opinion Dated Nov. 28, 2005 From the International Searching Authority Re.: Application No. PCT/IL05/00141.
Russo "An Other Reality", Maariv, P.14, Oct. 26, 2004. Hebrew Only.
Response Dated Nov. 1, 2010 to Decision of Rejection of Jul. 9, 2010 From the Japanese Patent Office Re. Application No. 2006-552015.
Response Dated Dec. 6, 2010 to Official Action of Jul. 7, 2010 From U.S. Appl. No. 10/597,675.
Translation of Decision of Rejection Dated Jul. 9, 2010 From the Japanese Patent Office Re. Application No. 2006-552015.
Translation of Official Decision of Rejection Dated Oct. 29, 2010 From the Japanese Patent Office Re. Application No. 2007-529131.
Official Action Dated Jan. 27, 2012 From U.S. Appl. No. 10/597,605.
Invitation Pursuant to Rule 62a(1) EPC and Rule 63(1) EPC Dated Mar. 20, 2012 From the European Patent Office Re. Application No. 05703184.1.
Invitation Pursuant to Rule 62a(1) EPC and Rule 63(1) EPC Dated Mar. 20, 2012 From the European Patent Office Re. Application No. 05703183.3.
Notice of Allowance Dated Apr. 4, 2012 From U.S. Appl. No. 10/597,599.
Translation of Questioning Dated Jan. 13, 2012 From the Japanese Patent Office Re. Application No. 2006-552013.
Official Action Dated Jul. 22, 2008 From U.S. Appl. No. 11/389,773.
Supplemental Notice of Allowability Dated Aug. 9, 2011 From U.S. Appl. No. 10/597,675.
Official Action Dated Mar. 19, 2012 From U.S. Appl. No. 10/597,635.
Proceedings Further With the European Patent Applicaiton Pursuant to Rule 70(2) EPC Dated Feb. 23, 2012 From the European Patent Office Re. Application No. 05703181.7.
Supplementary European Search Report Dated Feb. 6, 2012 From the European Patent Office Re. Application No. 05703181.7.
Communication Pursuant to Article 94(3) EPC Dated Feb. 8, 2012 From the European Patent Office Re. Application No. 05703179.1.
Restriction Official Action Dated Dec. 12, 2011 From U.S. Appl. No. 10/597,635.
Response Dated Dec. 1, 2011 to Official Action of Sep. 1, 2011 From U.S. Appl. No. 11/883,663.
Amendment Dated Oct. 28, 2011 in Response to Decision of Rejection Dated Jun. 30, 2011 From the Japanese Patent Office Re. Application No. 2007-510233.
Notice of Allowance Dated Dec. 23, 2011 From U.S. Appl. No. 11/883,663.
Notice of Appeal Dated Oct. 28, 2011 in Response to Decision of Rejection Dated Jun. 30, 2011 From the Japanese Patent Office Re. Application No. 2007-510233.
Official Action Dated Jan. 11, 2012 From U.S. Appl. No. 10/597,602.
Translation of Notification of Reasons for Rejection Dated Dec. 21, 2011 From the Japanese Patent Office Re. Application No. 2006-552015.
Translation of Official Query Dated Dec. 16, 2011 From the Japanese Patent Office Re. Application No. 2007-529131.

Abe et al. "ICA. A Study of EEG Analysis Method Using ICA", Proceedings of the 1999 IEICE General Conference, p. 149, 1999.
Official Action Dated Jul. 18, 2013 From U.S. Appl. No. 10/597,633.
Official Action Dated Sep. 26, 2013 From U.S. Appl. No. 10/597,635.
Official Action Dated Jan. 16, 2014 From U.S. Appl. No. 10/597,635.
Invitation Pursuant to Rule 62a(1) and Rule 63(1) EPC Dated Mar. 20, 2012 From the European Patent Office Re. Application No. 05703185.8.
Applicant-Initiated Interview Summary Dated Jan. 23, 2013 From U.S. Appl. No. 10/597,671.
Examination Report Dated Aug. 25, 2011 From the Government of India, Patent Office, Intellectual Property Building Re.: Application No. 3231/CHENP/2006.
Notice of Allowance Dated Oct. 19, 2011 From the Japanese Patent Office Re. Application No. 2006-215045 and Its Translation Into English.
Official Action Dated Sep. 1, 2011 From U.S. Appl. No. 11/883,663.
Official Action Dated May 9, 2011 From U.S. Appl. No. 11/883,663.
Official Action Dated Nov. 27, 2012 From U.S. Appl. No. 10/597,633.
Applicant-Initiated Interview Summary Dated Oct. 25, 2012 From U.S. Appl. No. 10/597,602.
Communication Under Rule 71(3) EPC Dated Nov. 7, 2012 From the European Patent Office Re. Application No. 05703179.1.
Official Action Dated Sep. 7, 2012 From U.S. Appl. No. 10/597,671.
Official Action Dated Oct. 17, 2012 From U.S. Appl. No. 10/597,635.
Applicant-Initiated Interview Summary Dated Feb. 6, 2013 From U.S. Appl. No. 10/597,635.
Translation of Notification of Names of Appeal Examiners and Appeal Clerk Dated Jun. 6, 2012 From the Japanese Patent Office Re. Application No. 2006-552013.
Advisory Action Before the Filing of an Appeal Brief Dated Jul. 26, 2012 From U.S. Appl. No. 10/597,633.
Applicant-Initiated Interview Summary Dated Jun. 11, 2012 From U.S. Appl. No. 10/597,633.
Communication Pursuant to Article 94(3) EPC Dated Jul. 3, 2012 From the European Patent Office Re. Application No. 05703181.7.
Official Action Dated Aug. 1, 2012 From U.S. Appl. No. 10/597,605.
Official Action Dated Jun. 15, 2012 From U.S. Appl. No. 10/597,602.
Proceeding Further With the European Patent Application Pursuant to Rule 70(2) EPC Dated Jul. 30, 2012 From the European Patent Office Re. Application No. 05703185.8.
Proceedings Further With the European Patent Application Pursuant to Rule 70(2) EPC Dated Jul. 30, 2012 From the European Patent Office Re. Application No. 05703183.3.
Proceedings Further With the European Patent Application Pursuant to Rule 70(2) EPC Dated Jul. 30, 2012 From the European Patent Office Re. Application No. 05703184.1.
Supplementary Partial European Search Report Dated Jul. 11, 2012 From the European Patent Office Re. Application No. 05703183.3.
Supplementary Partial European Search Report Dated Jul. 11, 2012 From the European Patent Office Re. Application No. 05703184.1.
Supplementary Partiel European Search Report Dated Jul. 11, 2012 From the European Patent Office Re. Application No. 05703185.8.
Applicant-Initiated Interview Summary Dated Dec. 20, 2013 From U.S. Appl. No. 10/597,633.
Notice of Allowance Dated Jun. 10, 2013 From U.S. Appl. No. 10/597,671.
Communication Pursuant to Article 94(3) EPC Dated Mar. 19, 2013 From the European Patent Office Re. Application No. 05703183.3.
Communication Pursuant to Article 94(3) EPC Dated Mar. 19, 2013 From the European Patent Office Re. Application No. 05703184.1.
Communication Pursuant to Article 94(3) EPC Dated Mar. 19, 2013 From the European Patent Office Re. Application No. 05703185.8.
Official Action Dated May 14, 2012 From U.S. Appl. No. 10/597,633.
Communication Pursuant to Article 94(3) EPC Dated Jul. 17, 2014 From the European Patent Office Re. Application No. 05703181.7.
Communication Pursuant to Article 94(3) EPC Dated Jul. 28, 2014 From the European Patent Office Re. Application No. 05703183.3.
Communication Pursuant to Article 94(3) EPC Dated Jul. 28, 2014 From the European Patent Office Re. Application No. 05703184.1.

(56) References Cited

OTHER PUBLICATIONS

Communication Pursuant to Article 94(3) EPC Dated Jul. 28, 2014 From the European Patent Office Re. Application No. 05703185.8.
Kristy et al. "A Robotic Arm 'Smart Exercise System': A Rehabilitation Therapy Modality", Engineering in Medicine and Biology Society, Proceedings of the Annual International Conference of the IEEE Engineering in Images of the Twenty-First Century, XP010088537, p. 1504-1505, 1989.
Martens et al. "A FRIEND for Assisting Handicapped People. The Semiautonomous Robotic System 'FRIEND' Consists of an Electric Wheelchair With a Robotic Arm and Utilizes a Speech Interface", IEEE Robotics & Automation Magazine, XP055130671, 8(1): 57-65, Mar. 1, 2001.
Communication Pursuant to Article 94(3) EPC Dated May 13, 2014 From the European Patent Office Re. Application No. 06704564.1.
Applicant-Initiated Interview Summary Dated Aug. 1, 2014 From U.S. Appl. No. 10/597,605.
Official Action Dated Aug. 4, 2014 From U.S. Appl. No. 10/597,602.
Official Action Dated Apr. 10, 2014 From U.S. Appl. No. 10/597,605.
Backlife "The Backlife Idea", Product Information, <http://www.backlife.com>, 27 P., 2003.
Bak "The Complex Motion of Standing Still. Hydraulics, Sensors, and Human Modeling Dsta-Unified by Proprietary Software", <http://www.designnews.com/article/CA73202>, 5 P., 2001.
Burgar et al. "Development of Robots for Rehabilitation Therapy: The Palo Alto VA/Stanford Experience", Journal of Rehabilitation Research and Development, 37(6): 663-673, 2000.
Cameron et al. "Micromodular Implants to Provide Electrical Stimulation of Paralyzed Muscles and Limbs", IEEE Transactions on Biomedical Engineering, 44(9): 781-790, 1997. Abstract.
Graupe "EMG Pattern Analysis for Patient-Responsive Control of FES in Paraplegics for Walker-Supported Walking", IEEE Transactions on Biomedical Engineering, 36(7): 711-719, 1989. p. 711, 1-h Col., Paragraph 1 -r-h Col., Paragraph 1, Figs.3, 5, p. 716, 1-h Col., Figs.
Messinger "ReAbility Games: Island Hunt Catch'em Patrol Muzment", Detailed Specifications Document, NOKs Technologies, Version 1.0, 16 P., 2004.
Micromedical "BalanceQuest: Computerized Dynamic Posturography", Micromedical Technologies, <http://www.micromedial.com>, 6 P., 2001.
Motek "Motek Medical Rehabilitation: Rehabilitation", <http://www.e-motek.com>, 1 P., No date.
Peasgood et al. "EMG-Controlled Dosed Loop Electrical Stimulation Using a Digital Signal Processor", Electronics Letters, 36(22): 1832-1833, 2000. p. 1832, 1-h Col., Paragraph 1, Fig.1, p. 1833, r-h Col., Paragraph 1.
Richardson et al. "Comparing Smooth Arm Movement With the Two-Thirds Power Law and the Related Segmented-Control Hypothesis", The Journal of Neuroscience, 22(18): 8201-8211, 2002.
Viviani et al. "Minimum-Jerk, Two-Thirds Power Law, and Isochrony: Converging Approaches to Movement Planning", Journal of Experimental Psychology: Human Perception and Performance, 17: 32-53, 1995. Abstract.
Viviani et al. "Trajectory Determines Movement Dynamics", The Journal of Neuroscience, 7: 431-437, 1982.
Pfurtscheller et al. "Brain Oscillations Control Hand Orthosis in a Tetraplegic", Neuroscience Letters, 292: 211-214, 2000.
Translation of Notification of Reasons of Rejection Dated Jun. 12, 2009 From the Japanese Patent Office Re.: Application No. 2006-552011.
Translation of Notification of Reasons of Rejection Dated Sep. 14, 2009 From the Japanese Patent Office Re.: Application No. 2006-552014.
Communication Pursuant to Article 96(2) Dated Dec. 11, 2006 From the European Patent Office Re.: Application No. 05703180.9.
Examination Report Dated Oct. 23, 2008 From the Instituto Mexicano de la Propriedad Industrial Re.: Application No. PA/a/2006/008919.
Examination Report Dated Oct. 29, 2008 From the Instituto Mexicano de la Propriedad Industrial Re.: Application No. PA/a2006/008914.
International Preliminary Report on Patentability Dated Aug. 16, 2007 From the International Bureau of WIPO Re.: Application No. PCT/IL2006/000140.
International Preliminary Report on Patentability Dated Jan. 19, 2007 From the International Preliminary Examining Authority Re.: Application No. PCT/IL05/00138.
International Preliminary Report on Patentability Dated Apr. 26, 2007 From the International Bureau of WIPO Re.: Application No. PCT/IL2005/000139.
International Preliminary Report on Patentability Dated Sep. 29, 2008 From the International Preliminary Examining Authority Re.: Application No. PCT/IL06/00140.
International Search Report and the Written Opinion Dated Jan. 3, 2007 From the International Searching Authority Re.: Application No. PCT/IL06/00140.
Office Action Dated Sep. 26, 2008 From the State Intellectual Properety Office of the People's Republic of China Re.: Application No. 20580010391.4.
Official Action Dated Oct. 1, 2008 From U.S. Appl. No. 11/389,773.
Communication of Results From Examination Dated Oct. 23, 2008 From the Instituto Mexicano de la Propriedad Industrial Re.: Application No. PA/a/2006/008914 and Its Translation into English.
Conununication Pursuant to Article 94(3) EPC Dated Oct. 12, 2009 From the European Patent Office Re.: Application No. 06704564.1.
International Preliminary Report on Patentability Dated Mar. 8, 2007 From the International Bureau of WIPO Re.: Application No. PCT/IL2005/000906.
International Preliminary Report on Patentability Dated Jun. 12, 2006 From the International Preliminary Examining Authority Re.: Application No. PCT/IL2005/000442.
International Preliminary Report on Patentability Dated Aug. 17, 2006 From the International Bureau of WIPO Re.: Application No. PCT/IL2005/000136.
International Preliminary Report on Patentability Dated Aug. 17, 2006 From the International Bureau of WIPO Re.: Application No. PCT/IL2005/000140.
International Preliminary Report on Patentability Dated Aug. 17, 2006 From the International Bureau of WIPO Re.: Application No. PCT/IL2005/000141.
International Preliminary Report on Patentability Dated Jun. 21, 2007 From the International Bureau of WIPO Re.: Application No. PCT/IL2005/001318.
Notification of Reasons of Rejection Dated Jun. 4, 2009 From the Japanese Patent Office Re.: Application No. 2006-552011.
Notification of Reasons of Rejection Dated Sep. 14, 2009 From the Japanese Patent Office Re.: Application No. 2006-552015 and Its Translation Into English.
Official Action Dated Dec. 18, 2009 From U.S. Appl. No. 11/348,128.
Official Action Dated Mar. 19, 2010 From U.S. Appl. No. 10/597,675.
Official Action Dated May 19, 2009 From U.S. Appl. No. 11/792,477.
Official Action Dated Oct. 23, 2008 From the Instituto Mexicano de la Propriedad Industrial, Divisional Direction of Patents Re.: Application No. PA/a/2006/008919 and Its Translation Into English.
Official Action Dated Jun. 24, 2009 From U.S. Appl. No. 11/207,655.
Response Dated Feb. 7, 2010 to Notification of Reasons of Rejection Dated Sep. 14, 2009 From the Japanese Patent Office Re.: Application No. 2006-552015.
Response Dated Feb. 9, 2010 to Notification of Reasons of Rejection of Sep. 14, 2009 From the Japanese Patent Office Re.: Application No. 2006-552014.
Response Dated Apr. 13, 2010 to Communication Pursuant to Article 94(3) EPC of Oct. 12, 2009 From the European Patent Office Re.: Application No. 06704564.1.
Translation of Office Action Dated Jan. 21, 2009 From the Japanese Patent Office Re.: Application No. 2006-552008.
Response Dated Apr. 19, 2010 to Official Action of Mar. 19, 2010 From U.S. Appl. No. 10/597,675.

(56) References Cited

OTHER PUBLICATIONS

Supplementary Partial European Search Report and the European Search Opinion Dated Jul. 14, 2009 From the European Patent Office Re.: Application No. 06704564.1.
Proceeding Further With the European Patent Application Pursuant to Rule 70(2) EPC Dated Jul. 31, 2009 From the European Patent Office Re.: Application No. 06704564.1.
Translation of Notification of Reasons of Rejection Dated Mar.9, 2010 From the Japanese Patent Office Re.: Application No. 2006-552008.
Official Action Dated Jul. 7, 2010 From U.S. Appl. No. 10/597,675.
Translation of Notification of Reason for Rejection Dated Jul. 9, 2010 From the Japanese Patent Office Re. Application No. 2006-552014.
Official Action Dated Jun. 28, 2010 From U.S. Appl. No. 11/568,463.
Translation of Notification of Reasons of Rejection Dated May 26, 2010 From the Japanese Patent Office Re. Application No. 2006-552013.
Translation of Notice of Reason for Rejection Dated Jun. 4, 2010 From the Japanese Patent Office Re. Application No. 2007-529131.
Response Dated Aug. 4, 2010 to Notification of Reasons of Rejection of Mar. 9, 2010 From the Japanese Patent Office Re.: Application No. 2006-552008.
Translation of Notification of Reasons for Rejection Dated Jul. 12, 2010 From the Japanese Patent Office Re. Application No. 2006-215045.
Official Action Dated Nov. 15, 2011 From U.S. Appl. No. 10/597,633.
Response Dated Oct. 17, 2011 to Official Action of Jul. 18, 2011 From U.S. Appl. No. 10/597,602.
International Preliminary Report on Patentability Dated Apr. 21, 2010 From the International Preliminary Examining Authority Re.: Application No. PCT/IL05/00138.
Applicant-Initiated Interview Summary Dated Oct. 10, 2014 From the U.S. Appl. No. 10/597,602.
Communication Pursuant to Article 94(3) EPC Dated Sep. 29, 2014 From the European Patent Office Re. Application No. 06704564.1.
Notice of Allowability Dated Nov. 26, 2014 From the U.S. Appl. No. 10/597,605.
Supplemental Notice of Allowability Dated Oct. 29, 2014 From the U.S. Appl. No. 10/597,605.

\* cited by examiner

MOTOR TRAINING WITH BRAIN PLASTICITY

RELATED APPLICATIONS

This application is a U.S. National Phase of PCT Patent Application No. PCT/IL2005/000906 filed on Aug. 18, 2005, which is a continuation-in-part of PCT Patent Applications Nos. PCT/IL2005/000442, filed on Apr. 28, 2005; PCT/IL2005/000135; PCT/IL2005/000136; PCT/IL2005/000137; PCT/IL2005/000138; IL2005/000139 and PCT/IL2005/000142 all filed on Feb. 4, 2005. The contents of the above applications are incorporated herein by reference.

This application also claims the benefit of U.S. Provisional Patent Application Nos. 60/686,991 filed on Jun. 2, 2005; 60/633,429 filed on Dec. 7, 2004; 60/633,428 filed Dec. 7, 2004; 60/633,442 filed on Dec. 7, 2004; 60/604,615 filed Aug. 25, 2004.

This application is also related to U.S. Provisional Applications Nos. 60/666,136 filed Mar. 29, 2005; 60/665,886 filed Mar. 28, 2005 and U.S. patent application No. 11/207,655 filed Aug. 18, 2005, the contents of which are incorporated herein by reference.

FIELD OF THE INVENTION

The present invention is related to the field of motor and/or cognitive, training and/or rehabilitation, for example rehabilitation utilizing brain activity measurements.

BACKGROUND OF THE INVENTION

Following is a short introduction to measurement of some types of electrical brain activity associated with motor control and what is currently believed to be their meaning. It should be noted that application of the invention is not necessarily constrained by these meanings and other signals may be measured and/or the following signals be used in other ways. Various articles are listed at the end of the background section.

Movement-Associated Cortical Potential (MAC) Accompanying Voluntary Movement

Experiments have shown that every voluntary movement is associated with an electrical cortical potential that can be recorded over the scalp. This activity is typically characterized by three components:

1. The "Bereitschaftspotential" (BP) or "Readiness Potential" defined as a slowly 'rising' negative potential that occurs 1-2 seconds prior to volitional self-initiated movements. It is related to the preparatory process prior to limb movement.

This BP consists in fact of two components:
   an early component (BP1) that lasts from the very beginning of the BP (starting 1-2 s or more prior to movement onset depending on the complexity of the movement) to approximately 0.5 s before movement onset; and
   a late component (BP2) that occurs for the last half second before onset (see FIG. 1). BP2 has a steeper negative slope than BP1.

2. The motor potential (MP) which consists of an initial sharp negative deflection that follows the BP's more gradual negativity. This potential is related to motor activity. At movement onset (at t=0 as shown in FIG. 1 below), there exists a sharp positive inflection that peaks at around 200 ms after the movement onset. This period is typically contaminated with EMG artifacts.

3. The post-movement activity (PMA) which is the potential change (starting more than 200 ms after the movement onset) whereby the brain resynchronizes and resumes 'normal' activity.

FIG. 1 presents an averaged Motor Related Potential (MRP) template that illustrates these distinguishable periods. This in an example of an averaged MRP recorded for 918 left finger movement trials (onset at t=0) at C3 (channel 3) and C4 (channel 4).

For unilateral movement, BP1 typically has a symmetric and bilateral topography on the scalp, i.e. it is not lateralized about the motor cortex.

In contrast BP2 is typically larger (more negative) over the primary motor area of the contra lateral hemisphere. This is evident in FIG. 1 for the last ~200 ms prior to finger press at time t=0. The electrode C4 is positioned on the right side of the head and for the left finger movement as shown exhibits a more negative potential on average than the contra-laterally placed C3 electrode.

Rich experimental evidence indicates that BP1 and BP2 might involve different functional systems. Experiments in PET (Positron Emission Tomography) and unicellular recordings in monkeys suggested that parts of the mesial frontal cortex, and typically the Supplemental Motor Area, may be involved in the generation of BP1. On the other hand, several investigators concluded that BP2 potential reflects expression of nerve excitation, namely, activity of cortical-spinal tract concerning efferent discharges of pyramidal tract.

It has been suggested that the awareness of willingness to move occurred later than the beginning of the electrophysiological event and that, consequently, the first part of the decision process to move was infra-conscious, at least for self-paced tasks.

All the above supports the fundamental EEG theory that potential negativity can be related to activity of the cortical areas whereas positivity is related to inactivity. Since the extremities of the human body are controlled by the contra lateral side of the brain it is generally expected that there should be more activity and hence 'negativity' on the contra lateral side. However, it should be noted that this is not always the case.

It has been shown that, the signal distribution over the scalp of the BP2 potential shows maximum at C3, (central left scalp), in case of voluntary right upper arm flexion movement. The maximum was at C4, (central right scalp), in case of voluntary left upper arm flexion movement. The distribution of the late PMA potential showed maximum at Cz, (central medial) in case of voluntary right or left upper arm flexion movement. The only part of the MAC that shows potentials contra lateral to the side of the movement is BP2.

Contingent Negative Variation (CNV)

In some experimental setups the generation of a MAC potential involves the performance of a prescribed task under the prompting of a pair of cuing stimuli: S1 and S2, separated by a given time interval. The first cue, (S1), is a 'warning' or 'preparatory' cue which is subsequently followed by a second 'imperative' cue (S2).

The subject is instructed to perform the given task as fast as possible following the presentation of the imperative stimulus (S2). Briefly, the preparatory stimulus precedes the imperative and thus acts as a 'get ready' signal to warn the subject that the imperative stimulus is approaching.

Under these conditions, the resultant waveform recorded over the scalp is a slow negative shift beginning at the presentation of S1 and ending roughly at the presentation of S2.

FIG. 2 shows a typical event-related potential in an S1-S2 paradigm, measured from central derivations (average of C3 and C4). The x-axis shows the presentations of S1 (onset at time t=0), and S2 (onset at t=6 seconds). The measures for PSW, NSW, and CNV (shown on the figure) as used in the present study are indicated.

The task can be, for instance, that S1 is a sound which the subject had to decide if it belongs to a previously memorized set of sounds. The result of this memory search task indicates the response instruction expected at S2; for instance, that a response has to be given either with the left or with the right hand, depending on the result of the search.

Referring back to FIG. 2, within the first second after S1 a slow wave complex can be seen which consists of a positive (slow wave) deflection (the "PSW").

Later in the S1-S2 interval, a slow negative shift develops, which reaches a negative maximum immediately before S2. This shift is called the contingent negative variation (CNV).

When the S1-S2 interval is sufficiently long, three seconds or more, the negative shift clearly consists of two parts. The first part, called negative slow wave (NSW), is maximal at the frontal positions, between about 0.5 and 1 second after S1.

PSW has a parietal dominance and is assumed to reflect the outcome of stimulus evaluation and has been found to attenuate when the task is more difficult.

NSW has a frontal maximum, and some authors have found that it is lateralized in the right hemisphere. It is often regarded as part of an orientation reaction, because it is affected by the physical characteristics of S1, such as intensity, probability, and modality. The NSW is larger when the task at S1 is more difficult.

The CNV is mainly related to motor response preparation; its amplitude depends heavily on the task demands at S2, and is affected by task variables as speed/accuracy instructions, and the duration of the S1-S2 interval. CNV has the largest amplitude at the central electrodes.

CNV and Readiness Potential (BP)

CNV and BP are often considered to reflect the same process, since they are maximal at the same positions on the scalp, and immediately before a response is given. The difference between CNV and BP is, however, that the first is derived as a stimulus-locked potential, whereas the latter is derived relative to the response.

Whereas the BP is specific to motor readiness, and is concentrated over the primary motor cortex, the CNV is associated with more cognitive aspects of anticipation, and is generally localized to frontal and frontal-central cortex.

Topographic Plots of Bereitschafts Amplitudes with Different Types of Movement

In order to get a good picture of overall Motor Related Potential distribution effects, including lateralization effects, experimenters employ a two dimensional interpolation scheme from data collected through a multiple electrode arrangements. This technique facilitates the visualization of the topographic distribution of BP amplitudes over the entire scalp surface.

(Briefly, the data processing method consists of: first, the amplitude of the total negativity is measured algorithmically for each electrode position of the whole scalp arrangement. Because the data includes a large amount of high-frequency noise, a mean of 20-50 ms of voltage data is used to estimate the potential at the start and end of each BP waveform. The end value is then subtracted from the start value, thus yielding (in most cases) a positive magnitude for the negativity. These data is then combined with the known relative coordinates of each electrode to generate a two-dimensional grid interpolation of the overall negativity values. In addition, before the interpolation is applied, the EOG and EMG electrodes are removed from the data set as their given coordinates are figurative and they generally showed no evidence of significant waveforms.)

Free Movement

If subjects are asked to initiate a voluntary extension of the middle and ring fingers necessary and sufficient for production of a reliable Extensor Communis EMG signal of the right hand only, the recorded MAC is as in FIG. 3 (left) and the topographic distribution of the signal following the data processing described above is as in FIG. 3 (right).

CP2 (central parietal 2, slightly to the right of the central line and just below towards the back of the brain, relative to the point in FIG. 1). In the graph in FIG. 3 left shows the activity contra lateral to the movement. The translation of color into gray scale is as follows: Colors are gradual changing values. The two rounded dark areas in the center are positive peaks and the other dark areas are negative peaks.

In this case the voluntary movements are completely at the will of the participant, although a rough guideline is given to the subject to leave at least two to three seconds between movements. Accordingly, we can see most of the features described previously.

Synchronized Movement

If instead of moving the finger at will the subject is to initiate movement according to a self-maintained, even, metrical pulse with a rough guideline frequency of around 0.5 Hz, the resulting potentials are different. Ideally this will produce MAC events at the steady, regular rate of 0.5 Hz. These events should be phase locked to the subject's internal pulse. This is a 'synchronize' condition.

The resulting topographical maps are shown in FIG. 4 where BP amplitude is visualized as a color spectrum mapping (shown as grey scale). In these plots, a clear distribution effect of the experimental condition is even more evident than in the previous case of free movement. The dark area on the bottom is positive values and the dark area on the top is negative values.

As before, the movement consisted in the extension of the middle and ring fingers of the right hand sufficient for production of a reliable Extensor Communis EMG signal. It is clear that in this condition, the spread is mostly towards the left side of the head.

Applying the topographic algorithm described in the previous section, (mean of 20-50 ms of voltage data at beginning and end each signal), it can be seen that there are two spots of maximal amplitude of the whole signal: one is central and the other is slightly to the side contra lateral to the movement.

Syncopate Movement

In this case, the subject is again instructed to maintain an internal metrical pulse. However, in this trial the subject is instructed to initiate finger movements exactly counter to the pulse. That is, the movements should be phase shifted by half a period from the maintained internal pulse. Ideally this will produce MAC events at a frequency of 0.5 Hz, phase-shifted by 1 second from the internal pulse. This is the 'syncopate' condition. Results are shown in FIG. 5. (high values are at the bottom of the image, low on top).

From FIGS. 3-5 it can be seen that a clear distribution of the experimental condition is evident. First, there is an apparent spreading in the location of maximum BP amplitude in all the experimental conditions relative to the "Free Movement" condition. In the "Synchronized" conditions, the spread is mostly towards the left side of the head. In the "Syncopate" condition some spread to the right side is also present.

One potential effect is the appearance of CNV in the syncopate conditions. As described in a previous section, CNV usually marks expectation or anticipation in non-motor regimes.

Motor Imagery as Activator of Cortical Activation

Very recently a technique named "mirror therapy" has been reported to be used to activate unused cortical networks and help to reduce the pain associated with cortical abnormalities following injury as occurs in phantom pain and stroke. Briefly, "mirror therapy" involves the movement of a limb inside a mirror box such that visual feedback of the affected hand is replaced by that of the (reflected) unaffected hand. There is therefore an attempt to reconcile motor output and sensory feedback and to activate pre-motor cortices. In his last article, Moseley 2004 writes: "The mechanism of the healing effect of this technique, although not clear, may involve the sequential activation of cortical pre-motor and motor networks, or sustained and focused attention to the affected limb, or both."

Slow Cortical Potential (SCP)

SCP in general has been extensively used by Prof. Neils Birbaumer and his group in the University of Tuebingen, Germany. SCPs are potential shifts in the scalp-recorded EEG that occur over 0.5-10 sec. Negative and positive SCPs are typically associated with functions that involve cortical activation and deactivation, respectively. Healthy subjects and neurological patients can attain reliable control over their SCPs amplitude and polarity recorded at frontal and parietal locations by means of sensory (e.g., visual and audio) feedback. In addition, subjects can learn to control SCP differences between the left and right hemisphere.

Mu Rhythm

When a person is at rest, his sensorimotor cortex generates an 8-13 Hz electro-encephalographic rhythm referred to as the "Rolandic mu rhythm". As soon as the person starts to execute a movement and the motor cortex is activated, the mu rhythm is attenuated or disappears. The mu rhythm is present in most, if not all, adults, it is generated by a thalamo-cortical network and it is strongest when no active processing is occurring. Decreases in mu amplitude possibly indicate that the underlying cell assemblies have become desynchronized (hence, lower mu rhythm amplitudes are recorded over the scalp). The mu rhythm also desynchronizes when subjects are only observing (but not executing) a movement and the degree of desynchronization reflects the level of active processing; for instance, it is greater when a person is performing a precision grip than during the performance of a simple hand extension. These rhythms also respond to imagination of movement in a pattern similar to that during the planning of a movement. For instance, subjects with limb amputation that mentally mobilize the missing limb, show a blocking effect of mu rhythm while imagining the movement.

Feedback training leads to increase in mu desynchronization; and the ability of subjects to manipulate the sensorimotor mu rhythm has been recently used by Wolpaw et al. group to act as a brain-computer interface based on a binary signal. For instance, subjects can learn to produce similar or differential mu activity over the two hemispheres in order to control left or right movement in a three-dimensional video game.

Sometimes differences of amplitude in both hemispheres are recorded for two frequency band rhythms to allow for a bi-dimensional movement over the screen. For instance, in Wolpaw et al (Jonathan R. Wolpaw and Dennis J McFarland 2004. *Control of a two-dimensional movement signal by a noninvasive brain-computer interface in humans. PNAS* 2004, vol. 10, no. 51: 17849-17854), the disclosure of which is incorporated herein by reference, use vertical movement of a cursor was controlled by a 24-Hz beta rhythm and horizontal movement by a 12-Hz mu rhythm recorded at left- and right-side scalp electrodes locations C3 and C4 over the sensorimotor region. Vertical correlation is greater on the left side, whereas horizontal correlation is greater on the right side.

FIG. 9 shows on the left the various positions on the screen towards which the user learns to move the cursor from a center position. On center/right of FIG. 9 there are the recordings of brain potential when a user tries to move to Target 1 (up), Target 6 (down), Target 3 (right) and Target 8 (left). It can be seen, for instance, that in order to move to Target 1 (up) the user needs to increase Beta rhythm (24 Hz) recorded over the C3 and in order to move to Target 8 (left) the user needs to reduce the mu rhythm (12 Hz) recorded over the C4 region. In the figure, vertical control has two positive peaks as shown, while in horizontal control, the left peak is a negative peak and the right peak is a positive peak.

Many studies have demonstrated that humans can learn to control µ-rhythm amplitudes independent of actual movement and use that control to move a cursor to targets on a computer screen (Walpow et al., 1991; McFarland et al., 1993; Pfurtscheller et al., 1993), or to control an artificial hand attached to the paretic hand (Pfurtscheller et al., 2003). None of these studies, apparently was conducted in stroke patients or other patients with brain damage, such as that due to traumatic brain injury.

Cortical Reorganization after Stroke

Return of voluntary arm movements is one of the most important goals during stroke rehabilitation to avoid long-term disability in activities of daily living (ADL) function.

Some studies have demonstrated recruitment of areas adjacent to the brain lesion or ipsilateral motor regions of the unaffected hemisphere after complete recovery from upper extremity motor impairment. Rossini et al. (1998) for example, who used brain imaging methods as functional magnetic resonance imaging (fMRI), transcranial magnetic stimulation (TMS), and magnetoencephalography (MEG) to examine a patient who fully recovered after stroke, found an asymmetrical enlargement and posterior shift of the sensorimotor areas localized in the affected hemisphere with all three techniques.

Nelles et al. (1999), used serial positron emission tomography (PET) to study the evolution of functional brain activity within 12 weeks after a first subcortical stroke. Six hemiplegic stroke patients were scanned twice (PET 1 and PET 2). At PET 1, activation was observed in the bilateral inferior parietal cortex, contralateral sensorimotor cortex, and ipsilateral dorsolateral prefrontal cortex, supplementary motor area, and cingulate cortex. At PET 2, significant increases of regional cerebral blood flow were found in the contralateral sensorimotor cortex and bilateral inferior parietal cortex. A region that was activated at PET 2 only was found in the ipsilateral premotor area. Based of their findings, Nelles et al conclude that recovery from hemiplegia is accompanied by changes of brain activation in sensory and motor systems, and that these alterations of cerebral activity may be critical for the restoration of motor function.

Johansen-Berg et al. (2002) examined seven stroke patients with fMRI twice before and twice after a home-based two weeks rehabilitative therapy. They found that therapy-related improvements in hand function correlated with increases in fMRI activity in the premotor cortex and secondary somatosensory cortex contralateral to the affected hand, and in superior posterior regions of the cerebellar hemispheres bilaterally. As the former studies, these results suggest that activity changes in sensorimotor regions are associated with successful motor rehabilitation.

In addition, accumulating evidence in stroke patients suggests that rehabilitation techniques with repetitive training of functional movements have significant effects on recovery of motor skills and cortical reorganization. Lipert et al. (2000), for example, evaluated reorganization in the motor cortex of stroke patients that was induced with an efficacious rehabilitation treatment. Before treatment, the cortical representation area of the affected hand muscle was significantly smaller than the contralateral side. After a 12-day-period of constraint-induced movement therapy, the muscle output area size in the affected hemisphere was significantly enlarged, corresponding to a greatly improved motor performance of the paretic limb. Shifts of the center of the output map in the affected hemisphere suggested the recruitment of adjacent brain areas. In follow-up examinations up to 6 months after treatment, motor performance remained at a high level, whereas the cortical area sizes in the 2 hemispheres became almost identical, representing a return of the balance of excitability between the 2 hemispheres toward a normal condition.

Luft et al. (2004) tested whether specific rehabilitation therapy that improves arm function in stroke patients is associated with reorganization of cortical networks. Patients were randomly assigned to bilateral arm training (n=9) or standardized dose-matched therapeutic exercises (n=12). Both were conducted for 1 hour, 3 times a week, for 6 weeks. Within 2 weeks before and after the intervention, brain activation during elbow movement was assessed by fMRI and functional outcome was assessed using arm function scores. Patients in the first group (bilateral arm training) but not in the second group increased hemispheric activation during paretic arm movement. Significant increased activation was observed in the contralesional cerebrum and ipsilesional cerebellum. These findings suggest that bilateral arm treatment induces reorganization in contralesional motor networks and provide biological plausibility for repetitive bilateral training as a potential therapy for upper extremity rehabilitation in hemiparetic stroke.

Summary

Numerous studies have demonstrated that the damaged brain is able to reorganize to compensate for motor deficits. Rather than a complete substitution of function, the main mechanism underlying recovery of motor abilities involves enhanced activity in preexisting networks, including the disconnected motor cortex in subcortical stroke and the infarct rim after cortical stroke. Involvement of nonmotor and contralesional motor areas is consistently reported, with the emerging notion that the greater the involvement of the ipsilesional motor network, the better is the recovery. A better stroke recovery seems to take place if the changes in certain brain areas over time are such that the normal balance between the 2 hemispheres tends to reestablish. Thus, recovery is best when the brain regions that normally execute the function are reintegrated into the active network. Consistent with this view, intense rehabilitative procedures (both active and passive) have recently been shown to enhance activation of the ipsilesional motor area in parallel with improved motor function.

Consistent results were a dynamic reorganization that went along with recovery, over-activation of motor and non-motor areas in both hemispheres regardless of whether the task was active or passive leading to a decrease in the laterality index, and a return toward a more normal intensity while the affected hand regained function (Calautti and Baron, 2003). In some embodiments of the invention, as described below, such results are achieved using methods and apparatus as described herein.

Some components of brain activity (e.g., SCPs) can be controlled by increasing or decreasing the general brain activity, independent from the recorded site. Subjects can learn to control SCP differences between the left and right hemisphere (Rockstroh et al., 1990).

Brain-Computer Interface (BCI)

A BCI system measures particular components of features of EEG activity and uses the results as a control signal. Present-day BCIs determine the intent of the user from a variety of different electrophysiological signals. These signals include slow cortical potentials (SCP), P300 potentials, and $\mu$ (mu) or beta rhythms recorded from the scalp, and cortical neuronal activity recorded by implanted electrodes (referred as Brain-Machine Interface, BMI). They are translated in real-time into commands that operate a computer display or other device.

A BCI converts a signal such as an EEG rhythm or a neuronal firing rate from a reflection of brain function into the end product of that function: an output that, like output in conventional neuromuscular channels, accomplishes the person's intent. A BCI replaces nerves and muscles and the movements they produce with electrophysiological signals and the hardware and software that translate those signals into actions.

Many studies have demonstrated that healthy subjects and neurological patients can attain reliable control over their slow cortical potentials (SCPs) amplitude at vertex, frontal and parietal locations with operant learning. Moreover, subjects can learn to control SCP differences between the left and right hemisphere (Birbaumer et al., 1999; Birbaumer et al., 1988; Rockstroh et al., 1990). Successful learning using reinforcement and shaping of the response results in the acquisition of a new, non-motor skill (Birbaumer et al., 1999). Studies involving mu-rhythm (Walpow et al, 2002) confirm and extend these findings.

The following articles, some of which are referenced herein, have their disclosures incorporated herein by reference:

International Journal of Psychphysiology 9 (1990) 151-165 "Biofeedback-produced hemispheric asymetry of slow cortical potentials and its behavioural effects", by B Rockstroh, T Elbert, N Birbaurmer and w Lutzenberger.

Wolpaw, J. R., McFarland, D. J., Neat, G. W. and Forneris, C. A. "An EEG-based brain-computer interface for cursor control" Electroenceph. clin. Neurophysiol., 1991, 78:252-259.

McFarland, D. J., Neat, G. W., Read, R. F. and Wolpaw, J. R. "An EEG-based method for graded cursor control" Psychobiology, 1993, 21: 77-81.

Pfurtscheller, G., Flotzinger, D. and Kalcher, J. "Brain-computer interface: a new communication device for handicapped persons" Journal of Microcomputer Applications, 1993, 16:293-299.

"Arm Training Induced Brain Plasticity in Stroke Studied with Serial Positron Emission Tomography" G. Nelles, W. Jentzen, M. Jueptner, S. Muller, and H. C. Diener. NeuroImage 13, 1146-1154 (2001) doi:10.1006/nimg.2001.0757.

"Control of a two-dimensional movement signal by a non-invasive brain-computer interface in humans" Jonathan R. Wolpaw and Dennis J. McFarland. PNAS Dec. 21, 2004 vol. 101 no. 51 17849-17854

"'Thought'—control of functional electrical stimulation to restore hand grasp in a patient with tetraplegia" Gert Pfurtschellera, Gernot R. Muller, Jorg Pfurtscheller, Hans Juürgen Gernerd, Rudiger Ruppd. Neuroscience Letters 351 (2003) 33-36

Nelles G, Spiekermann G, Jueptner M, Leonhardt G, Muller S, Gerhard H, Diener H C. "Evolution of functional reorganization in hemiplegic stroke: a serial positron emission tomographic activation study" Ann Neurol 1999; 46:901-909

"Hand motor cortical area reorganization in stroke: a study with fMRI, MEG and TCS maps" P. M. Rossini, C. Caltagirone, A. Castriota-Scanderbeg, P. Cicinelli, C. Del Gratta, M. Demartin, V. Pizzella, R. Traversal and G. L. Romanil. NeuroReport 9, 2141-2146 (1998)

"Correlation between motor improvements and altered fMRI activity after rehabilitative therapy" Heidi Johansen-Berg, Helen Dawes, Claire Guy, Stephen M. Smith, Derick T. Wade and Paul M. Matthews. Brain (2002), 125, 2731-2742

"Treatment-Induced Cortical Reorganization After Stroke in Humans" Joachim Liepert, MD; Heike Bauder, PhD; Wolfgang H. R. Miltner, PhD; Edward Taub, PhD; Cornelius Weiller, MD (Stroke. 2000; 31:1210-1216.)

Birbaumer, N. et al. (1999). "A spelling device for the paralysed." Nature 398(297-298).

Birbaumer, N., et al. (1988). "Slow brain potentials, imagery and hemispheric differences." International Journal of Neuroscience 39: 101-116.

Rockslroh, B., et al. (1990). "Biofeedback-produced hemispheric asymmetry of slow cortical potentials and its behavioral effects." International Journal of Psychophysiology 9(2): 151-165.

Wolpaw, J. R., Birbaumer, N., McFarland, D. J., Pfurtscheller, G., Vaughan, T. M., 2002. Brain/computer interfaces for communication and control. Clinical Neurophysiology 113, 767-791.

Ward N S, Brown M M, Thompson A J, Frackowiak R S. Neural correlates of outcome after stroke: a cross-sectional fMRI study. Brain 2003; 126:1430-1448.

"Repetitive Bilateral Arm Training and Motor Cortex Activation in Chronic Stroke A Randomized Controlled Trial" JAMA. 2004; 292:1853-1861

"Functional Neuroimaging Studies of Motor Recovery After Stroke in Adults A Review" Cinzia Calautti, MD; Jean-Claude Baron, MD, FRCP, FMedSci (Stroke. 2003; 34:1553-1566.)

SUMMARY OF THE INVENTION

A broad aspect of some embodiments of the invention relates to robot-assisted rehabilitation which utilizes EEG or other assessment of brain activity. In an exemplary embodiment of the invention, the assessment is used to induce and/or measure brain plasticity. In an exemplary embodiment of the invention, brain and manipulator function are correlated or interact, for example, using one to trigger or generate the other.

In an exemplary embodiment of the invention, measurements of brain activity are used to provide feedback to one or more of patient, system and/or therapist, for example, during an exercise, during a session and/or between sessions. In an exemplary embodiment of the invention, the cortical effect of a rehabilitation exercise is thus assessed and/or optionally correlated with physical effect of the rehabilitation. This may be used to identify problems in the rehabilitation process and/or patient limitations. In an exemplary embodiment of the invention, the feedback is used for more cortically specific rehabilitation, in which rehabilitation exercises and/or parameters are used to selectively focus on certain brain areas and/or restructuring methodologies. Optionally, an exercise is used if it shows a desired selective, cortical and/or restructuring effect. The exercise is optionally dropped, reduced in importance and/or its parameters changed, if a desired effect is not found.

In an exemplary embodiment of the invention, the rehabilitation is used to obtain an improvement effect on motion and/or on a desire to carry out a motion.

In an exemplary embodiment of the invention, a goal of rehabilitation is to improve an innate cortical ability and/or matching between cortical ability and physical ability. Optionally, this rehabilitation includes performing a plurality of exercises (typically over 100, over 1000 or over 10,000, or intermediate numbers, within a short period of time, such as less than 1 month, less than one week or intermediate times), optionally with many exact or approximate repetitions and modifying an exercise parameter according to improvement in function. Optionally, safety considerations are applied during rehabilitation. Optionally, the rehabilitation is under supervision of a physical therapist. Typically one or more rehabilitation goals are provided, for example a percent improvement in control of a limb and/or activity.

A broad aspect of some embodiments of the invention relates to assisting cognitive rehabilitation using a robotic manipulation system.

In an exemplary embodiment of the invention, selective treatment of brain areas is provided. In an exemplary embodiment of the invention, a manipulation and measurement system optionally as described herein is used to identify the edge of a damaged area in the brain, so that plasticity and rehabilitation efforts may focus on that area. Optionally, such an edge area is identified by its having a ragged activation profile.

In an exemplary embodiment of the invention, local activation is provided, for example, by one or more of heating, magnetic brain stimulation, electrical stimulation and/or drug delivery. In an exemplary embodiment of the invention, selective activation of the relevant brain area is provided by cognitive feedback training of the patient to activate a brain area and then provision of a drug or other generalized treatment. Optionally, such selectively is applied before, during and/or after a physical rehabilitation exercise which addresses that area. Optionally, the timing and/or relative triggering are provided by a manipulator system which measures brain activity and/or physical activity.

In an exemplary embodiment of the invention, a manipulation device is used for providing direct cortical rehabilitation. In an exemplary embodiment of the invention, SCP signals recorded from a single point of the scalp, (for instance Cz), are used in a biofeedback fashion to teach the patient to control the negativity (cortical activation) or positivity (cortical deactivation) of the signal at that point. Once the patient is able to control the SCP signal at a single point, one feature of the signal (for instance its negativity) is optionally used to drive a manipulator in space, for example, in a mono-directional fashion in one plane. Later, after further progress of the patient, optionally, the various features of the signal are translated into a binary code used to drive the manipulator in space in a mono-directional fashion in one plane. Later after yet further progress, optionally, by measuring at various different points over the scalp, the patient is trained to control the SCP signal at each one of them simultaneously and that information is translated into binary codes used to teach the patient to drive the manipulator in space in a multidirectional fashion; optionally, first in a single plane and later in a three dimensional mode. The manipulator may be used for one or both of producing a movement as a response to the particular combination of cortical signals and/or enhance and amplifying traces of movement conquered by the patient. Optionally, the patient is selectively instructed to try and carry out motions and/or image the motions.

A broad aspect of some embodiments of the invention, relates to the use of a manipulator to improve measurement capabilities. In an exemplary embodiment of the invention, repetitive or selectively different motions by the manipulator are used to better detect brain activation and/or tease apart different sources of brain activity.

In an exemplary embodiment of the invention, repetitive specific motion is used to define a cortical signal, for example, for comparison or for deciding on treatment. In an exemplary embodiment of the invention, the fact that a repetitive manipulator is used, allows brain signals recorded over multiple trials to be combined and averaged. Optionally, the manipulator is used to trigger the movement, so that the signals can be aligned in time. Optionally, the motion includes motion of a healthy arm and of a paretic arm. The healthy arm movements are optionally detected by the manipulator and used as the above trigger.

An aspect of some embodiments of the invention relates to using a robotic manipulator to provide incorrect or partial motions. In one example, the robotic manipulator applies force which is contrary to a motion planned by a patient. This may be used, for example, for assessment, by measuring the patient response, or as training to overcome physical obstacles or train certain brain areas. In another example, a robotic manipulator starts a motion and then becomes passive, or less active, to see if the patient can compensate or complete a motion on its own. In another example, the manipulator can be used to allow a patient (or therapist) to plan motion and/or make changes in planned motions, so that the patient can experience motions and cognitive activates not otherwise possible. Optionally, after such planning, the motion is executed or the patient is assisted with the motion. Optionally, a graphical interface is used for such planning or changing. Alternatively or additionally, a physical interface of the manipulator making a motion or a patient moving the manipulator, is used as an input device by the patient. Optionally, brain activity during such planning is also measured and optionally shown to the patient (e.g., directly or in simplified form) as feedback or to show progress in planning ability.

An aspect of some embodiments of the invention relates to daily assessment of mental state as part of rehabilitation. In an exemplary embodiment of the invention, brain image, blood tests and/or EEG measurements are used to assess an instant mental state of a patient, for example, depression. Optionally, depending on the motivational state of the patient additional motivation may be provided and/or lesser achievements may be expected. It should be noted that this type of depression relates to a mood, which can change hourly or daily and not to clinical depression which is a long term illness.

In an exemplary embodiment of the invention, cognitive rehabilitation progress is assessed using other means, such as problem solving or other cognitive tests. Optionally, cognitive progress is used to calibrate expected physical rehabilitation progression An aspect of some embodiments of the invention relates to ensuring and/or confirming a correct mental imagery by a patient by actually carrying out the motion or a similar motion for the patient. In some cases, damage to the brain may make such imaging difficult or impossible. In other cases, it is not clear if the patient correctly understood instructions. In an exemplary embodiment of the invention, the presented motion can then be compared exactly to an actually carried out motion. In this and other embodiments of the invention, a robotic manipulator may be replaced by one or more position and/or orientation sensing devices and having a human move the patient and the motion be tracked by the position sensing device. However, an advantage of a robotic manipulator is being able to define ahead of time what the motion or motion response will be, which is generally not as precise with a human manipulator.

In an exemplary embodiment of the invention, the mental imagery is stimulated using instruction (even with eyes closed) and/or presenting a movie or actual motion. Optionally, the movie is of the patient himself moving. Optionally, what is shown is a process image, for example, a mirror image of a motion carried out using a healthy arm, for a paretic arm.

In an exemplary embodiment of the invention, the provided motion is a partial motion or only includes hints, for example, stopping points along the motion rather than a complete motion. Optionally, a motion that is intentionally different to what is to be done, is used, for example, to force the patient to carry out mental manipulation (e.g., translation and/or rotation) of a motion in his head.

Optionally, the motion used for the guided mental imagery is changed, for example, to prevent habilitation of the patient thereto.

An aspect of some embodiments of the invention relates to using a dosage scheme for rehabilitation. In an exemplary embodiment of the invention, the dosage scheme relates to one or both of the effect on a patient and/or the activity of the patient, rather than merely time spent. In an exemplary embodiment of the invention, dosage control is applied in which a minimum exertion (mental and/or physical) and/or attention level are required. Alternatively or additionally, a desired level and/or a maximum level are proscribed. In an exemplary embodiment of the invention, a rehabilitation system monitors the actual applied dosage for one or both of calculating billing and ensuring dosage compliance.

There is thus provided in accordance with an exemplary embodiment of the invention, a rehabilitation device, comprising:

a movement element capable of controlling at least one motion parameter of a portion of a patient;

a brain monitor which generates a signal indicative of brain activity; and circuitry including a memory having stored therein rehabilitation information and which inter-relates said signal and movement of said movement element as part of a rehabilitation process which utilizes said rehabilitation information.

Optionally, said portion is a limb.

In an exemplary embodiment of the invention, said circuitry controls said movement element.

In an exemplary embodiment of the invention, said circuitry controls at least one of the direction and location of a movement or a reach point.

In an exemplary embodiment of the invention, said circuitry controls at least one of resistance to movement, speed and movement mode.

In an exemplary embodiment of the invention, said circuitry measures at least one parameter of motion of said movement element. Optionally, said circuitry measures at least one of force, movement vector and speed of said movement.

In an exemplary embodiment of the invention, said rehabilitation information comprises a rehabilitation plan.

In an exemplary embodiment of the invention, said rehabilitation information comprises a rehabilitation diagnosis.

In an exemplary embodiment of the invention, said rehabilitation information comprises at least one template of expected brain-motion relationship.

In an exemplary embodiment of the invention, said circuitry is adapted to generate an expected motion based on said measurement.

In an exemplary embodiment of the invention, said circuitry is adapted to generate an expected brain activity based on movement of said movement element.

In an exemplary embodiment of the invention, said circuitry is adapted to compare said measurement to said rehabilitation information.

In an exemplary embodiment of the invention, said circuitry is adapted to compare rehabilitation improvements of said patient to trends in said rehabilitation information.

In an exemplary embodiment of the invention, said circuitry is adapted to change at least one motion parameter responsive to said measurement. Optionally, said change is within a time frame of said movement.

In an exemplary embodiment of the invention, said circuitry is adapted to detect an intent to move of said patient and provide control of said movement element in response thereto.

In an exemplary embodiment of the invention, said circuitry is adapted to detect a readiness to move and provide control of said movement element in response thereto.

In an exemplary embodiment of the invention, said circuitry is adapted to change a signal processing of said measurement responsive to a detection of movement or lack thereof.

In an exemplary embodiment of the invention, said brain monitor comprises an EEG monitor.

In an exemplary embodiment of the invention, said brain monitor comprises a blood flow measuring device.

In an exemplary embodiment of the invention, said brain monitor comprises an fMRI system.

In an exemplary embodiment of the invention, said movement element comprises a robotic manipulator.

In an exemplary embodiment of the invention, said movement element comprises a resistive movement element which resists motion in a controllable manner.

In an exemplary embodiment of the invention, said movement element is adapted to be capable of substantially unrestricted movement in 3D space over a volume of at least 30 cm in minimum dimension.

In an exemplary embodiment of the invention, said movement element is adapted to be selectively coupled and decoupled to at least one type of body portion.

In an exemplary embodiment of the invention, said circuitry is adapted to provide cognitive rehabilitation to said patient.

In an exemplary embodiment of the invention, said circuitry comprises a memory which stores a rehabilitation progress of said patient.

In an exemplary embodiment of the invention, the device comprises at least two movement elements which said circuitry is configured to identify as being associated with opposite limbs.

There is also provided in accordance with an exemplary embodiment of the invention, a method of rehabilitation, comprising:

controlling the motion of at least part of a patient as part of a rehabilitation process; and measuring brain activity of said patient, in association with said controlling.

Optionally, the method comprises:

(a) deciding on a desired brain rehabilitation; and (b) controlling said motion to effect said rehabilitation.

Optionally, said desired rehabilitation comprises cortical reorganization.

In an exemplary embodiment of the invention, the method comprises diagnosing the patient based on said measuring. Optionally, diagnosing comprises controlling said motion to achieve a plurality of desired motions for said diagnosis. Alternatively or additionally, diagnosing comprises generating at least an indication of brain plasticity for said patient.

In an exemplary embodiment of the invention, the method comprises controlling said motion in response to said measuring.

In an exemplary embodiment of the invention, the method comprises controlling said measuring in response to said motion.

In an exemplary embodiment of the invention, the method comprises measuring during said motion.

In an exemplary embodiment of the invention, the method comprises repeating said controlling and said measuring for a same motion at least 10 times.

In an exemplary embodiment of the invention, the method comprises repeating said controlling and said measuring for at least 20 different motions in a same day of rehabilitation.

In an exemplary embodiment of the invention, the method comprises comparing measurements for a healthy side and a paretic side.

In an exemplary embodiment of the invention, the method comprises comparing movements for a healthy side and a paretic side.

In an exemplary embodiment of the invention, the method comprises measuring said motion.

In an exemplary embodiment of the invention, the method comprises measuring a quality of said motion.

In an exemplary embodiment of the invention, the method comprises tracking a progress of said rehabilitation process of said patient based on said measurements.

In an exemplary embodiment of the invention, the method comprises training a patient to control cortical activity using said controlling of motion as feedback.

There is also provided in accordance with an exemplary embodiment of the invention, a method of treatment targeting, comprising:

a patient locally activating a brain region; and applying treatment to said brain region in synchrony to said activation.

Optionally, applying treatment comprises physical rehabilitation which uses said brain region.

Optionally, applying treatment comprises delivering a drug.

In an exemplary embodiment of the invention, stimulating said brain region using external means that directly stimulate brain tissue.

In an exemplary embodiment of the invention, said locally activating comprises forcing a patient to locally activate a region using a physical exercise.

In an exemplary embodiment of the invention, said locally activating comprises detecting local activation of said region.

There is also provided in accordance with an exemplary embodiment of the invention, a method of brain monitoring, comprising:

generating brain activity by at least guiding a patient to at least intend to carry out a known physical activity;

first monitoring brain activity using a first brain monitor;

second monitoring said activity using a second brain monitor of a different type;

determining a correspondence between results of said first and said second monitoring;

performing rehabilitation on said patient using said second monitor; and assessing a brain activity of said patient during said performing utilizing a correspondence between said first monitoring and said second monitoring.

Optionally, said assessing comprises assuming a fixed relationship between said results.

Optionally, said generating comprises generating under computer control.

Optionally, said generating comprises repeating a same at least intent at least 10 times.

Optionally, said second monitoring comprises electrical monitoring.

Optionally, said second monitoring is significantly lower cost than said first monitoring.

Optionally, said first monitoring comprises fMRI.

There is also provided in accordance with an exemplary embodiment of the invention, a method of rehabilitation comprising:

(a) reorganizing brain functions; and (b) after said reorganizing rehabilitating motor control utilizing said reorganizing.

Optionally, said reorganization comprises reorganizing using a physical manipulation system to provide feedback to a patient.

There is also provided in accordance with an exemplary embodiment of the invention, a method of controlling rehabilitation, comprising:

defining a desired dosage of a rehabilitation for a patient, wherein said dosage is defined as a function of patient activity;

monitoring the application of said dosage to the patient using a computerized rehabilitation system.

Optionally, said dosage comprises a dosage of physical exertion.

Optionally, said dosage comprises a dosage of mental exertion.

Optionally, said dosage comprises a dosage of attention.

Optionally, said dosage is defined per a brain region.

There is also provided in accordance with an exemplary embodiment of the invention, a method of measuring brain patterns, comprising:

providing repeated movement exercises of a patient, under computer control; and collecting measurements of brain activity from said repeated movements; and analyzing said measurements to yield a more precise measurement of brain activity in response to the movement.

Optionally, the method comprises filtering out bad measurements.

In an exemplary embodiment of the invention, the method comprises programming a BCI using said more precise measurement.

In an exemplary embodiment of the invention, the method comprises analyzing said more precise measurement to diagnose said patient.

In an exemplary embodiment of the invention, said diagnosis comprises a quality of brain activity.

In an exemplary embodiment of the invention, said diagnosis comprises brain plasticity.

In an exemplary embodiment of the invention, the method comprises analyzing said more precise measurement to close a loop in a rehabilitation process.

There is also provided in accordance with an exemplary embodiment of the invention, a method of rehabilitation, comprising:

instructing a person to carry out certain movements while being coupled to a spatial manipulator; and instructing said spatial manipulator to guide said person to perform an incorrect motion.

Optionally, the method comprises defining a rotational or translational mapping between said movements and said incorrect movements.

In an exemplary embodiment of the invention, the method comprises measuring a cortical response to said person detecting said incorrect motion.

There is also provided in accordance with an exemplary embodiment of the invention, a method of ensuring mental imagery, comprising:

providing instructions to a patient to guide a mental imagery thereof;

measuring movement of a patient in response to said imagery;

comparing said instruction to said motion; and providing feedback to said patient regarding said imagery.

Optionally, the method comprises measuring brain activity corresponding to said imagery.

Optionally, the method comprises comparing said brain activity to brain activity collected during said motion.

In an exemplary embodiment of the invention, the method comprises changing said instruction to prevent habitation of said patient.

In an exemplary embodiment of the invention, said instructions comprises instructions while said patient has closed eyes.

BRIEF DESCRIPTION OF THE FIGURES

Particular embodiments of the invention will be described with reference to the following description of exemplary embodiments in conjunction with the figures, wherein identical structures, elements or parts which appear in more than one figure are optionally labeled with a same or similar number in all the figures in which they appear, in which.

DETAILED DESCRIPTION OF EXEMPLARY EMBODIMENTS

Overview

Many embodiments of the present invention focus on methods of rehabilitation. First, an exemplary system which may be useful for the methods is described and then various methods and methodologies are described. In an exemplary embodiment of the invention, the methods and/or methodologies are implemented as software on a rehabilitation system. In some embodiments however, the methods may be partly manual and/or implemented in a distributed manner.

Exemplary System

Figure 6A:
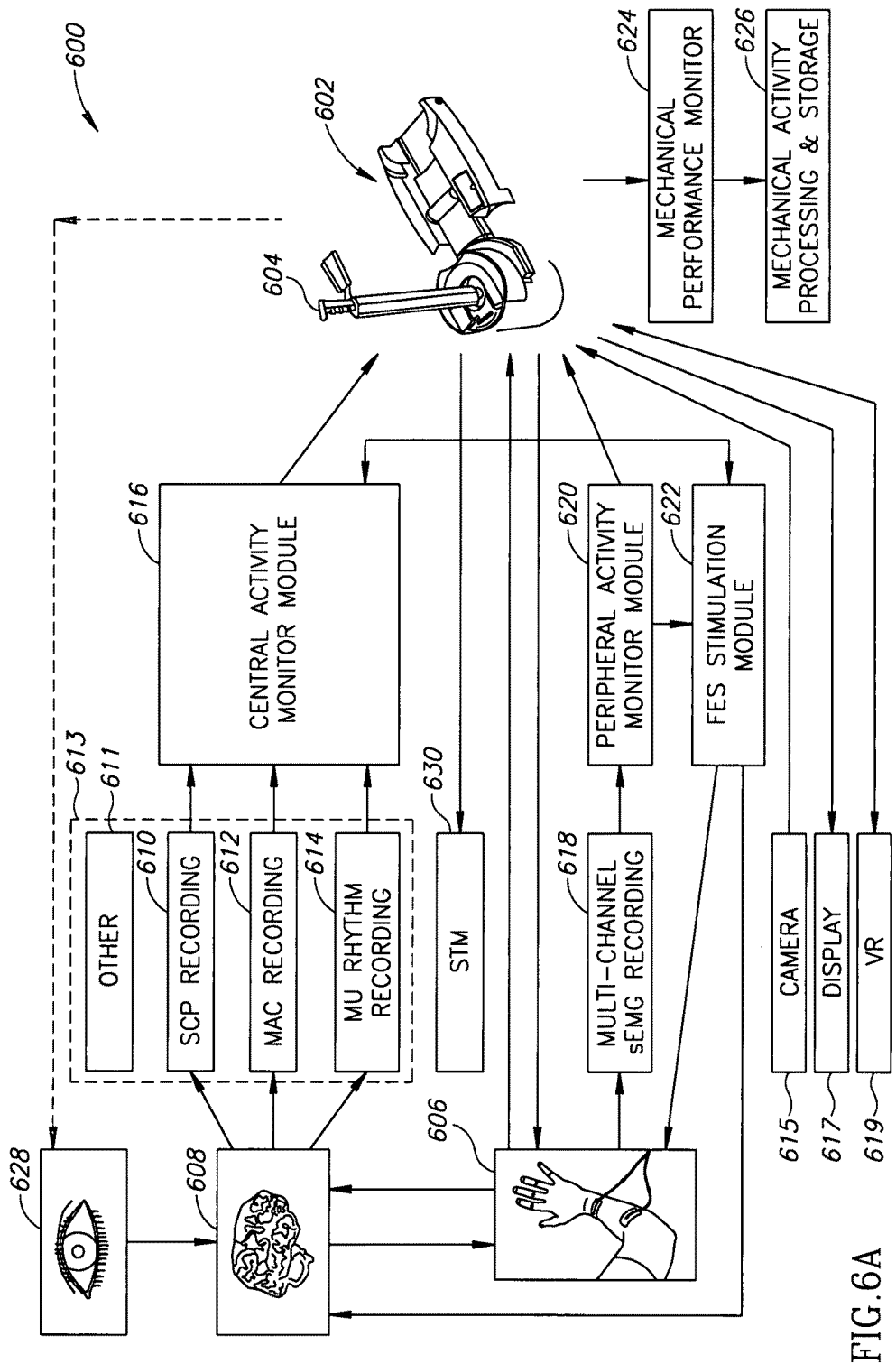
FIG. 6A shows an exemplary rehabilitation system in accordance with an exemplary embodiment of the invention.

FIG. 6A shows an exemplary rehabilitation system/device 600 in accordance with an exemplary embodiment of the invention. System 600 includes a robotic actuator or other actuator device 602 which includes a limb manipulator 604, for example, for moving an upper limb 606. Manipulator 604 optionally manipulates only a single point on a limb. In other embodiments, multiple limbs (or other body parts) and/or multiple points on a limb (e.g., joints) are manipulated. Alternatively or additionally to manipulation, manipulator 604 is used to measure movement of a limb and/or provide kinesthetic feedback to a user. Patent applications which describe exemplary such manipulators are provided below. Optionally, the manipulator comprises an articulated arm or other robotic affector.

In some methodologies in accordance with exemplary embodiments of the invention, work is performed (e.g., by attachment to system 600) on a single arm at a time; sometimes both arms are exercised together in a mirror-like fashion and sometimes the arms are exercised alternatively one after the other.

A particular intention of some embodiments of the invention is to interact with the cerebral aspects of rehabilitation, as they relate, for example, to the plasticity and/or training of a brain 608. In an exemplary embodiment of the invention, brain 608 is damaged due to traumatic brain injury or a stroke. There may also be physical disabilities, for example arthritis (or damage otherwise unrelated to injury) or orthopedic damage (e.g., related to injury). In some cases, rehabilitation is limited by physical disability and/or is modified so that the patient learns motion control that is appropriate for his physical limitations (e.g., using a cane or walker may suggest different cognitive goals than regular walking, for example, with regard to response time).

In some exemplary embodiments of the invention, various measurements 613 of brain function, for example, SCP 610, MAC 612 and/or Mu rhythm 614 are collected. Other measurements, for example, physiological measurements 611 may be collected as well. A controller and/or software module 616 is used to process and/or monitor central (brain) activity. In various configurations this and/or other modules may be separate, local, remote and/or implemented in various manners, such as hardware and/or software, centralized and/or distributed. In an exemplary embodiment of the invention, the controller includes a memory with rehabilitation information and/or programming thereon. Optionally, the rehabilitation information includes one or more of: a diagnosis, a rehabilitation plan, progress reports, rehabilitation mile stones, templates of expected progress, diagnosis templates, exercise plans (e.g., motion parameters) and/or recordings of sessions.

Alternatively or additionally to surface EEG measurements, other measurement means may be used, for example, fMRI, high resolution EEG, Hemato Encephalography (HEG), evoked potentials, implanted electrodes (wired or wireless), PET scanning, NM imaging and/or other brain and/or functional imaging and/or measurement methods known in the art. In an exemplary embodiment of the invention, multiple brain measurement methods are used, for example, EEG for during exercises and fMRI periodically, for example to assess improvement and/or to correlate with the EEG. In some cases, even expensive imaging methods, like fMRI may be used during a rehabilitation session, for example, to assess plasticity. In addition it should be noted that brain measurement serves different purposes in different embodiments, for example, in some embodiments, brain measurement is used to determine when an intention to act exists (which may require a high temporal resolution), in some whether changes in general activation levels are found (which may benefit from higher spatial resolution) and/or in others, for assessing an on-going change in ability.

Optionally, measurement of EMG is performed, for example using a multi-channel sEMG recording device 618, on a healthy and/or paretic limb. A monitor/module 620 is optionally provided for monitoring the recordings. In an exemplary embodiment of the invention, sEMG recordings are correlated with brain measurement signals and/or mechanical output of the patient.

Optionally, a functional stimulator 622 is provided, to provide sub-threshold and/or above threshold stimulation of muscles and/or nerves, in association with sEMG measurement and/or other rehabilitation procedures. In an exemplary embodiment of the invention, the stimulation is provided as a sequence of stimulations of one or more muscle groups, for example in synchronization to a time clock or in response (e.g., and/or delay) to a trigger. Optionally, the stimulation is electrical or magnetic stimulation.

In an exemplary embodiment of the invention, one or more implanted stimulators (wired or wireless) is used. Optionally, such stimulators are used for measuring EMG in addition or instead of being used for stimulation.

Wireless implantable electronic stimulators have been described, for example in: U.S. Pat. Nos. 5,193,539, 5,193,540, 5,312,439, 5,324,316, 5,405,367, PCT Publication WO 98/37926, PCT WO 98/43700, PCT Publication, WO 98/43701 Oct. 8, 1998, U.S. Pat. No. 6,051,017, U.S. application Ser. No. 09/077,662 and in an article "Micromodular Implants to Provide Electrical Stimulation of Paralyzed Muscles and Limbs", by Cameron, et al., published in IEEE Transactions on Biomedical Engineering, Vol. 44, No. 9, pages 781-790. The disclosures of all of these references are incorporated herein by reference.

In an exemplary embodiment of the invention, a mechanical performance monitor module/software 624 is provided, for example, for assessing quality of motion and/or other motion parameters. Optionally, the actual motion is compared to planned motion.

Optionally, a camera 615 is provided. A camera may be used, for example, to provide feedback to a patient, to acquire and capture images which can be analyzed to determine quality of motion, for assisting interaction with a remote or a local therapist (who has only one pair of eyes) and/or to generate cuing movies for indicating motions to a patient. In some embodiments of the invention a camera and/or a position sensor are used to detect patient motion instead of using a manipulator.

A central controller (not specifically shown outside of device 602) is optionally used for planning, monitoring and/or providing some or all of the functions described above. Feedback to a user is optionally provided, for example as a visual display (628) or as audio and/or tactile feedback. Optionally, music (e.g., rhythmic sounds) is used for feedback and/or guiding the patient and/or therapist. A mechanical processing and storage module 626 is optionally provided as a separate module or as a portion of the central controller.

Optionally, a triggering facility is provided, for example being used for summation and/or averaging of signals. This is optionally used to filter noise and increase signal/noise ratio (for example to provide synchronized evoked potentials or to measure complex signal in response to a structured behavioral algorithm as in Contingent Negative Variation (CNV)).

Optionally, the mechanical ability of actuator 602 is used to ensure repeatability between measurements.

Optionally, a brain stimulation tool (STM) 630 is provided, for example, utilizing one or more of implanted electrodes, external electrodes, drugs, targeted drug delivery and/or magnetic or heat stimulation. Optionally, selective activation of brain areas in conjunction with timed (optionally automatic and/or triggered) delivery of drugs is used to enhance delivery of drugs to active areas. Optionally, a persons' ability to control SCP (described below) is made use of for various applications, for example, activating (or deactivating) areas of interest in the cortex. Optionally, STM 630 is used in conjunction with activation caused by rehabilitation activities and/or patient control. Optionally, such conjunction is used for timing and/or parameter control of one or more of stimulation, drug provision and rehabilitation exercises.

In an exemplary embodiment of the invention, targeted activation (e.g., using stimulators, rehabilitation and/or patient control) of brain areas is used for other types of therapy, such as enhancing effect of drugs in the active area (by virtue of its being active or by virtue of increased blood flow) and guiding the integration of implanted tissue, for example, implanted stem cells or allograft tissue. Optionally, guiding of growth of existing nerve cells is targeted using methods described herein.

Optionally, device 600 includes a means, such as circuitry for timing a provision of the drugs to the activation.

Optionally, a therapist display 617 is provided, for example for showing instruction and/or feedback to a therapist. This display may be remote, for example.

Optionally, a virtual reality (VR) system 619 is provided, for example including one or more of visual goggles, a panoramic display, 3D sound, tactile sensors and/or tactile feedback. Optionally, the VR system is used to better emulate real-world situations a patient is to be rehabilitated for. Optionally, the VR system is used to enhance reality, for example by showing a desired motion overlaid on a view of the patient showing his limbs actually moving. Optionally, a standard display is used, in which a captured video stream is enhanced.

In an exemplary embodiment of the invention, the therapy is provided to a patient using virtual reality as a tool for interacting with the patient. Optionally, a test is made to determine which virtual reality setting has a most calming effect on a patient or otherwise interacts favorably with the rehabilitation process. Optionally, EEG or other brain measurements are used to determine the effect on the patient.

A device utilizing robot manipulation with MAC and methodology is optionally applied in various different ways depending on the degree of paresis and the purpose of the exercise.

The complexity of motion may vary. For example, sometimes a single movement is repeated again and again and in others, two or more movements (or a more complex schedule) is repeated. In some cases a schedule is established, for example, an "easy" movement is followed by a "difficult" one to encourage further plasticity after some rehabilitation gain has been established.

In an exemplary embodiment of the invention, system 600 is used as a specific motion inducement trainer. Instead of conventional "Constrained Induced Therapy" for hemi paresis, system 600 can be used as a dynamic alternative by facilitating schedules programmed by the professional therapist with a deep knowledge of the particular neurological limitations of the patient. Relevant trajectories with a particular level of resistance are optionally encouraged or allowed.

In an exemplary embodiment of the invention, system 600 is used to provide a personalized level of training. Optionally, a positive feedback loop is established between the mechanical and neurological modules of system 600 so that the degree of complexity of the movements exercised by the former matches the performance recorded by the later. For example, the higher the recorded central activation the bigger the force needed to move manipulator 604 over a very well known movement loop. This type of feature can provide improvements during the later stages of the rehabilitation process, when progress can be most difficult. This type of interaction may allow the patient to "specialize" in certain parts of the movement while being less challenged during parts over which the patient does not have enough control. In an exemplary embodiment of the invention, this type of feedback allows a patient to be treated according to his therapeutic level. In an exemplary embodiment of the invention, the system assists a user in initiating a motion (e.g., by continuing it once started) or in completing a motion (e.g., by stopping at the end, optionally with a gradual slow-down). Optionally, measurement of the ability of the patient to initiate, carry-through and/or stop a motion are used as indicators of rehabilitation progression.

In an exemplary embodiment of the invention, movement comprises one or more of passive active and intermediate and other movement types. A list of particular exemplary motions is described further below. It is noted that in some cases, certain movements may not be appropriate, for example a paretic patient who is totally immobile cannot be expected to move against resistance.

Optionally, music and/or rhythmic sounds are used as part of the rehabilitation process. In an exemplary embodiment of the invention, integrated uses of music rhythm and lighting are used to enhance feedback linkage and/or to add an entertainment dimension to the rehabilitation process. For example, bongo tapping is a generally uplifting activity. It is possible that this may be due to the rhythmic hypnotic reward provided by the sound linked to the repetitive coordinated movement. In an exemplary embodiment of the invention, it is considered that multi-sensorial linked performance tends to promote physiological and cortical coherence and system 600 is used to promote such coherence by providing multiple feedback modes and/or activation in a rhythmic manner which may assist in rehabilitation.

Previous Patent Applications

The following is a table of patent applications sharing applicants and/or inventors with the present application and which provide various apparatus and methods possibly helpful for carrying out embodiments of the present invention.

| Title | Serial_# | Filing Date | Exemplary contents |
|---|---|---|---|
| Methods and Apparatus for Rehabilitation and Training | PCT/IL2005/000142 | Feb. 04, 2005 | Describes various methods and apparatus for rehabilitation, including manipulators and methods of taking motivation into account. |

-continued

| Title | Serial_# | Filing Date | Exemplary contents |
|---|---|---|---|
| Methods and Apparatuses for Rehabilitation Exercise and Training | PCT/IL2005/000136 | Feb. 04, 2005 | Describes method and apparatus for rehabilitating while sitting and/or rehabilitating balance and coordinated movements. |
| Gait Rehabilitation Methods and Apparatuses | PCT/IL2005/000138 | Feb. 04, 2005 | Describes method and apparatus for rehabilitating gait and other multi-joint and/or coordinated movements. |
| Rehabilitation with Music | PCT/IL2005/000137 | Feb. 04, 2005 | Describes using music as feedback and for guiding rehabilitation. |
| Neuromuscular Stimulation | PCT/IL2005/000135 | Feb. 04, 2005 | Describes using sEMG and FES as part of a rehabilitation process. |
| Fine Motor Control Rehabilitation | PCT/IL2005/000139 | Feb. 04, 2005 | Describes devices and methods for rehabilitating fine motor control, such as writing. |
| Neuromuscular Stimulation | PCT/IL2005/000442 | Apr. 28, 2005 | Describes methods and apparatus for rehabilitating using implanted wireless electrodes. |
| Motor Training with Brain Plasticity | 60/686,991 | Jun. 02, 2005 | Describes methods and apparatus that relate to rehabilitation while monitoring a brain |
| Device and Method for Training, Rehabilitation and/or Support | 60/665,886 | Mar. 28, 2005 | Describes rehabilitation and/or support devices suitable for persons of limited mobility |
| Apparatuses for Retrofitting Exercise Equipment and Methods for Using Same | 60/666,136 | Mar. 29, 2005 | Describes retrofitting exercise device for use in rehabilitation |
| Methods and Apparatuses for Rehabilitation and Training | US filing. Attorney docket 414/04572 | Aug. 18, 2005 | Describes methods and apparatus for rehabilitation |

The disclosure of all of these applications are incorporated herein by reference. In general, the techniques and apparatus in these patent applications can be used for providing rehabilitation of various body parts and/or feedback and/or be used in conjunction with cerebral monitoring as described herein.

Overview and Exemplary Uses of System 600

There are many ways in which a system such as system 600 can be used for rehabilitation in conjunction with cognitive rehabilitation and/or cognitive assessment. The following provides a sampling of such uses, with some particular exemplary uses being described after with exemplary protocols of application.

A first group of uses relates to robot-assisted rehabilitation which utilizes EEG or other assessment of brain activity. In an exemplary embodiment of the invention, the assessment is used to induce and/or measure brain plasticity. In an exemplary embodiment of the invention, brain and manipulator function are correlated or interact, for example, using one to trigger or generate the other.

In an exemplary embodiment of the invention, measurements of brain activity are used to provide feedback to one or more of patient, system and/or therapist, for example, during an exercise, during a session and/or between sessions. In an exemplary embodiment of the invention, the cortical effect of a rehabilitation exercise is thus assessed and/or optionally correlated with physical effect of the rehabilitation. This may be used to identify problems in the rehabilitation process and/or patient limitations. In an exemplary embodiment of the invention, the feedback is used for more cortically specific rehabilitation, in which rehabilitation exercises and/or parameters are used to selectively focus on certain brain areas and/or restructuring methodologies. Optionally, an exercise is used if it shows a desired selective, cortical and/or restructuring effect. The exercise is optionally dropped, reduced in importance or its parameters changed, if a desired effect is not found. It is noted that a particular benefit of intra-session analysis is a fast response to patient needs. Optionally, feedback that changes an exercise is provided in less than 30 minutes, less than 10 minutes, less than 5 minutes, less than one minute, less than 30 seconds or smaller or intermediate times.

In an exemplary embodiment of the invention, the rehabilitation is used to effect an improvement effect on motion and/or on a desire to carry out a motion.

In one exemplary embodiment of the invention, the bilateral Readiness Potential is monitored, quantified and/or displayed prior to a precise movement path (e.g., provided by a robot), in order to induce, monitor, entrain and/or assess plastic changes in the brain.

In an exemplary embodiment of the invention, rehabilitation is based on the assumption that when there is a temporal and/or physiological linkage between the planning of a movement, the subsequent execution of that movement by a paretic arm, the kinesthetic perception of such a movement via sensorial fibers that may be intact, the actual witnessing of the movement taking place at a physiologically expected time after the resolution to start it, and/or the possibility to accurately return to all the above steps repeatedly with the help of a specialized physiologically based rehabilitation manipulator on the one hand and/or the possibility of enhanced and facilitated positive plastic change on the other hand. Not all these items need be correlated in order to have a beneficial effect. In an exemplary embodiment of the invention, an accuracy required of the patient during a rehabilitation session (e.g., to define matching) is selected to be suitable for the task. For example, an accuracy and/or repeatability of better than 5 cm, 3 cm, 1 cm, 0.5 cm or better may be required for different tasks.

In an exemplary embodiment of the invention, a robotic manipulator, for example an apparatus as described in U.S. provisional application 60/542,022, the disclosure of which is incorporated herein by reference, is used. This apparatus can include an optional display, an optional processor, an optional user input and a robotic manipulation portion or a resistive portion. In some embodiments described therein, the device can be configured for one or more of causing a set motion, resisting motion, copying motion between limbs (e.g., hands, arms, feet or legs), assisting motion of a limb and performing motion of multiple joints. In addition, such a manipulator can also measure limb positions and forces or these can be measured in other ways. The use of a processor and an input can allow more detailed programming. In an exemplary embodiment of the invention, the programming includes exact repetition and processing of physiological signals in a manner that matches the repetition.

While a robotic manipulator is not strictly required, a potential advantage of some such manipulators is the ability of the manipulator to measure, repeat and modify in a very controlled way a wide range of movements. Controlled features of the robot optionally include one or more of kinetic, positional and temporal variables such as path, velocity strength acceleration, repetition rate and/or synchronization to brain rhythms.

Various methods are optionally used to assess brain function, for example, one or more of fMRI, EEG, HEG, implanted electrodes and other methods known in the art. Optionally, a lower cost method such as EEG is used during rehabilitation, even though its resolution may be lower. Optionally, calibration is carried out, for example at a start of rehabilitation and/or periodically, to generate a correspondence between a high resolution method and a low resolution method. In one example, an fMRI is calibrated to EEG, by the patient being instructed (e.g., by a therapist and/or an apparatus) until a desired motion or cognitive effect is achieved. That a correct or known effect is achieved may be determined by the fMRI system. During rehabilitation it may be assumed that if a corresponding EEG signal is achieved, this means that the underlying cognitive effect as viewed on the fMRI signal is also being achieved, at least in approximation. Optionally, calibration is repeated when a new effect is being trained or if it is felt that the EEG (or other lower quality signal) is not generating a correct indication.

In an exemplary embodiment of the invention, the method used for measuring brain activity is a nIR Mass Spectrometry or Spectrophotometry, a non invasive non-contact method of monitoring Oxygen levels (e.g., Oxy-Deoxy Hemoglobin) or other metabolic and/or functional markers at brain cortex via optical means. In an exemplary embodiment of the invention, nIR Mass Spectrometry sensors (optionally based in "optodes") are positioned over the motor cortex (or other parts of the scalp or inside the skull) and compare normal with paretic side signals while the patient performs exercises. An article describing such a system is "On-line optical imaging of the human brain with 160-ms temporal resolution" by Maria Angela Franceschini et al. 31 Jan. 2000/Vol. 6, No. 3/OPTICS EXPRESS 49, the disclosure of which is incorporated herein by reference.

In an exemplary embodiment of the invention, use is made of a correlation between periodicy in brain function and periodicy in motor control. In an exemplary embodiment of the invention, a task is provided which has an intrinsic frequency. This frequency is used as a filter for filtering EEG signals for better detecting signal sources and/or characteristics. Alternatively or additionally, the rhythm in the brain is detected and a motor activity is modified to match that rhythm. Optionally, a test is made to determine, for that particular patient, which brain rhythms are easier to maintain. Optionally, a plasticity measure of brain function is derived from the ease in which a brain rhythm is changed by changing an underlying task. It is expected that a less plastic brain will be able to follow such changes more slowly and/or fail in an exercise faster than a more plastic brain.

Additional apparatus useful in the practice of the invention is described in U.S. provisional application 60/566,078, the disclosure of which is incorporated herein by reference, in which EMG measurement in a healthy limb is used for controlling the rehabilitation and/or stimulation of an unhealthy limb. There are optionally four EMG channels, one channel measuring EMG signals from each of four muscles: the biceps, the triceps, the flexors, and the extensors. Each channel uses three electrodes, two recording signals from near each end of the muscle, and one reference electrode in the middle. In that application, a low level signal based on the measured EMG in the healthy limb was applied to the paretic limb, to assist in motion, to provide feedback to the patient and/or to provide encouragement.

In an exemplary embodiment of the invention, the capabilities of a robot manipulator for movement planning, programming, precise repetition, and/or an optional high degree of synchronization with the MAC monitoring, allow for complete or more complete control over one or more important factors relating with rehabilitation.

In an exemplary embodiment of the invention, rehabilitation is based on the assumption that a common characteristic of endogenous components (based on an internal assessment process) is the dependence on attention. Whereas exogenous components tend to persist under varying degrees of attentiveness towards the event, an endogenous event is often augmented under increased attention or extinguished in the presence of distracting stimuli. Optionally, a measurement of the depth of CNV or BP can reflect the attentive strength during rehabilitation.

In an exemplary embodiment of the invention, the apparatus provides various repetitive synchronized schedules of motion, which are used to monitor and/or improve cortical activation associated with the motion.

In an exemplary embodiment of the invention, the apparatus is used to quantify and/or assess progress of cortical activation skill for example as associated with a repeatable movement schedule.

In an exemplary embodiment of the invention, the apparatus is used to generally activate cortical networks previously dormant.

In an exemplary embodiment of the invention, the apparatus is used to promote synchronization between cortical activation and its associated peripheral result, possibly reconciling motor output with sensory feedback.

In an exemplary embodiment of the invention, the apparatus is used to assess rehabilitation progress as practically related to improvement in cortical activation and, (possibly indirectly), plastic redistribution and progress.

In an exemplary embodiment of the invention, one or more different types of motion (e.g., Free, Synchronized, Syncopated) are tried with a patient and their relative effectiveness for rehabilitation (e.g., on the basis of the degree of cortical activation related with each one of them), are estimated. Optionally, the rate of progression in synchronization of activation and/or in other parameters of cortical activities (e.g., as compared to healthy subjects or motion of healthy limbs), is used to estimate rehabilitation time and/or expected milestones.

In an exemplary embodiment of the invention, one or more templates of progression of cortical activity and/or their association with physical rehabilitation are stored and compared to actual progress of a patient. Optionally, a classification of the rehabilitation type is provided based on the type of progress and/or interaction between robot manipulation and cortical activity. Such classification can be a sub-classification of a basic classification based on brain damage. Optionally, the templates are generated as plans for a patient.

In an exemplary embodiment of the invention, the detection of repeated signals is used to indicate that a correct brain activity is taking place.

In an exemplary embodiment of the invention, an apparatus is used for providing multiple ways of activating a motor pathway, including one or more of: from higher brain centers (planning), from lower brain centers (feedback of forced motion) and/or from lateral brain center (copying of motion of laterally opposite limb). In an exemplary embodiment of the invention, such multiple ways of activating may serve to assist a patient in overcoming a disability and/or discovering alternative pathways.

In an exemplary embodiment of the invention, rehabilitation is carried out based on the assumption that when there is a temporal and physiological linkage between the planning of a movement (BP), the subsequent execution of that movement by a paretic arm (even when such a movement is largely or completely generated artificially, e.g. using a robot or by the sEMGs of muscles of the contra-lateral arm), the kinesthetic perception of such a movement via sensorial fibers that may be intact, the actual witnessing of the movement taking place at the physiologically expected time after the resolution to start it, and/or the possibility to accurately return to all the above steps repeatedly (e.g., with a robotic manipulator); the possibility of positive plastic change to recover mobility is facilitated and/or enhanced. Alternatively or additionally, the above is used for testing and/or assessment.

In an exemplary embodiment of the invention, rehabilitation is carried out based on the assumption that that combined peripheral nerve and brain stimulation ("dual stimulation") induces changes, for example of excitability of normal motor cortex. Alternatively or additionally, rehabilitation is carried out based on the assumption that "dual stimulation" induces motor cortex plasticity and associated functional improvements. Some basis for this may be found in (Uy J, Ridding M C, Hillier S, Thompson P D, Miles T S.: "Does induction of plastic change in motor cortex improve leg function after stroke?" Neurology. 2003 Oct. 14; 61(7):982-4.), the disclosure of which is incorporated herein by reference.

In an exemplary embodiment of the invention, a robot manipulator provides a cuing structure (e.g., controlled vibrator) to mimic the syncopate condition described above.

In an exemplary embodiment of the invention, readiness is assessed. In an exemplary embodiment of the invention, a patient uses a manual input to indicate readiness for an exercise (e.g., that planning is completed). In an alternative embodiment, brain activity analysis is used for such assessment. In one example, imposed motion is applied at a time when the patient is ready for it. In one example, brain signal processing indicates such readiness, as described in the background. In another example, various delays relative to such calculated readiness are tried out for a patient and/or for various types of motion. In another example, brain signal analysis is used to assess when the patient's attention is properly focused. Optionally, such analysis is used as feedback for training the patient in improving his attention and/or to assist a patient in detecting when such attention is lacking.

In an exemplary embodiment of the invention, in addition to or instead of contra lateral stimulation of muscles in a paretic arm, MAC slow waves recorded as a result of well defined movement procedure (e.g., organized and delivered by a robot manipulator) are optionally used as markers of attention and optionally as used to indicate or generated to act as promoters of plasticity and/or rehabilitation.

In an exemplary embodiment of the invention, intent is promoted and/or measured. In an exemplary embodiment of the invention, recording central activation (e.g., SCP, MAC) in sync with external movement gives a qualitative and/or quantitative assessment of degree of "intention" to perform a particular movement by the patient, which intention measure may be used to promote plasticity and rehabilitation, for example, by taking the existence of an intention as a starting point to actually carry out motion, as described in more detail below. Optionally, the assessment is carried out even when there is no muscular contraction externalization. This is optionally accomplished by measuring (a) residual EMG without contraction; (b) brain activation over contra-lateral somato-motor cortex; (c) general cortical activation as measured by central slow cortical potential; and/or (d) comparing slow cortical bilateral activation of paretic and normal side.

In an exemplary embodiment of the invention, "intention related signals" are rewarded (e.g., used for promotion), for example, by stimulating, as a response, the desired muscle on the paretic side through FES. In an exemplary embodiment of the invention, the amplitude of generalized brain activation is used to promote increasing FES stimulation of the paretic muscle. Possibly, through repetition of the same stimulation and response the brain "realizes" the link between a particular type of brain activation of an area previously lethargic and the precise peripheral motor activity induced by the system. Returning to the same linkage repeatedly may result in more plasticity.

In an exemplary embodiment of the invention, encouragement is provided during rehabilitation, for example, indicating one or both of correct (or progressive) brain activity and motion. Optionally, provision of a power boost to an existing weak motion and/or augmenting positional feedback and/or reducing the complexity of motion can be used to encourage a patient additionally or alternatively to them being used to assist in the cognitive aspects of rehabilitation.

In an exemplary embodiment of the invention, cortical signal movement signatures are used. In an exemplary embodiment of the invention, the cortical signals of a population of "movement professionals" such as dancers or Tai Chi practitioners is measured, for example using a manipulator in association with neural electrodes and/or imaging. Optionally, the manipulator is used to measure force information and/or measure behavior when encountering resistance and/or spatial asymmetry (e.g., standing crooked). Optionally, a patient is trained to generate matching signals (e.g., using methods as described herein) or the signals are used as triggers for applying FES to the patient. Alternatively to movement professionals, a signature of the patient himself (e.g., from before brain damage or from healthy limb) are used.

A set of uses of some embodiments of the invention relates to using a robotic manipulation system (e.g., active or passive) for diagnosis. In an exemplary embodiment of the invention, the system is used to perform different manipulations and/or complexity levels in a way which will (should) either cause expected brain activation patterns or require the use of certain brain areas. For example, asking a patient to repeat a complex motion exemplified by the system will activate brain areas differently from asking a patient to maintain a constant velocity of motion in a circle under a condition of varying resistance. In another example, more complex motions may require a greater planning effort.

In an exemplary embodiment of the invention, a robotic system is used in assessment of plasticity and/or progress and/or efficacy of a rehabilitation treatment. In an exemplary embodiment of the invention, the system provides a same set of repeated exercises, for example, repeated during a same session (to assess intra-session improvement and provide one measure of brain plasticity, based on improvement in one or more of cortical activity and/or motor ability) or in different sessions (to assess progress between sessions).

It should be noted that a controlled system can optionally control one or more of: the required motion, measurement of variations, timing, graduated changes and/or provide variations in order of exercises. Some of these features may be available using manual methods. However, it is believed that in many cases there is too large a variability to allow purely manual application of testing exercise to be as effective as machine applied and machine assisted exercises. Optionally, a machine can provide repeatability to within better than 10%, 5%, 1% or intermediate or better values for desired timing, position and/or forces, as compared to the actual carried out action. Optionally, improvement of central recordings (for example MAC) over a pre-established and repeatable movement loop are recorded and quantified as an indirect qualitative assessment of plastic enhancement. In some embodiments of the invention, rehabilitation is based on the assumption that repetition of defective movements brings about plastic enhancement, which is thus practiced, e.g., a patient is asked to repeat the best motion he is capable of to enhance plasticity instead of requiring improved quality towards a goal. Optionally, the plasticity is assessed during such repetition to determine its effectiveness and/or decide how long to continue. Optionally, instead of directly measuring plasticity, a negative measurement is made, in which what is looked for is a lack of plasticity which was expected. For example, assuming 100 repetitions will induce plasticity and measuring once a week or less often to see if there were plasticity changes (e.g., by brain imaging), can be used as a method to track plasticity.

Optionally, temporal linkage between cortical activity and machine generated movement may also enhance plasticity in a different way (similar but possibly better than using a mirror image technique). Here the actual movement of the paretic arm when expected by the brain, (activated by intention and audiovisual stimuli from the system) may provide an especially significant synchronized sensorial input that induces and catalyzes regaining of movement.

Optionally, by recording physiological signals and assessing movement improvement of many individuals over long periods of time the system supports the comparing of intra- and inter-personal performance by relating the performance of patients and comparing patient results to a suitably related population of plasticity "signatures". Optionally, this comparison can be independent of the patient actual condition, for example, independent of where the damage is in the brain. Alternatively, when the comparison is indexed to a damaged area and/or extent in the brain, such a measure helps show the basic plasticity of the brain and/or possibly underlying motivational and/or cognitive problems.

In an exemplary embodiment of the invention, the effectiveness of rehabilitation is assessed by detecting one or both of enhanced activity in one hemisphere when motion typically related to the other hemisphere is carried out, or by increased activity in a damaged hemisphere.

In an exemplary embodiment of the invention, brain activity is monitored to determine if a physical rehabilitation activity is having a desired effect in the brain. In an exemplary embodiment of the invention, the brain measurements are used as feedback to a patient (or a therapist or a controller) to indicate if the patient is applying a correct concentration or directed effort. Failure by the patient may suggest the use of other exercises. In one example, if it is clear that the patient is expending effort on a wrong activity, a new exercise where the wrong activity is minimized (e.g., power boosting of motions) may be provided. In another example, complex exercises may be simplified to the point where a patient is able to achieve correct (or progressing) brain activation.

In an exemplary embodiment of the invention, monitoring of brain activity is used to detect restoration of a correct balancing of brain activation. In some cases, such balancing is not possible due to organic damage. However, an expected degree of balancing (e.g., based on an assessment of damaged tissue) can be aimed for. In other cases, a similar activation across a range of exercises is a target.

In an exemplary embodiment of the invention, the characteristics of the movement, (for instance free, synchronized or syncopated) and/or the presence or absence of a pre-warning cue, (promoting a CNV type of response), may determine the degree of contra-lateral spread of the MAC signal over the scalp. In an exemplary embodiment of the invention, the characteristic may be selected intentionally to have a desired effect. Alternatively or additionally, the brain activity may be measured to determine if a desired effect was achieved.

In an exemplary embodiment of the invention, desired rehabilitation time and/or type are assessed. In an exemplary embodiment of the invention, a baseline is set for one or both of motion ability and cortical electrical activity. The performance of a patient is compared to one or both baselines, for example to determine a rehabilitation stage, rehabilitation block (e.g., certain brain area not progressing) and/or a progress rate. In an exemplary embodiment of the invention, the baseline is set by the same patient for a healthy limb. Alternatively or additionally, the baseline is set by a healthy person. In an exemplary embodiment of the invention, a patient is compared to progress and measurements of other patients with similar healthy brain scans (e.g., for unimpaired motion) and/or patients with similar organic damage.

In an exemplary embodiment of the invention, diagnosis is carried out by having a patient try out a same motion with a healthy and a paretic arm. As the amplitude of CNV generally reflects preparation for contra-lateral motor activity, this may provide a way to assess performance of a damaged side (in case of hemi-paretic subject). Optionally, such diagnosis is continued during rehabilitation, for example to establish and/or quantify the degree of recovery reached.

A set of uses of some embodiments of the invention relates to assisting cognitive rehabilitation using a robotic manipulation system.

In an exemplary embodiment of the invention, selective treatment of brain areas is provided. In an exemplary embodiment of the invention, a manipulation and measurement system optionally as described herein is used to identify the edge of a damaged area in the brain, so that plasticity and rehabilitation efforts may focus on that area. Optionally, such an edge area is identified by its having a ragged activation profile.

In an exemplary embodiment of the invention, local activation is provided, for example, by one or more of heating, magnetic brain stimulation, electrical stimulation and/or drug delivery. In an exemplary embodiment of the invention, selective activation of the relevant brain area is provided by cognitive feedback training of the patient to activate a brain area and then provision of a drug or other generalized treatment. Optionally, such selectively is applied before, during and/or after a physical rehabilitation exercise which addresses that area. Optionally, the timing and/or relative triggering are provided by a manipulator system which measures brain activity and/or physical activity.

In an exemplary embodiment of the invention, a manipulation device is used for providing direct cortical rehabilitation. In an exemplary embodiment of the invention, SCP signals recorded from a single point of the scalp, (for instance Cz), are used in a biofeedback fashion to teach the patient to control the negativity (cortical activation) or positivity (cortical deactivation) of the signal at that point. Once the patient is able to control the SCP signal at a single point, one feature of the signal (for instance its negativity) is optionally used to drive a manipulator in space, for example, in a mono-directional fashion in one plane. Later, after further progress of the patient, optionally, the various features of the signal are translated into a binary code used to drive the manipulator in space in a mono-directional fashion in one plane. Later after yet further progress, optionally, by measuring at various different points over the scalp, the patient is trained to control the SCP signal at each one of them simultaneously and that information is translated into binary codes used to teach the patient to drive the manipulator in space in a multidirectional fashion; optionally, first in a single plane and later in a three dimensional mode. The manipulator may be used for one or both of producing a movement as a response to the particular combination of cortical signals and/or enhance and amplifying traces of movement conquered by the patient. Optionally, the patient is selectively instructed to try and carry out motions and/or image the motions.

In an exemplary embodiment of the invention, at a later stage in rehabilitation after the patient learns to move the manipulator with his/her SCP signals, the next step is to be able to detect which of the movements is associated with the production of residual sEMG signals in relevant muscles. Then, by allowing the manipulator movement only when there is the required mixture of central (e.g., SCP or MAC) and peripheral (sEMG) measurements, the system can teach the person to integrate cortical activation and muscular performance In an exemplary embodiment of the invention, a target of the rehabilitation process is brain reorganization. Optionally, after a minimal amount of reorganization is detected, this reorganization is used to rehabilitate one or more limbs. Optionally, this "brain" rehabilitation of the limb starts even when there is little or no residual limb movement in a paretic limb.

In an exemplary embodiment of the invention, one or more cognitive activities (but optionally a limited number) are supported by a physical system. Optionally, such support allows a patient to focus his energies and/or attention on damaged brain areas, reduce fatigue and/or enable the execution of an otherwise too-complex exercise. In an exemplary embodiment of the invention, cognitive support is provided by one or more of visual feedback or anticipatory display (e.g., a 3D movie), audio feedback, kinesthetic feedback from the same or other arm (e.g., by moving the arm before the exercise or by applying an external force to aid in recognizing when the arm is off-line), providing a power boost so patient is not required to concentrate on details of carrying out and/or correcting the motion, exemplifying complex motions so less memory is needed to recall and/or understand such motions and/or assisting in overcoming pain, for example by allowing patient to feel the pain ahead of time or by reducing muscle activity of the patient and thus pain.

In an exemplary embodiment of the invention, rehabilitation is enhanced by replacing one or more brain functions by a physical manipulation system. In an exemplary embodiment of the invention, kinesthetic feedback analysis is augmented or replaced by a manipulation system providing such feedback and/or closing the correctional loop of the motion. Alternatively or additionally, other activities, such as planning are provided by the system. In an exemplary embodiment of the invention, kinesthetic feedback is provided as audio or visual feedback or using tactile feedback (e.g., vibration of vibrator patch on a limb). Optionally, such replacing is reduced as rehabilitation progresses and/or as part of a rehabilitation plan for kinesthetic sense.

A set of uses of some embodiments of the invention, relates to the use of a manipulator to improve measurement capabilities. In an exemplary embodiment of the invention, repetitive or selectively different motions by the manipulator are used to better detect brain activation and/or tease apart different sources of brain activity.

In an exemplary embodiment of the invention, repetitive specific motion is used to define a cortical signal, for example, for comparison or for deciding on treatment. In an exemplary embodiment of the invention, the fact that a repetitive manipulator is used, allows brain signals recorded over multiple trials to be combined and averaged. Optionally, the manipulator is used to trigger the movement, so that the signals can be aligned in time. Optionally, the motion includes motion of a healthy arm and of a paretic arm. The healthy arm movements are optionally detected by the manipulator and used as the above trigger.

In an exemplary embodiment of the invention, multiple motions are carried out to determine a motion which is associated with maximal central activation (e.g., of areas of the brain associated with the paretic limb). Such determined motions may be used as a starting point for rehabilitation, personalized for that patient. Optionally, a range of different motions are selected, including motions with minimum activation and motions with intermediate activations. Optionally, this allows rehabilitation to selectively attempt easy motions and hard motions, motions where fast improvement is expected and motions where slow improvement is expected. Possibly, starting with a maximal signal motion will provide significant plasticity. Optionally, the lesser signal strength motions are used to assess general progress of the patient. Optionally, weak signal motions are used to generate a map of patient ability and lack thereof.

Optionally, for a particular motion, electrode placement, configuration and/or signal processing may be varied to enhance measurement quality.

In an exemplary embodiment of the invention, a BCI interface is improved using repetitive motion. In an exemplary embodiment of the invention, by providing multiple repetitions, a better optimization of filtration algorithms and/or feature extraction algorithms can be provided. In an exemplary embodiment of the invention, this allows a better interface to be defined for prosthetic devices. In an exemplary embodiment of the invention, using a controlled manipulator allows a test to be made of the effect of small changes in signal detection on movement and vice versa. Optionally, by improving filtration and/or implanting electrodes, detection thresholds can be reduced. Optionally, coherent and pattern based signal processing techniques as known in the art of signal processing are used. Optionally, prosthesis tuning is carried out at a rehabilitation session, for example, to help train the patient in the use of the device while at the same time possibly determining more optimal BCI parameters.

In an exemplary embodiment of the invention, the number of repetitions provided for training a motion (e.g., in one or a small number of session over less than a month and optionally less than a week or less then a day, or possibly less than an hour) varies between 10 and 1000 or more, optionally more than 30, optionally more than 100.

Signals Used

Figure 2:
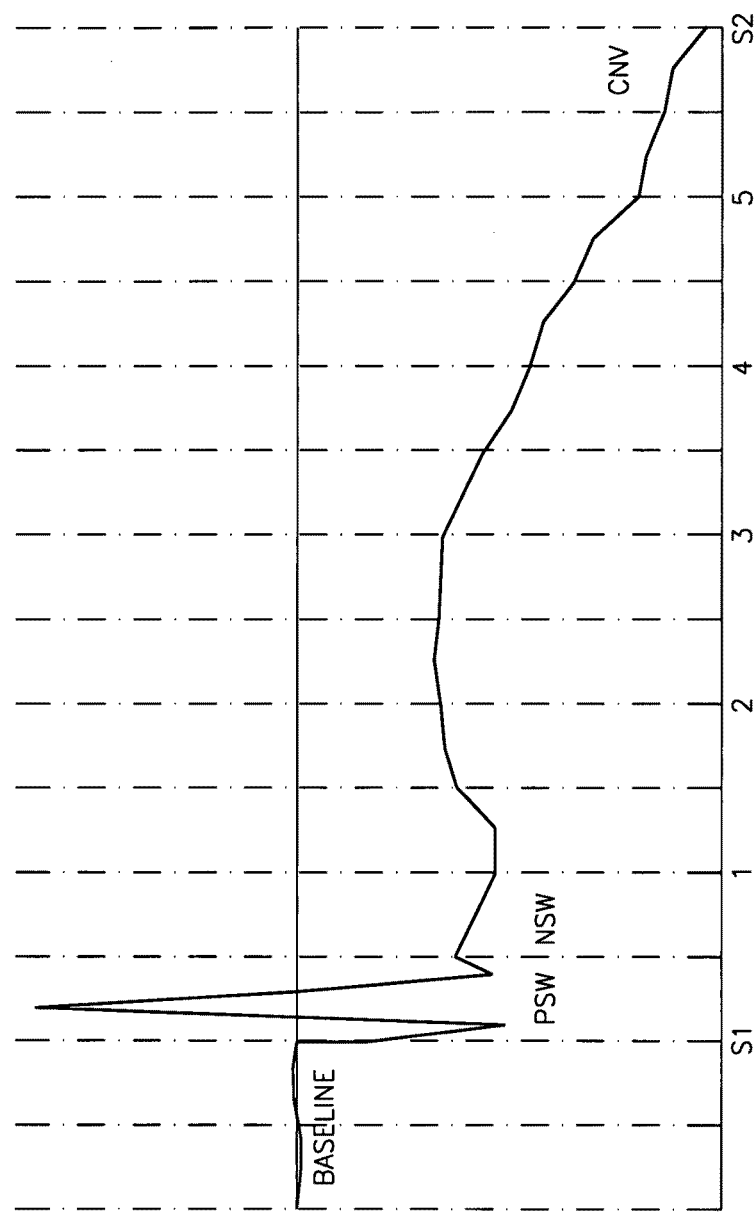
FIG. 2 shows a typical event-related potential in an S1-S2 paradigm, measured from central derivations.
Figure 3:
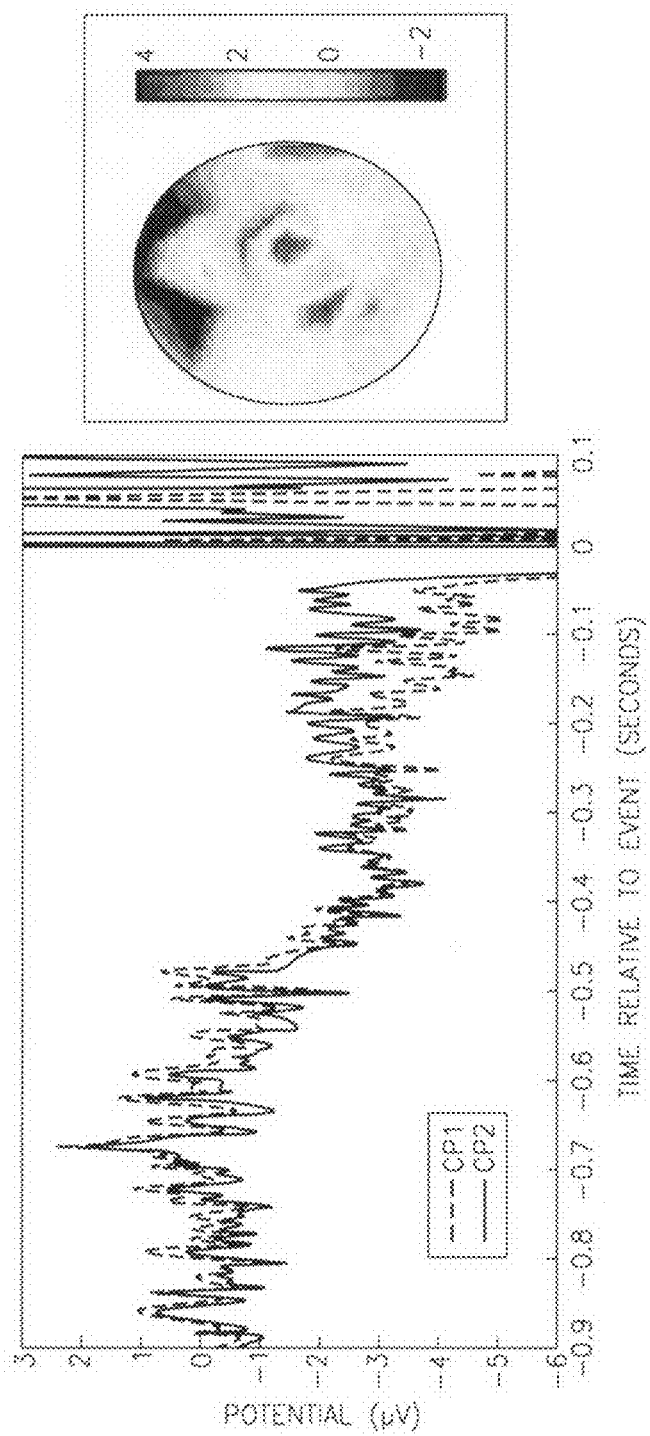
FIGS. 3-5 show temporal and topographic distributions of BP amplitudes over the entire scalp surface, for different types of motion.
Figure 4:
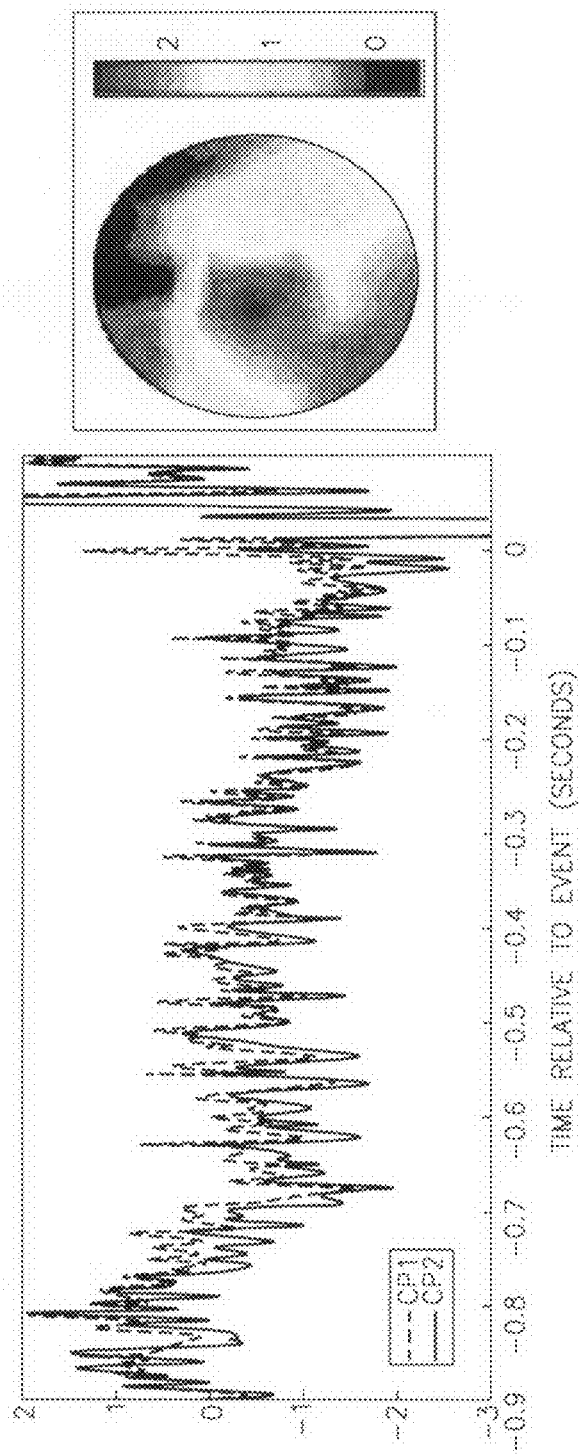
Figure 5:
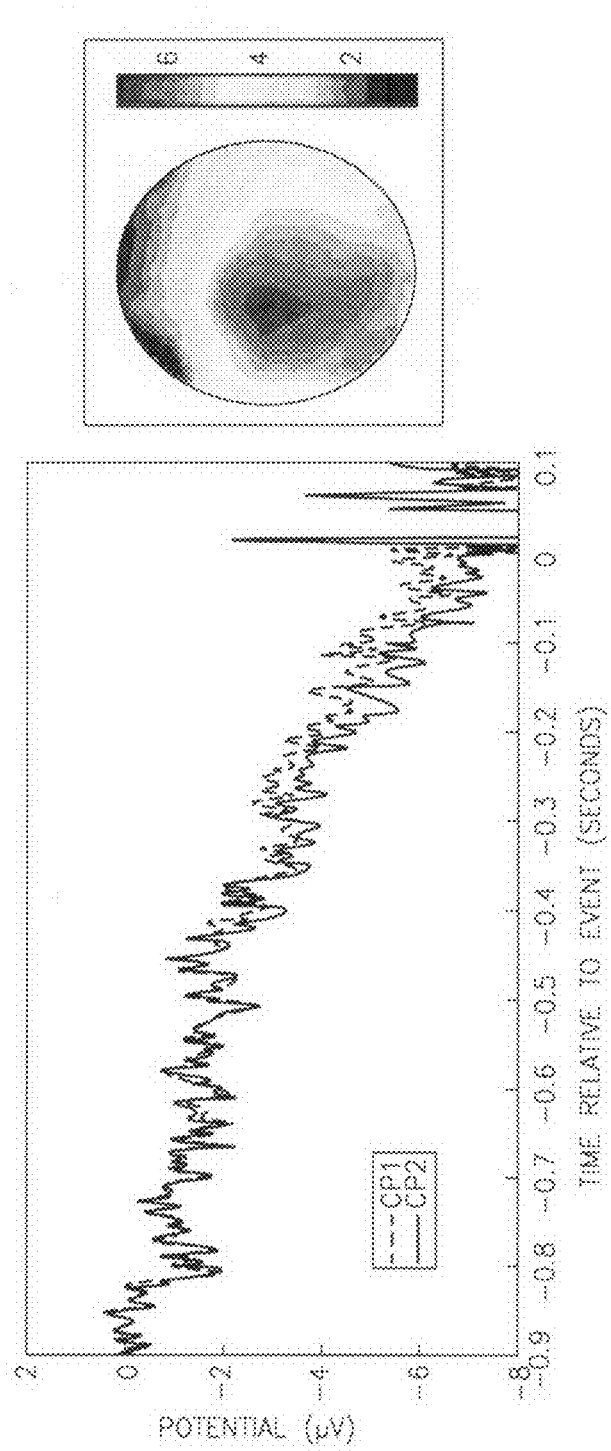

Various cortical signals may be used. In an exemplary embodiment of the invention, event-related potentials are used. Early waves include: PSW Positive slow wave potential (which appears to represent the evaluation of the stimulus: ("I hear a sound; what is it?")) and NSW Negative Slow Wave potential (which appears to represent the orientation reaction i.e. the process of deciding what to do next: ("That sound means to move my left hand"). Optionally, early waves are not used, but rather later waves are used, for example, CNV (which represents the motor response preparation that takes place after PSW and NSW) when the response to be taken after S1 is "clear": ("Let's move my left hand when S2 appears"). It should be noted that each stage is centered at a different part of the brain: PSW (Parietal) NSW (Frontal) and CNV (Central). The recording in FIG. 2 is in C3 and C4 (C3: left central area of the brain; C4 right central area of the brain; there CNV is very prominent. However, any part and/or multiple parts of event related and non-event related signals may be used. For example, attention related signals may be used, as may alpha and/or other rhythms.

In one example, BP is used. BP represents a physiological response similar in nature to CNV (brain activation as preparation to execute a motor response). However, in the case of BP, there is no neural processing/examination related to processing the nature and meaning of the stimulation. Therefore, BP typically involves mainly the activation of motor and areas in the cortex while CNV involves the activation of other sites in the brain as frontal and central cortex.

In an exemplary embodiment of the invention, CNV is particularly used when device 600 provides sound stimulation to indicate to the patient various stages of the movement loop to alert him/her that another step in a rehabilitation exercise is about to begin. This may assist in entraining the patient to perform movement in sync with pre-planned exercise. This is similar to the S1 S2 type of paradigm involving CNV.

As described above, the signals are optionally composite (scalar) signals. However, a grid array or other multi-value structure, such as a vector, may be used as the signal which is measured and/or trained. Optionally, exact grid positions and associated values are aimed for and/or acquired. Alternatively or additionally, a relative pattern, for example, greater activation on one motor area, is a target of the rehabilitation. Optionally, selecting grid area targets may be used to help shift brain activity. For example, causing a patient to prefer to have pre-motor activity 1 cm away from its "natural" location, may be used to shift the pre-motor area and allows for use of the freed area for another purpose. In another example, control of an activation area is used to intentionally suppress taking over of brain areas by functions which it is not desired for them to take over, for example, a function which the patient is not exercising and might otherwise regress. Optionally, moving an activation area is used to intentionally "erase" existing activity, for example, activity associated with a phantom limb.

In an exemplary embodiment of the invention, desired activation areas are decided by a treating physical, for example, based on areas which are known to be damaged or undamaged and/or based on a plan for reorganization of the patient's brain. Optionally, the plan is changed as the ability of the patient to exhibit motion and/or other types of plasticity is assessed.

Optionally, incorrect and/or undesirable activation is "rewarded" by a bad-sounding sound and/or by preventing motion. Optionally, a continuous feedback is provided, in degree of resistance to motion and/or assistance to motion being dependent on degree of undesirability or desirability of an activation. Optionally, different stages in an activation (e.g., BP, PMP) are entrained separately.

Detailed Examples of Use of System 600

The following sections describe exemplary uses of system 600 for rehabilitation in association with cognitive measurements, in accordance with exemplary embodiments of the invention. More detailed and explicit examples are described first. It should be appreciated that these are only examples and not all the details described need to be provided in every embodiment of the invention.

Exemplary Recording Setup

Figure 6B:
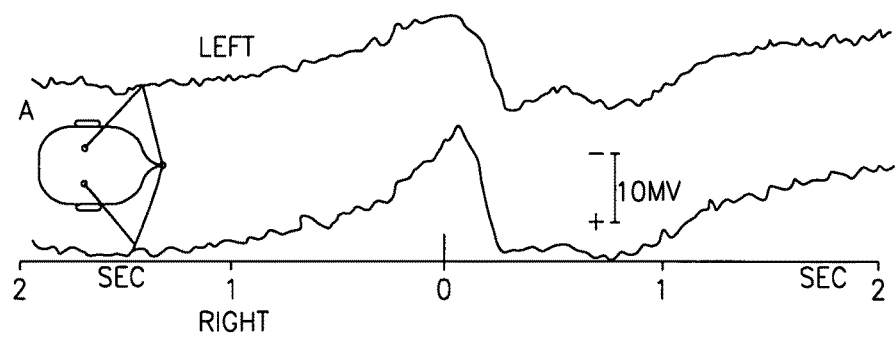
FIG. 6B shows a proposed recording arrangement to monitor MAC and the expected signals, in accordance with an exemplary embodiment of the invention.

FIG. 6B shows a proposed recording arrangement to monitor MAC and the expected signals related to a left arm movement (deeper BP and higher MP recorded over the right hemisphere). It should be noted that (unlike previous Figures) negative deflection is upwards.

Example of Calculation of Bilateral Cortical Activation

This exemplary exercise features the synchronized bilateral movement of arms, (paretic and healthy), in a mirror like fashion; so that the same set of bilateral homologous muscles are activated in the same progressive fashion along the movement path. In some cases, these requirements may be relaxed somewhat. Generally, however, a matching of the muscles which actually do the motion is desired, for example, so that the motion plans and/or feedback analysis are easier for the patient to transfer.

Figure 7:
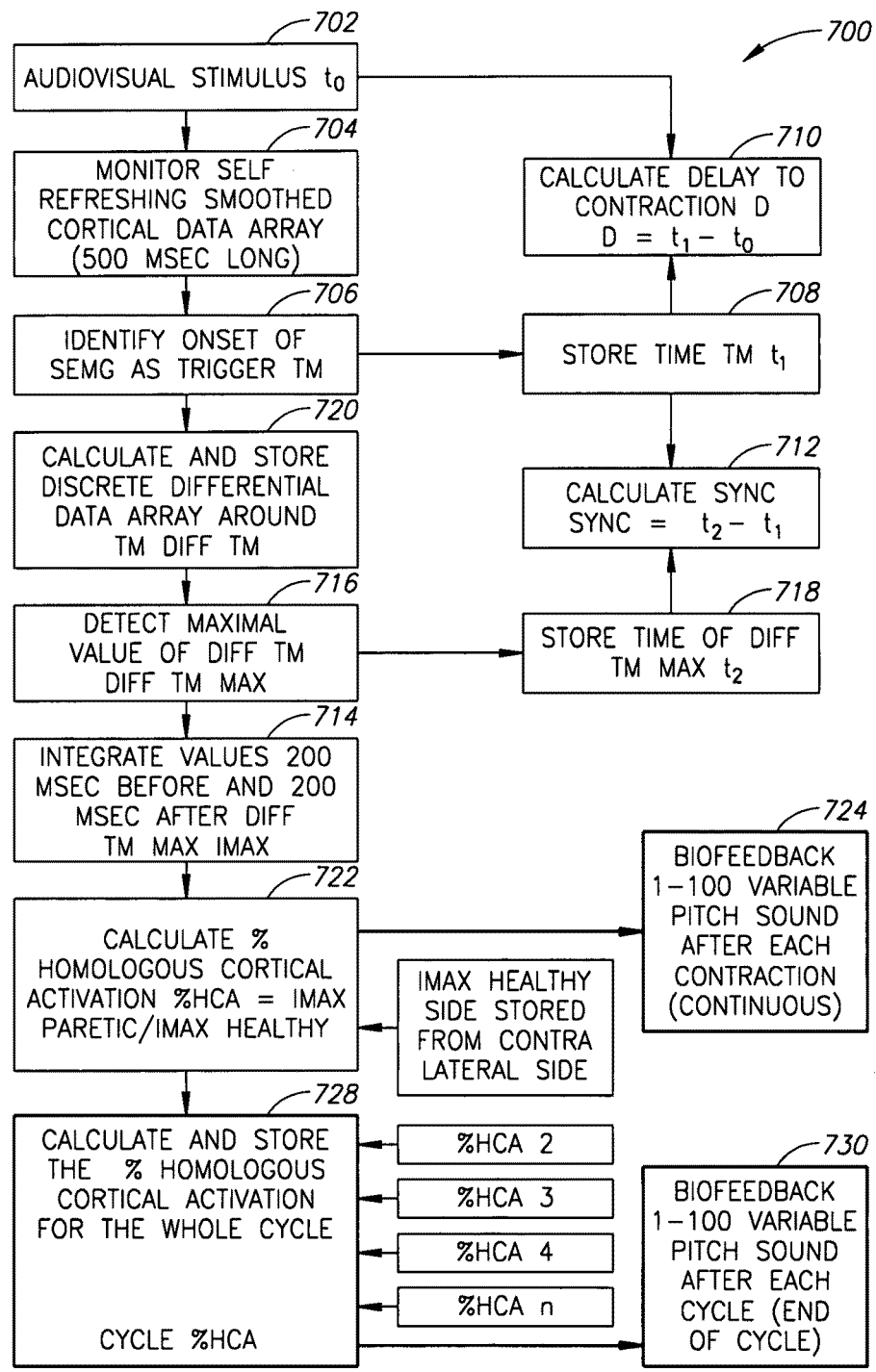
FIG. 7 is a flowchart of a method of recording bilateral cortical activation, in accordance with an exemplary embodiment of the invention.

During each cycle (movement loop) and for each one of the peripheral muscles monitored by the sEMG facility, (e.g., a four muscle sEMG arrangement) system 600 performs/displays the following methodological/processing stages (also shown as a flowchart 700 in FIG. 7), with the caveat that (a) the particular numbers shown are only intended to be examples and (b) some of the acts described below may be omitted and/or changed in order and/or replaced by other acts:

1. Upon each start of each movement loop, display a special audio-visual stimulus that acts as t0 synchronization cue of the movement loop. At t0 all data is refreshed and an internal clock starts to count (702).

Figure 1:
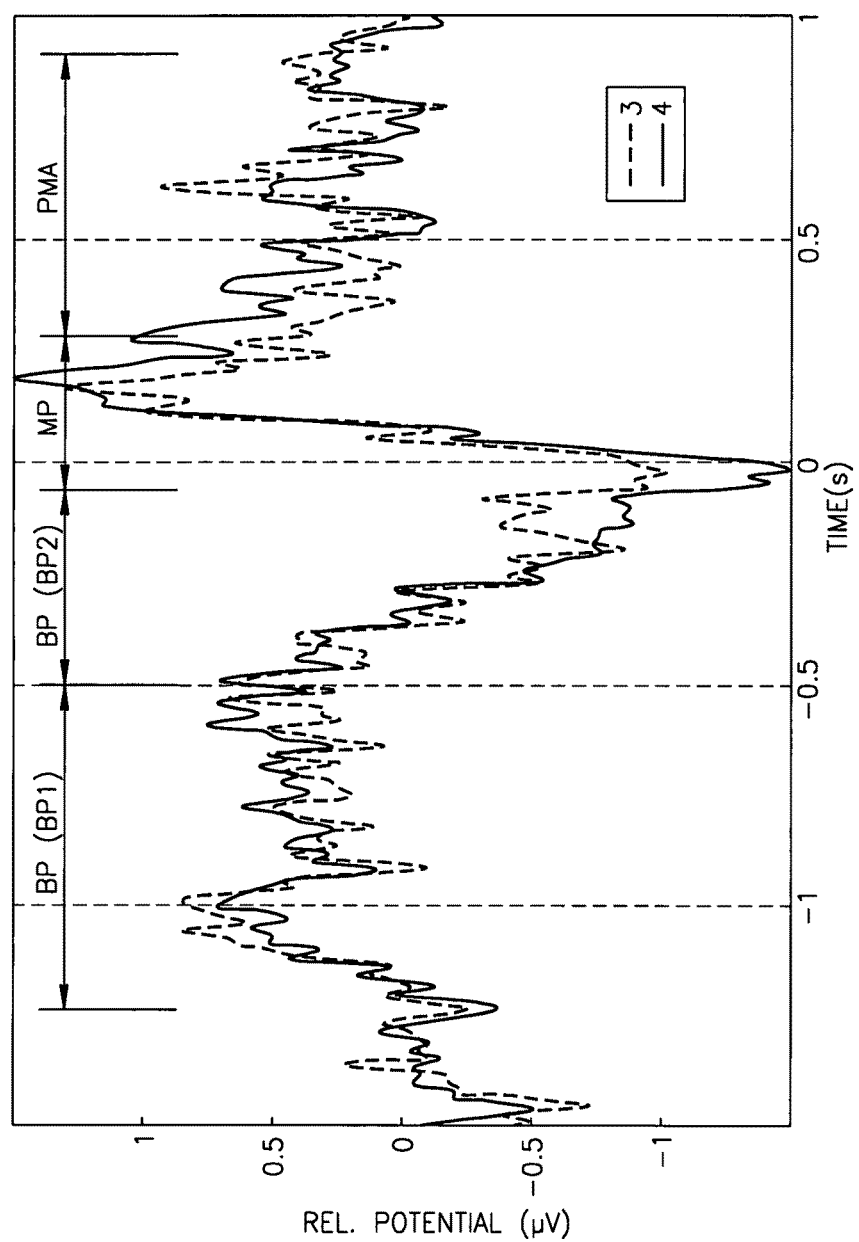
FIG. 1 presents an averaged Motor Related Potential template that illustrates BP periods.

2. Record continuously a self-refreshing time series of optionally pre-filtered and/or smoothed (e.g., using a suitable moving average method) slow cortical data (optionally recorded from electrodes C3 and C4) over X1=500 msec (the X1 variable is optionally changed according to experimental adjustment). This data has a length that can cover the late part of BP (BP2) and the beginning of the muscular activation (MP) (FIG. 1.). The sequence of data in each MAC signal between BP2 and MP typically shows a sudden shift from maximal negativity at the end of BP2 to a maximal positive value after the muscle starts to contract. In an exemplary embodiment of the invention, this change is used for detection and quantification purposes, as it is typically easily discernable in MAC signals. This may be alternative or additional to a conventional experimental approach to MAC in which the interest is in the actual shape of the MAC, particularly with respect to the degree of negativity of the BP and CNV. In order to improve signal to noise ratio a summation and averaging process over repeated similar signals/trials is used so that noise cancels out and a cleaner averaged signal emerges from the process. In this embodiment (detecting the transition), reliable data is optionally extracted form a single (or small number) trial and the BP2-MP transition shift possibly provides the means to execute quantification/biofeedback steps for every single muscle contraction of a single trial (704).

3. Identify the onset of the sEMG on the healthy side as trigger (TM) (706).
4. Store time of TM (t1) in the internal clock (708).
5. Calculate the delay to contraction (D=t1−t0) and compare with an expected value (optionally provided from previous loops and/or a "personal signature", described below). Each one of the agonist/antagonist muscles involved sequentially in a fixed (in time and space) movement will typically have its own characteristic time of contraction. The series of Ds over each movement loop optionally serves as a measure of the synchronization control of the movement as a whole. (710)
6. Upon monitoring TM, (for each muscle), calculate the differential values from the data present in the self-refreshing time series data array recorded continuously (see act 2). Store discrete differential values for a period from 250 msec before TM until 250 msec after TM (DIFF TM). Here the marked deflection between the largely negative late BP2 stage and the largely positive early MP stage gives a series of differential values with a positive spike-like peak shape over this phase of the MAC. (720)
7. Establish maximum value of DIFF TM (DIFF TM Max). This event should generally take place immediately after the start of muscular contraction t1. (716)
8. Calculate and store time of DIFF TM Max (t2) (718)
9. Calculate t2−t1=SYNC. Values of SYNC <0 and >50 msec are possibly erroneous and may indicate bad synchronization between cortex activation and motor performance or may be an artifact. SYNC is optionally used as a self-testing parameter. (712)
10. Integrate (mean) values for 400 msec; 200 msec before and 200 msec after DIFF TM Max (Imax) and store this bit of data for each muscle bilaterally. The window of differential data to be integrated is optionally "trimmed" from 500 msec in previous stages to 400 msec in order to avoid the influence of semi-raw data above (before), the maximal negativity point during BP2 or data below (after), the maximal positivity point during MP. (714)
11. Calculate Imax Paretic/Imax Healthy*100=% HCA (% of Homologous Cortical Activation) for each part of Homologous muscles in the upper arm. % HCA optionally provides an immediate value for the degree of activation opposite to the paretic side in relation to the healthy control. (722)
12. % HCA is translated into a suitable 1-100 (an arbitrary scale) variable pitch sound delivered at the end of each contraction of each muscle as audio feedback to patient. Since it can be important to provide accurate on-line biofeedback there is optionally provided a "safety valve" that will prevent the display of erroneous biofeedback: Audio biofeedback results are displayed, and % HCA are stored for subsequent post-processing only if SYNC <0 and >50 and D is as expected from personal signature. The series of audio displays, (one after each muscle contraction), described in this section represent a form of continuous audio biofeedback along the movement loop. This feature may enable the user to identify particularly difficult stretches along the path. When a continuous series of high pitch sounds are heard all through the loop the user can understand that that particular movement is now learned. Other audio feedback may be used instead. Optionally, visual or tactile feedback is used, for example, to complement audio feedback for or patients with hearing problems. (724)
13. Upon the completion of each device operation cycle, calculate mean values of % HCA for all muscles during the loop (CYCLE % HCA). Store CYCLE % HCA for each loop and sound (730) a rather longer 1-100 variable pitch sound which represent the sound feedback for the whole cycle. In this way the user can be provided with online continuous feedback, feedback at the end of each cycle and/or an assessment feedback value at the end of a series of cycles at the end of a rehabilitation session. HCA is optionally used as an assessment measure. (728)

In an exemplary embodiment of the invention, short windows (e.g., 200 msec) are used so as to better compare pairs of muscles. As the window is made longer, the difference may become less distinguishable. The actual delays may change, for example, based on the patient and/or previous records thereof.

In an exemplary embodiment of the invention, various thresholds are defined as quality indicators if thresholds are not met (e.g., for a measurement), then the recording is optionally dropped as potentially suffering from a quality problem.

Example of Calculation of Mono-lateral Cortical Activation

This exemplary exercise involves the work with a single paretic arm. In this embodiment the methodology/processing is similar to the one describe previously (for bilateral activation) but the results are optionally compared with those of a trial completed previously with the healthy contra lateral arm.

If the patient is unable to carry out the exercise loop with the strength of his own muscles, system 600 may become active and move the arm (totally or just partially, adding its force to the one generated by the subject). The triggering schedule in this case is optionally provided by system 600 using pre-programmed time cues calculated from the patient signature with the healthy arm in previous trials. For example, the timing of various muscle movements for a healthy arm may be stored and then used for the paretic art, optionally slowed down to match a generally slowed down condition of the arm. The slowing down is optionally determined by measuring a short sequence of motion of the paretic arm and comparing this sequence to the stored values for the healthy arm.

An example of an exercise follows, again, with the numbers and/or the acts being exemplary only:

1. Before the start of each movement loop, display a special audio-visual stimulus (S1) that acts as t0 synchronization cue of the movement loop. At t0 all data is refreshed and a device internal clock starts to count. For this type of exercise the user is instructed that after t0 s/he will be asked to contract a muscle and start a movement by displaying a second time cue t1 (described in act 3.)
2. Record continuously a self-refreshing time series of optionally pre-filtered and/or smoothed (e.g., using a suitable moving average) slow cortical data (recorded from electrode over the contra lateral central zone; C3 or C4) over X1=500 msec (X1 value can be changed, for example, according to experimental adjustment).
3. Relate to a time (t1) for the contraction of a particular muscle. (This time has been previously calculated for the healthy arm). At this stage system 600 provides another time cue (S2) signaling the start of the contraction.

4. Calculate the differential values from the data present in the self-refreshing time series data array recorded continuously (see act 2.). Store discrete differential values for a period from 250 msec before S2 until 250 msec after S2 (DIFF S2).
5. Establish maximum value of DIFF S2 (DIFF S2 Max). This event should generally take place immediately after the start of muscular contraction t1.
6. Integrate (mean) values for 400 msec; (200 msec before and 200 msec after) DIFF S2 Max (Imax) and store this bit of data for each muscle.
7. Calculate Imax Paretic/Imax Healthy (previously recorded)*100=% HCA (% of Homologous Cortical Activation) for each part of Homologous muscles in the upper arm.
8. % HCA is translated into suitable 1-100 variable pitch sound delivered at the end of each contraction of each muscle as audio feedback to patient.
9. Upon the completion of each device operation cycle, calculate mean values of % HCA for all muscles during the loop (CYCLE % HCA).

Exemplary Activation of Damaged Side of Cortex from Healthy Contra Lateral BP

In an exemplary embodiment of the invention, another mode of operation of system 600 is the detection and use of a BP2-MP time cue from the healthy side, (as described above), in order to stimulate the contra lateral (damaged side) of the cortex. Stimulation can be, for example, with an electromagnetic coil similar to the ones used in conventional EM Cortex Stimulation. Alternatively or additionally, stimulation is provided by using system 600 to move the paretic limb.

This embodiment exemplifies a kind of FES (Functional Electro Stimulation) that is based on the activation of the contra-lateral healthy side while performing a bimanual mirror like type of movement as mentioned above.

In an exemplary embodiment of the invention, what is desired is not to provoke a contraction but just to stimulate below the threshold of contraction so as to assist any endogenous production of MP to achieve over-threshold values and be effective in order to produce movement. This particular arrangement may help the user also to associate central activation with peripheral movement, possibly encouraging plasticity. Optionally, actual motion is also helped by manipulator 604, possibly further reducing the threshold of activation in the brain and/or muscles.

Alternatively or additionally to electromagnetic or electrical stimulation (e.g., using a DC current), in an exemplary embodiment of the invention, mental imagery or other cognitive activity caused by system 600 has an effect of activation, optionally a visual display and/or a physical motion. Optionally, the assistance of system 600 acts to lower the threshold, rather than to activate muscles. Optionally, the assistance of system 600 acts to reduce mental concentration required for planning the details of the motion and/or performing real-time feedback to ensure the motion is correct and, instead, a patient is freer to concentrate on planning of the motion. In an opposite usage, the fact that system 600 moves a limb allows a patient to clearly mentally image the motion, so the planning stage is made easier, leaving more attention to other stages.

In one example, assistance is by the system providing a power boost to motions generated by the patient. In another example, assistance is by the system applying a force that returns the limb to the correct path (e.g., instead of or in addition to such force applied by the patient). In another example, assistance is by the system moving the limb through the required motion, to help create suitable mental imagery or learn the expected kinesthetic feedback. Similarly, a patient, by such assisted motion, can learn when to expect pain, or which parts of the motion might require more concentration and/or planning. In another example, the system provides one dimensional property of the motion, such as the tempo of the motion (e.g., velocity amplitude) with the patient providing another dimensional property of the motion, such as direction, or vice-versa. In another example, the system repeats a motion carried out by the patient with the same or opposite limb, allowing the patient to "merely" repeat a previous planning or execution activity.

The system optionally provides a score during such a pre-test, showing the patient where more effort will be required during voluntary motion. Alternatively or additionally, as noted above, such feedback can be provided during motion, for example to assist in attention.

Example of Using SCP as Part of a Rehabilitation Process

Slow Cortical Potentials (SCP) represent another type of electrophysiological signal recorded from the scalp that can be translated into parameters able to interact with the mechanical and/or processing modules of system 600, especially for use in rehabilitation.

The use of SCP recordings integrated into system 600 (or other rehabilitation system) can be particularly useful in the very early stages of rehabilitation, when no sign of movement or muscular activity are present. In this case the SCP signals can be used to move the robot and hence to allow movement of the paretic hand accordingly. Thus, a patient can receive feedback on intentions, possibly assisting in the plasticity process. It should be noted that feedback can be provided visually and/or by moving a robot affecter. However, actually moving a patient's limb may assist in the rehabilitation or motor control.

By using system 600 with SCP, the patient can learn to control the SCP by observing the effects of brain activation or inhibition on the position of a limb. Optionally, a pre-selected flexion/extension path is used for such training. Alternatively, more complex motions, such as circular motion may be used. In some embodiments of the invention, brain signals are used to initiate and/or stop motions. In others, they are used to modify existing motions. Alternatively or additionally, they are used to allow a motion to continue, as long as the brain activity matches a desired pattern.

Figure 8:
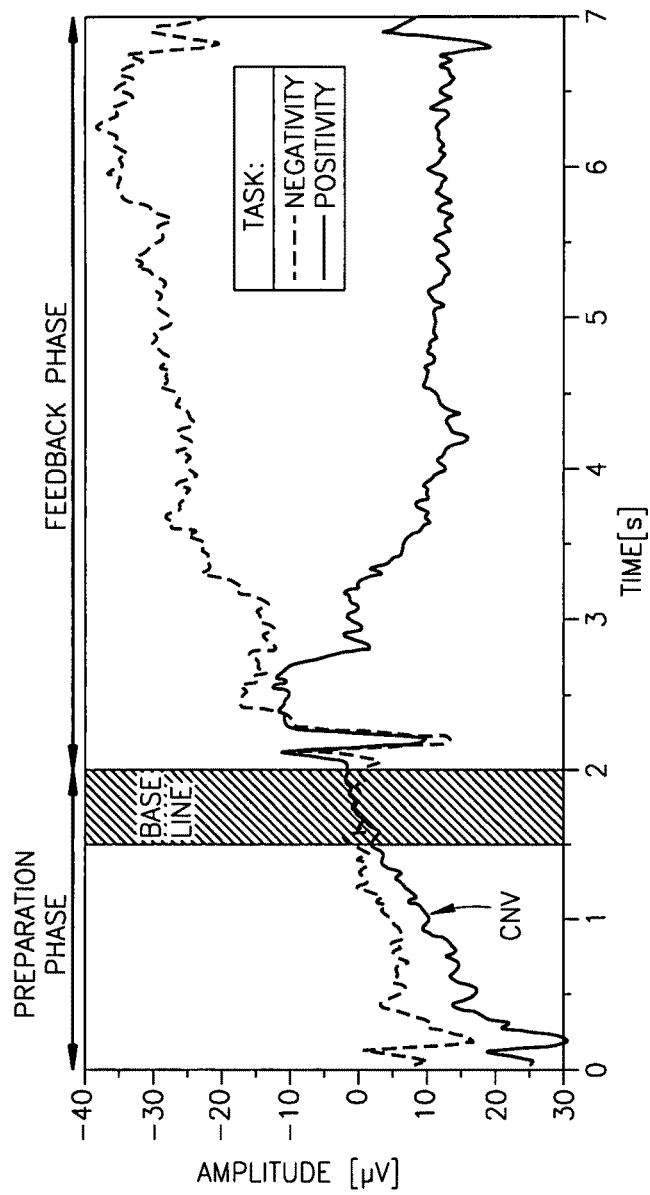
FIG. 8 shows SCP signals measured from a patient.
Figure 9:
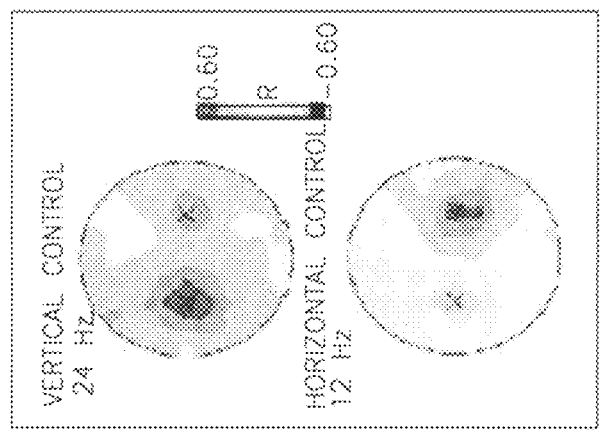
FIG. 9 shows mu rhythm sensing used to control a target.
Figure 9:
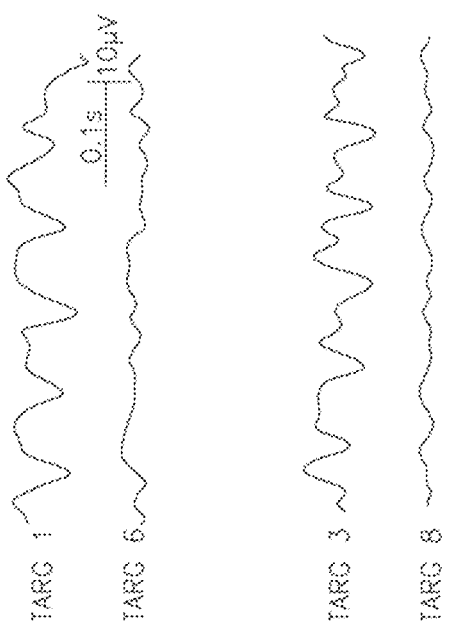
Figure 9:
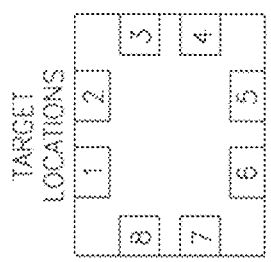

In an exemplary embodiment of the invention, signals from the brain are acquired by electrodes on the scalp, (SCP), and processed to extract a parameter directly proportional to the sign and/or amplitude of the signal. This parameter is then used to direct the manipulator 604 to change position of the arm according to the various levels of brain activation and/or inhibition in a pre-selected flexion/extension path. In an exemplary embodiment of the invention, at the beginning of rehabilitation the movement follows a very simple mono-directional path and reflects the activity recorded from a single electrode over the scalp. FIG. 8 shows actual SCP signals recorded from a subject producing cortical activation, and cortical inhibition, which signals may be used to drive mechanical motion in accordance with some embodiments of the invention.

Optionally, the larger the degree of activation the more complete the degree of flexion from a middle point, the larger the degree of extension from a middle point of the motion.

Optionally, in later stages, the patient can use a multiple electrode arrangement covering several sites over the scalp. The combined activity from all these electrodes can be then analyzed and processed so to facilitate the entrainment of more complex movement paths.

Mu Rhythm Exemplary Implementation

Alternatively or additionally to SCP signals, Mu rhythm recordings provided by system 600 (or another rehabilitation system) may be particularly useful in the very early stages of rehabilitation, when no sign of movement or muscular activity are present. In an exemplary embodiment of the invention, some movement of the robot will be triggered by the learning and manipulation of one or more of Mu, SMR and/or Beta rhythms.

In an exemplary embodiment of the invention, signals from the brain are acquired optionally by electrodes over C3 and C4 on the scalp, and processed to extract a parameter directly proportional to the degree of desynchronization of the recorded rhythm. This parameter is then used to direct the mechanical modules of the rehabilitation device to change position of the arm accordingly.

Optionally, the Mu rhythms implementation is used in the early stages of rehabilitation primarily to move the robot in a purely mono-directional fashion and without much involvement of peripheral structures (nerves and muscles). Optionally, different movements are used to train different types of control over the brain and/or different control for different movement conditions (e.g., different limbs and/or different trajectories). As also described herein, manipulator 604 and/or FES 622 may be used to provide motion enhancement (or motion) synchronized to the cortical activity.

Examples of Linking of Central Activation and Movement

Use of MAC Potentials Related to Voluntary Movement

Briefly, MAC potentials include the early Readiness or "Bereitschaft" Potentials related to the planning of a movement which involves two negative waves preceding the movement: the early one which appears to the related to the activation of mesial frontal cortex and the "supplemental motor area" which is symmetric and bilateral in nature, a later negative wave just before the execution of the movement related to the activity of cortical-spinal tract concerning efferent discharges of pyramidal tract which is maximal contra-lateral to the movement. The beginning of the movement is marked by a strong positive wave that starts with the onset of muscle contraction and includes further positive waves reflecting first central and later peripheral feedback from muscle and joints. These positive waves are maximal when recording at the top of the scalp at Cz.

In an exemplary embodiment of the invention, the recording of bilateral MAC is used to monitor assess and/or entrain with system 600. This approach optionally compares the performance of both arms (one normal and the other paretic) and the link with the movement (muscular contraction) is intrinsic to this approach.

Use of SCP Signals in BCI Device Entrainment

In an exemplary embodiment of the invention, SCP signals are trained to control a BCI device. Such signals may be based on generalized thalamo-cortical and intra-cortical activation/inhibition. The more the thalamo-cortical and intra-cortical activation the bigger the "negativity" of the SCP signal; the less the thalamo-cortical and intra-cortical activation the bigger the "positivity" of the SCP signal.

In an exemplary embodiment of the invention, SCP training & control is used to add a neurological dimension to the therapeutic use of system 600.

In an exemplary embodiment of the invention, manipulator 604 is moved according to the characteristics of the SCP signal and/or according to the integration of features of various SCP signals recorded from various electrodes placed at different sites of the scalp. This approach can facilitate the creation of movement even when there is total paresis. This may have significant psychological and physiological positive implication for the patient.

Optionally, an ultimate purpose of system 600 is to encourage brain healing and plasticity in order for the patient to, first, initiate movement of a paretic member and eventually to regain full movement. Optionally, this is achieved, at least in part, by linking the active neuronal loops in the brain cortex related to activation/inhibition as reflected in the SCP with the motor knowledge/rehearsal/activation that takes place while planning and executing the movement.

Optionally, a temporal and/or intentional linkage is created between two or more of the following three factors:

(a) the cortical activity being manipulated (by the patient) to control the BCI device;

(b) the passive or active movement, generated or monitored by system 600 and its various triggering facilities; and (c) the exact sequence of neurological events taking place at central and peripheral cells of the motor path involved in that particular movement.

In an exemplary embodiment of the invention, the sequence of neurological events is detected using EEG and/or fMRI and linked to the other rehabilitation activities, for example, by providing positive feedback using system 600. Optionally, the positive feedback is by motion. Alternatively or additionally, the positive feedback is by visually presenting whether a correct neural pathway is being activated. Optionally, the neural pathway that should be generated is estimated by viewing pathways for motions that do not involve paretic limbs or those for which some motion is carried out in a paretic limb.

Optionally, once the BCI is entrained, it may be used for controlling a prosthesis, not during a rehabilitation session.

In an exemplary embodiment of the invention, the ability to repeat a motion exactly many times is used to acquire more complete statistics of brain activation. Optionally, the use of repetitions allows a better filtering and/or averaging of noise. Optionally, this allows a more precise pattern recognition and/or signal processing for detecting particular SCP (or other) signals for the BCI system.

Other linking methods are described herein and may also be used for controlling prostheses.

Use of Residual sEMG to Modulate SCP Based Device Movement

In an exemplary embodiment of the invention, residual (e.g., without contraction) sEMG is used to modulate SCP based movement.

Optionally, after the patient learns to move manipulator 604 with his/her SCP signals, any residual sEMG peripheral signal detected over relevant muscles is used as a co-trigger, (e.g., with the related central signal SCP or MAC), to move the manipulator 604 and in this way the patient possibly integrates cortical activation and muscular performance.

Use of Agonist/Antagonist sEMG Discrimination to Modulate SCP Based Movement

Another optional method of linking cortical activation and muscular performance takes into consideration the particular features of the movement the patient is trying to learn to execute.

In this approach the degree of contraction and relaxation of the muscles involved in a particular movement, (e.g., as reflected in the amplitude of the RMS sEMG signal recorded over each muscle), is used as biofeedback information that is provided to the patient (e.g., by display) to activate or inhibit SCP (by the patient).

Contraction is defined as an increase of sEMG above an average RMS baseline level established beforehand, and relaxation a decrease of sEMG below the average RMS baseline.

Example of Early Rehabilitation Stage Implementation (Total Immobility or No sEMG)

In this exemplary methodology, in early stages of the rehabilitation process, when no movement or residual sEMG is available to be recorded from the paretic member, the sEMG recordings are done on the healthy arm as the movement is performed by the healthy arm attached to one side of a two sided system 600 (e.g., with two manipulators 604) and according to the force created in the healthy arm. The other manipulator of the robot is attached to the paretic arm and is programmed to move (or modify its movement) to be in a similar path as the contra-lateral healthy limb ONLY when correct activation or inhibition is recorded over the relevant SCP signal.

Following are exemplary acts in such training. Not all the acts are essential and some may be omitted, changed in order, have parameters changes and/or be replaced by other acts:

1: Determination of therapeutic movement: First the physiotherapist determines the movement loop to be learned according to his/her professional assessment of the patient's restrictions. Optionally, system 600 is used to assess the patient's restrictions.

2: Definition of the movement in sEMG terms: The agonist and antagonist muscles involved in that particular movement are defined and their respective contraction and relaxation periods in the movement loop are recorded and established. This may be performed, for example, automatically by system 600 once the motion is selected.

3: Relate single (agonist) muscle contraction to SCP activation: Take major agonist muscle involved in the movement loop and each time it is about to contract (e.g., 0.5 sec before) ask the patient to generate a synchronous SCP activation (more negativity) on an electrode placed over the contra-lateral side of the motor cortex. This may take some practice.

4: Reward synchronous cortical activation: If SCP activation was achieved, reward by moving paretic arm together with healthy one. Other rewards may be used as well or instead.

5: Relate single muscle relaxation to SCP inhibition: Take same major agonist muscle involved in the movement loop and each time it is about to relax (e.g., 0.5 sec before) ask the patient to generate a synchronous SCP inhibition (more positivity) on an electrode placed over the contra-lateral side of the motor cortex.

6: Reward synchronous cortical inhibition: If SCP inhibition was achieved, reward by moving paretic arm together with healthy and completing the loop. Optionally, rewarding is not carried out for every correct motion.

7: Relate main antagonist muscle relaxation to SCP activation; and antagonist muscle contraction to SCP inhibition: acts 3 and 5 are repeated, with the antagonist muscle. It should be noted that while agonist contraction is trained with SCP activation, antagonist contraction is trained with SCP inhibition; likewise, when agonist relaxation is trained with SCP inhibition antagonist relaxation is trained with SCP activation.

8: Reward accurate synchronous cortical activation and inhibition while relaxing and contracting the antagonist muscle: This is similar to acts 4 and 6 but with the antagonist muscle. If SCP activation was achieved before antagonist relaxation and if SCP inhibition was achieved before antagonist contraction, reward by moving paretic arm together with healthy arm. It should be noted that different rewards and/or feedbacks may be used to signal, for example, correctness of amplitude, timing and/or type of activation.

9: Relate a pair of agonist/antagonist muscle contraction/relaxation to SCP activation: SCP activation (more negativity) is trained to be related to agonist contraction and antagonist relaxation in the first phase of the movement.

10: Relate a pair of agonist/antagonist muscle relaxation/contraction to SCP inhibition: SCP inhibition (more positivity) is trained to be related to agonist inhibition and antagonist contraction in the second phase of the movement.

11: Reward accurate synchronous cortical activation and inhibition while working with a pair of agonist/antagonist muscles.

Figure 10:
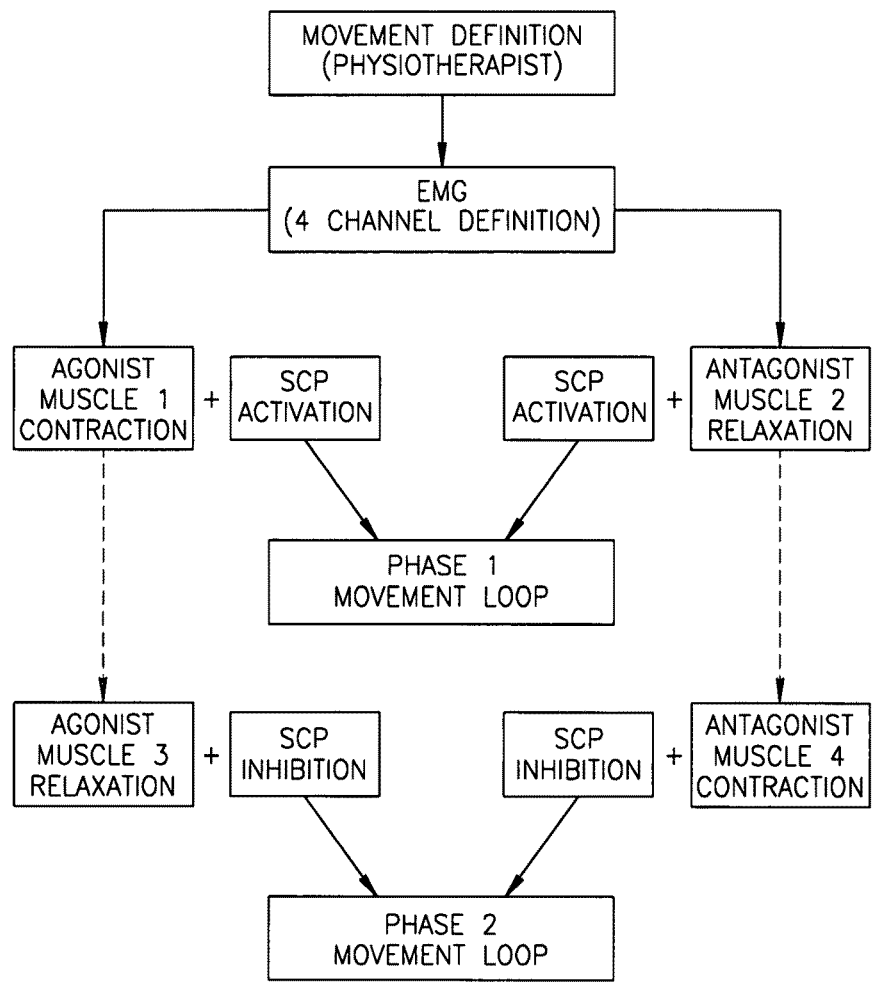
FIG. 10 is a flow chart of a process of agonist/antagonist rehabilitation, in accordance with an exemplary embodiment of the invention.

12: Repeat acts 9 to 11 but with two agonist/antagonist pairs of muscles: This involves the recording of sEMG from 4 (or more) different muscles, optionally always relating agonist/antagonist muscles contraction/relaxation to SCP activation and agonist/antagonist muscles relaxation/contraction to SCP inhibition. Then reward accurate performance as before. This last act is shown in FIG. 10.

Optionally, after the activities of muscle pairs are linked, additional rehabilitation designed to target single ones of the muscles is performed.

Figure 11:
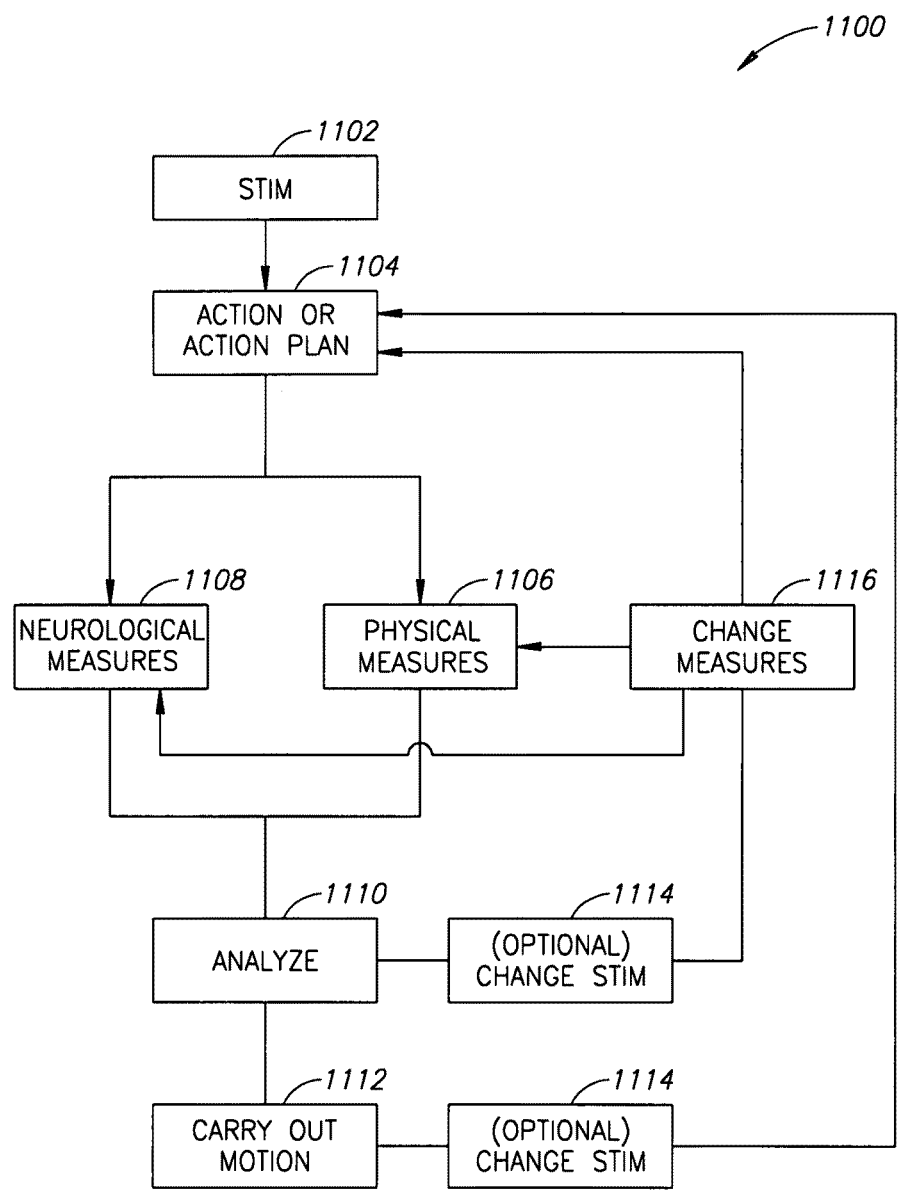
FIG. 11 is a flowchart of a method of initiating motion, in accordance with an exemplary embodiment of the invention.

FIG. 11 is a flowchart 1100 of an exemplary method of jumpstarting a rehabilitation process, in accordance with an exemplary embodiment of the invention. In an exemplary embodiment of the invention, the method of FIG. 11 is configured so that any motion or intent detected by the system will generate a noticeable feedback to the patient. Optionally, detection is skewed towards detecting motion, even if what is detected is noise. Failure to detect a motion signal is optionally dealt with by changing the detection method and/or a stimulation method.

At 1102, a stimulation is optionally provided to the patient, to cause the patient to move or want to move. Various stimulation methods may be used, for example, audio prompts, audio instructions, displays, stimulation of nerves, CNS stimulation and/or mechanical vibrations. Optionally, stimulation is in response to a readiness signal detected in the patient.

In an exemplary embodiment of the invention, the stimulation provided is guided mental imagery. Optionally, the patient's eyes are closed during the imagining. Optionally, visual assistance is provided to the patient, for example, one or more of a graphic sequence, a processed image or video sequence and a static display. Optionally, the processed image or sequence comprises an image of the patient processed to show motion, for example, by mirror, or by segmenting the patient's limbs and moving them, in the image. Optionally, once the movement is completed, a comparison is made to see if the motion matched the imagery. Optionally, the stimulation is changed periodically, to prevent habituation by the patient. Optionally, however, for jumpstarting movement, such comparison is less important than actually achieving motion at all or which is anywhere near the intention.

Alternatively or additionally, the stimulation comprises moving the limb using device 600.

At 1104, the patient is expected to try to move and/or try to initiate a motion or other action plan.

At 1106, various physiological measurements are made to see if there are any hints of motion, for example, measuring sEMG and/or actual motion.

At 1108, neurological measurements are made alternatively or additionally to physiological measurements. Optionally, a vector of neurological measurements is defined, for example including various signal parameters optionally associated with areas of measurement.

At 1110, the measurements are analyzed to see if there are any indications of motion or intent of motion. If so, a motion or other feedback is carried out at 1112. Optionally, any existing motion is amplified.

At 1114, stimulation parameters are optionally changed, for example, to prevent habitation or as part of a search among different stimulation methods and/or parameter values for a stimulation which will work. Various search methods are known in the art. A particular optional change in stimulation is an increase in amplitude of stimulation.

At 1116, the measurement method and/or signal processing method is changed. For example, an area to which electrodes are connected may be changed.

It is expected that at least for some patients, the method of FIG. 11, if repeated often enough, will elicit some movements or at least indications of the generation of an intention to move, which indications can be a starting point for further rehabilitation.

Example of Later Rehabilitation Stage Implementation (Some Mobility or Residual sEMG)

At a later stage of the rehabilitation process, when some residual or even effective sEMG is available, the sEMG recordings are optionally carried out on the paretic arm and the SCP measurements are, as usual recorded centrally or over the contra-lateral side over the motor cortex Cz and C3 or C4).

In an exemplary embodiment of the invention, the movement is performed, by the paretic arm attached to a single manipulator system 600.

Optionally, the same schedule is followed as before (acts 1 to 12 just described). Optionally, the reward is given in one or more of the following forms:
- System 600 can assist the patient in performing the movement by starting the motion and letting the user to continue performing it.
- System 600 can assist the movement by reducing the overall resistance to the movement loop.
- System 600 can assist the movement by providing suitable supra-threshold FES to enhance contraction of the various muscles at the expected time and/or part of the movement loop.
- System 600 can provide audiovisual reward.

Integrated Example

Arm flexion and extension generally requires the synchronized action of the Biceps and the Triceps muscles. For example: Biceps contract/Triceps relax lead to flexion; Biceps relax/Triceps contracts leads to extension.

Optionally, a patient suffering of total arm hemi paresis with the right side affected, is treated using the following rehabilitation acts:

1. Teach and train patient to generate SCP activation over C3 (contra-lateral to the paretic arm) or Cz (central point) 0.5-1 sec before the start of a contraction of the left Biceps (e.g., identified by increase of sEMG RMS). The patient is attached to a bi-manipulator system 600 and trying to produce a bilateral arm flexion.
2. Reward synchronous cortical activation by flexing the paretic arm together with the healthy left arm.
3. Teach and train patient to generate SCP inhibition over C3 (contra-lateral to the paretic arm) or Cz (central point) 0.5-1 sec before the start of a relaxation of the left Biceps (e.g., detected by decrease of sEMG RMS). The patient is attached to a bi-manipulator system 600 and trying to produce a bilateral arm extension.
4. Reward synchronous cortical inhibition by extending the paretic arm together with the healthy left arm.
5. Teach and train patient to generate SCP activation over C3 (contra-lateral to the paretic arm) or Cz (central point) 0.5-1 sec before the start of a relaxation of the left Triceps (e.g., detected by decrease of sEMG RMS). The patient is attached to a bi-manipulator system 600 and trying to produce a bilateral arm flexion.
6. Reward synchronous cortical activation by flexing the paretic arm together with the healthy left arm.
7. Teach and train patient to generate SCP inhibition over C3 (contra-lateral to the paretic arm or Cz (central point) 0.5-1 sec before the start of a contraction of the left Triceps (e.g., detected by increase of sEMG RMS). The patient is attached to a bi-manipulator system 600 and trying to produce a bilateral arm extension.
8. Reward synchronous cortical inhibition by extending the paretic arm together with the healthy left arm.
9. Teach and train patient to generate SCP activation over C3 (contra-lateral to the paretic arm) or Cz (central point) 0.5-1 sec before the start of a contraction of the left Biceps accompanied by the associated relaxation of the left Triceps (e.g., detected by increase of sEMG RMS over the Biceps and decrease of sEMG RMS over the Triceps). The patient is attached to a bi-manipulator system 600 and trying to produce a bilateral arm flexion.
10. Reward synchronous cortical activation by flexing the paretic arm together with the healthy left arm.
11. Teach and train patient to generate SCP inhibition over C3 (contra-lateral to the paretic arm) or Cz (central point) 0.5-1 sec before the start of a relaxation of the left Biceps accompanied by the associated contraction of the left Triceps (e.g., detected by decrease of sEMG RMS over the Biceps and increase of sEMG RMS over the Triceps). The patient is attached to a bi-manipulator system 600 and trying to produce a bilateral arm extension.
12. Reward synchronous cortical inhibition by extending the paretic arm together with the healthy left arm.
13. Once the above training is successfully accomplished, more complex movement, such as involving two pairs of agonist/antagonists may be entrained. For instance training to regain the flexion of the shoulder (bending the joint resulting in a decrease of angle; moving the upper arm upward to the front) and extension of the shoulder (straightening the joint resulting in an increase of angle; moving the upper arm down to the rear). The flexion and extension of the shoulder require the activity of more than one pair of agonist/antagonist muscles. Optionally, the training is continued recording sEMG over, for example, the Biceps/Triceps and the Deltoid Anterior/Deltoid posterior arrangement.

In an exemplary embodiment of the invention, a "personal signature" of parameters for movement, associated MAC (and/or other brain signals) and/or coexisting sEMG are established for a healthy arm and even in some cases bilaterally for totally healthy individuals. These are optionally used as standards against which performance of paretic arms during the rehabilitation process are compared and/or assessed, qualitatively and/or quantitatively. In an exemplary embodiment of the invention, a patient is rehabilitated to have motion which matches the patient's signature or match that of an "expert" (e.g., a Tai-Chi expert or a dancer).

Brain-Computer Interface (BCI) Embodiment

As a replacement for the brain's normal neuromuscular output channels, a BCI depends on feedback and on adaptation of brain activity based on that feedback. Thus, a BCI system must provide feedback and must interact in a productive fashion with the adaptations the brain makes in response to that feedback. In a BCI apparatus according to some embodiments of the invention, the feedback will be given by means of robotic movements and visual/acoustic feedback on the computer screen.

SCP-Robot for Enhancing Cortical Reorganization in Stroke Patients

One application of the SCP method is to use it for a direct treatment-induced cortical reorganization in stroke patients. By executing robotic movements via SCP control, an SCP-based BCI method may be used to enhance cortical reorganization directly, independently from motor capability.

In an exemplary embodiment of the invention, patients will be trained to modify the lateral difference in precentral slow potentials using neurofeedback and instrumental learning procedures (optionally receiving reinforcements, such as the success in moving the robotic arm with the affected limb). Feedback of the difference between left- and right-precentral brain activity will be provided and patients will optionally be reinforced if they will produce the required changes in brain activity upon discriminative stimuli; for example, higher negativity in amplitude over the damaged areas than negativity generated over the contralateral undamaged areas.

In an exemplary embodiment of the invention, changes in activity of the brain is used as a measure of plasticity, e.g., it is assumed that patients who achieve higher cortical activity over the injured areas will exhibit more efficient (e.g. fast, accurate, preferential) responding with the hand contralateral to the hemisphere (the affected hand which is attached to the robot), in which brain activity was increased.

Brain activity recording is optionally carried out with single electrodes or a dense electrodes array which will be attached to the scalp via an EEG-cap. In a case of lesion in the left hemisphere (affected right hand), for example, the patient will be asked to increase brain activity over this hemisphere, and/or over the specifically lesion sites (e.g., if known, for example using CT, MRI, PET, TMS, HEG, fMRI, transcarnial ultrasound for blood flow measurement, Magnetoencephalography MEG or any other brain imaging techniques) in comparison to the intact right hemisphere and/or specifically undamaged sites, so that a balance of excitability between the two hemispheres toward a normal condition can be aimed for, established and/or maintained. Optionally, in addition to measuring motor outcomes (e.g., questionnaires and measurements by system 600), brain imaging techniques that enable to determine exact damaged sites (before treatment), as well as alternations in cortical reorganization during and after treatment, for example, a fMRI scan every week over several weeks of treatment, are used, for example to determine treatment-dependent alterations in cortical reorganization over time.

In an exemplary embodiment of the invention, brain imaging techniques are used to detect the edge of a damaged area so that exercises and/or activation can selectively focus on reactivating this edge. The edge of the damaged area is possibly identified by its excitation being erratic.

In an exemplary embodiment of the invention, brain reorganization is assessed without using imaging techniques or is used to support such measurements. In an exemplary embodiment of the invention, cortical reorganization is assessed from alteration in brain activity. For example, if a patient is able to increase the level of activity (e.g. higher amplitudes) over the damaged cortical area during treatment with system 600, and if this activation correlates with movement improvement of the affected hand, it is optionally assumed that some underlying cortical networks became more active than before, which implies brain reorganization and/or other improvement. In another example, if a patient increases brain activity over the undamaged hemisphere, and this activation correlates with better motor functioning of the affected hand, it is optionally assumed that the motor cortical regions of the undamaged hemisphere control the hand movements, which implies brain reorganization.

In an exemplary embodiment of the invention, brain imaging techniques are applied at various stages of the rehabilitation, for example, at a start thereof, when stages are complete or goals reached and/or periodically. Optionally, rehabilitation is carried out using brain images, such as fMRI. Optionally, the imaging is not used for all repetitions, but only for some, for example, to note that an exercise (intra-cranial) is being carried out.

In an exemplary embodiment of the invention, high cost imaging techniques (including high resolution EEG) are made more cost effective by using such techniques to interpret low cost techniques, such as EEG. In an exemplary embodiment of the invention, a calibration session is carried out in which the patient is caused to produce a certain desired (for tracking) brain activity and this activity is both imaged using a high cost technique and by a low cost technique. In this regard cost means any cost, such as techniques which come at a cost to the patient (such as radiation imaging) or at a cost to the rehabilitation process (such as requiring the patient to remain motionless). One the target activity can be recognized based on the low cost method, this low cost method may be used for feedback during rehabilitation. Optionally, the calibration is carried out long enough and/or repeated to ensure that the low-cost method has an actual correlation with the high cost method. Optionally, the calibration session is used to assess the degree of correlation, which may assist, for example, in deciding during rehabilitation, which measure to trust and/or what weighting functions to use.

Mu-Rhythm-Robot for Enhancing Cortical Reorganization in Stroke Patients

In an exemplary embodiment of the invention, in a series of exercises the patient is asked to execute robotic movements in various directions and plans and EEG electrodes or an EEG-cap are used to measure the mu-rhythm activity over the motor areas in accordance with the execution of these movements. At the second stage of these exercises the patient is asked to imagine the executed movements, trying to cause the manipulator 604 to move in the desired direction(s). The combination of the sensory (imagination) and motor (robot movements) channels possibly will enable to teach the patients to control exactly the neuronal networks involved in movement executions, possibly achieving a direct context-dependent neural activity.

Cortical "Fingerprints" of Specific Movements/Movement's Intention

In an exemplary embodiment of the invention, a patient is trained to distinguish (e.g., generate selectively) between the EEG patterns associated with imagination of different simple motor actions, such as right or left hand movements. During the imagination of motion, specific cortical activity patterns ("cortical fingerprints") for specific movements are identified, for example a fingerprint for the motion of pushing the hand forwards, in comparison to a fingerprint which is recorded by moving the hand leftwards (or backwards, or upwards etc.). In an exemplary embodiment of the invention, in each of a series of trials, the patient will imagine one of several actions (e.g. right or left hand movement, forwards-backwards, left-right, diagonal, up-down movements) while EEG from electrodes over sensorimotor cortex (or other recording sites) will be submitted to frequency- and/or component analysis (or other analysis methods) to derive signal features. For each imagined action, an n-dimensional feature vector is optionally defined. These vectors are optionally used to establish a patient-specific classifier that determines from the EEG which action the patient is imagining. Optionally, for each patient a "cortical fingerprints movement related dictionary" that matches a specific cortical activation to a specific movement is generated. Optionally, the movements are carried out only in the mind. Alternatively or additionally, a comparison between imagined and actual motions is stored. Optionally, a patient stores such patterns before a paretic event, for example, as part of a regular checkup or when danger is identified.

In subsequent sessions, the system can use the classifier (i.e. the "dictionary") to translate the patient's motor imagery into a continuous output (e.g. moving the robot arm in the desired direction), and/or into a discrete output (e.g. initiating robot movement). This output can be presented to the patient as, for example, i) a sensory feedback through his hand, and/or ii) through online visual/acoustic feedback on the computer screen.

In another variation of this paradigm, the patient will actually move his unaffected hand and/or the affected hand which is connected to system 600, or manipulator 604 will move the patient's hand during the sessions. A set of one or more dense electrodes arrays may be used to record brain activity during these movements. This activity will be compared to the activity recorded during the imagined movements in order to find correlations in brain activity during imagined and actual movements. These "cortical fingerprints" of a movement will then be optionally used to "guess" the patient's intention and to carry out the desired movement.

Dosage

In an exemplary embodiment of the invention, the cortical effects are used to define a required dosage of rehabilitation and/or to control billing. In an exemplary embodiment of the invention, a match is made between an amount of activity by a user (for example, as measured by actual exercise time or cortical activity) and a therapeutic effect and/or a rehabilitation condition. In one example, 20 "active minutes" per day may be the dosage for medium severity pre-motor one damage. Optionally, a range of possible doses may be defined, for example a low dosage not having sufficient effect and a high dosage possibly causing over compensation or undue tiredness. Optionally, the dosage is a relative dosage dependent on the patient's total ability and/or total number of rehabilitation issues. Optionally, device 600 is used to track the actual applied dosage and/or its effect. Optionally, device 600 can distinguish the actual dosage applied to each area (or issue) in need of treatment.

Optionally, the dosage is defined as a function of one or more of physical exertion mental exertion and/or attention/engagement.

Optionally, dosage is measured in units of one or more of power, force or energy.

In an exemplary embodiment of the invention, device 600 is designed to apply a known amount of dosage and/or decide on changing an exercise schedule, once a certain dosage is reached and/or to prevent over-dosing.

In some cases, dosage is used to define a minimal level required to achieve benefit form rehabilitation, for example, a minimum exertion level or a minimal engagement level may be required.

In an exemplary embodiment of the invention, device 600 is used to ensure such minimal attention/exertion levels.

In an exemplary embodiment of the invention, attention is measured by measuring compliance and/or variation in response time to instruction. Absolute response time may be of interest, for example, if there is an expected response time based on previous activities.

While the present application focuses on physical activities, it should be noted that the methods described herein can also be used for cognitive and perceptive rehabilitation, including the usage of dosage. In an exemplary embodiment of the invention, cognitive and/or perceptive activity is detected directly. Optionally, a patient is requested to do a physical activity to indicate the cognitive or perceptive activity. Optionally, the effect of motor signals in the brain is ignored and/or used as a trigger to search for brain activity related to a decision to provide a response.

Mental State

In an exemplary embodiment of the invention, daily assessment of mental state is carried out as part of rehabilitation. In an exemplary embodiment of the invention, brain image, blood tests and/or EEG measurements are used to assess an instant mental state of a patient, for example, depression or anxiety. Optionally, depending on the motivational state of the patient additional motivation may be provided and/or lesser achievements may be expected. It should be noted that this type of depression relates to a mood, which can change hourly or daily and not to clinical depression which is a long term illness.

In an exemplary embodiment of the invention, cognitive rehabilitation progress is assessed using other means, such as problem solving or other cognitive tests. Optionally, cognitive progress is used to calibrate expected physical rehabilitation progression, for example, assuming that a same improvement rate is expected for areas with similar damage under similar exercise protocols. Optionally, an improvement template is adjusted to match a patient based on improvement in one or more functions and used to estimate expected improvements in other functions. Optionally, a template includes a correspondence between expected improvement rates for areas of different degrees of damage and/or degrees of accessibility to rehabilitation. Optionally, the template is adjusted according to actual rehabilitation effort.

In an exemplary embodiment of the invention, EEG measurements are used to determine settings, environmental cues and/or exercises that promote desired cortical brain activity and/or reduce noise that interferes with detection thereof.

In an exemplary embodiment of the invention, the environmental cues are selected form one or more of colors, images, language, or other means that have been documented to cause certain types of emotional reactions in people.

Optionally, a therapist and/or device 600 provide other motivational means, such as motivational talks, movies and positive feedback optionally timed to have a desired effect.

In an exemplary embodiment of the invention, device 600 controls simultaneously two or more of physical rehabilitation, brain stimulation, emotional control and instructions. Optionally, a rehabilitation plan is optimized to take into account the parameters being controlled.

Motion Types

In device 600 as illustrated, the motion which is controlled is generally that of a single point, e.g., a tip of the manipulator. By providing various attachments for the tip, the tip may be connected, for example to a bone, to a joint or to a different part of the body. The attachment may be rigid, for example using a strap or it may depend on cooperation of or action by the patient, for example, as a handle or a rest. Specific attachment devices, for example for a hand, arm, elbow, knee, ankle and/or shoulder may be provided. Further, as described below, multiple tips (optionally with individual manipulators) may be provided for attachment at different points of the body, on a same or different body part.

When providing rehabilitation various types of motion may be supported, for example, one or more of:

a) Passive Motion. The tip is moved (by device 600) and the patient moves with it.

b) Resisted Motion. The patient moves the tip and encounters resistance. The resistance may be of various magnitudes and may be uniform in all direction or be directional.

c) Assisted Motion. When a patient moves the tip, a positive feedback on the manipulator increases the force of motion in the direction moved by the patient.

d) Force Field Motion. The patient moves the tip. Along a certain trajectory one level of resistance (or none) is encountered. Deviation from the trajectory is not allowed or meets with resistance. Motion along a "correct" trajectory can be without resistance, or possibly assisted. An increased resistance is optionally exhibited in a volume surrounding the trajectory. An even greater resistance is optionally exhibited in a surrounding volume. A prevention of motion may be provided in an outside volume. In an exemplary embodiment of the invention, a corrective force vector is applied when not on the trajectory, pointing towards the trajectory. Optionally, instead of a corrective force, resistance varies as a function of distance from the trajectory, thus, motion of the tip is naturally urged back to the trajectory. Optionally, the force is applied in the direction of the path. Alternatively, the force maybe a unidirectional force of resistance.

This type of motion may be used to help train the patient in a desired motion.

e) Mirrored Motion. Motion of the tip is required to mirror the trajectory of motion of a different element, for example for dual limb rehabilitation as described below.

f) Free Motion. Patient moves the tip in any way he desires, possibly receiving feedback. As the patient (or therapist or helper) moves the tip, device 600, may record it for future playback. In a playback mode the prerecorded motion (or path) is optionally reconstructed using other modes. Optionally, the recorded path is modified (e.g., smoothed or otherwise edited), for example automatically or manually.

g) General Force Field. A force field and/or an assistance field is defined which is not related to any particular trajectory. For example, a range of trajectories may be allowed to be practiced by a user, or a real or virtual situation simulated (e.g., water, areas with obstacles).

h) Local Force Field. A force field which is applied to only a small locality and/or only in one or two dimensions.

i) Restricted Motion. One or more points of the body of a subject are supported or prevented from moving. Optionally, the angles between such points and the moving points on the patient are measured. In one example the elbow is locked with a dedicated harness allowing only a shoulder motion. In some embodiments, the restriction is partial and/or is provided by a movable element (e.g., the manipulator).

j) Initiated Motion. The patient initiates the motion (e.g., a 1 cm motion or 100 gram force) and device 600 completes or helps the patient complete the motion in space. The completion may be of a whole trajectory or of part of a trajectory.

k) Implied Motion. Device 600 begins the motion and the patient completes it. Device 600 may assist the rest of the motion in various manners (e.g., by changing to one of the modes described herein after the motion starts). If the patient fails to pick up the motion, device 600 may generate a cue, for example an audio reminder. Different parts of a single motion trajectory may each have a machine initiation definition. Optionally, if a patient is too slow in moving, device 600 begins the motion.

l) Cued Motion. The patient receives a cue from the system before motion according to a different mode starts. The cue can be, for example, vibration of the tip, stimulation pads on the skin, audio or visual cue. In some embodiments of the invention, the strength of the cue and/or its timing and/or other ongoing activities (e.g., a visual display and game) are used to help train the coordination between different modalities, for example, hand-eye coordination. A motion cue can be used to train a kinesthetic sense.

m) Teach Mode. Device 600 is taught a motion. In one example, a therapist performs a motion and motion parameters at each point are recorded and can then be used for an exercise. Another way of teaching the system is to use a path that the therapist uses. The therapist may use a control to indicate a point to be taught or a continuous mode may be defined by which an entire trajectory is learned. Optionally the path and points are edited before replay. Optionally, the paths are abstracted, for example, by smoothing or identifying motion points, before playback.

n) Step Initiated. The patient initiates the motion (e.g., a 1 cm motion or 100 gram force) and device 600 completes or helps the patient complete the motion in space, however, patient initiated motion occurs in steps and/or increments. In some exemplary embodiments of the invention, a patient generated force in a predetermined "right" direction and/or range of directions must be applied at each step in order for device 600 to complete and/or help the patient complete the motion. A "right" direction is optionally defined as one in which the patient will receive a desired therapeutic benefit for moving in that direction. Optionally, the steps and/or increments are variable. Optionally, the steps and/or increments are pre-settable. Optionally, there is more than one "right" direction. The completion may be of a whole trajectory or of part of a trajectory.

o) Follow Assist. Device 600 is pre-programmed with at least one point in a path of motion to be followed by the patient. In an exemplary mode of operation, patient initiates motion along the path of motion, optionally assisted by device 600. Motion along the path is optionally conducted at a pre-set speed in some exemplary embodiments of the invention. Optionally, the speed is not pre-set. Upon the arrival of patient at the pre-programmed point, motion by the patient in a "right" direction causes at least a brief acceleration in speed instigated by device 600. Optionally, a plurality of points are used to allow the patient to "connect the dots" in the motion path. Optionally, "arrival at a point" is determined considering vector of approach, speed of approach, elapsed time prior to arrival, and/or accuracy of arrival to the point. Optionally, the patient must hold at the point steadily (i.e. no wobble) before being considered to have arrived at the point. In some exemplary embodiments of the invention, the patient is assisted with movement along a predetermined proper path for therapy. In some exemplary embodiments of the invention, device 600 moves continuously at a predetermined speed and whenever the patient exerts a force above a certain level and/or in the right direction), the speed of the exercise is increased.

General

While the above application has focused on motor training for rehabilitation, the methods and/or apparatus described herein may also be used for other applications. In an exemplary embodiment of the invention, motor training is used for enhancing the control of muscles by athletes. Alternatively or additionally, motor training is used for enhancing motor control of musicians. Optionally, musical feedback is provided during training and corresponding to the exercises. However, it should be noted that some methods of the present invention find particular utility in rehabilitation, especially when motor control is weak, patchy and/or non-existent.

Various designs for robots and positioning devices (e.g., hexapods) are known in the art. It should be appreciated that various ones of the statements described herein may be adapted for such robots and/or positioning devices, in accordance with exemplary embodiments of the invention. Alternatively or additionally, software may be provided for such robots and devices for carrying out various of the methods described herein, all in accordance with exemplary embodiments of the invention.

In some embodiments of the invention, the systems described herein are used for uses other than rehabilitation, for example, task training, testing and/or robotic manipulation.

It will be appreciated that the above described methods of rehabilitation may be varied in many ways, including, omitting or adding steps, changing the order of steps and the types of devices used. In addition, a multiplicity of various features, both of method and of devices have been described. In some embodiments mainly methods are described, however, also apparatus adapted for performing the methods are considered to be within the scope of the invention. It should be appreciated that different features may be combined in different ways. In particular, not all the features shown above in a particular embodiment are necessary in every similar embodiment of the invention. Further, combinations of the above features are also considered to be within the scope of some embodiments of the invention. Also within the scope of the invention are kits which include sets of a device, one or more limb holding attachments and/or software. Also, within the scope is hardware, software and computer readable-media including such software which is used for carrying out and/or guiding the steps described herein, such as control of arm position and providing feedback. Section headings are provided for assistance in navigation and should not be considered as necessarily limiting the contents of the section. When used in the following claims, the terms "comprises", "includes", "have" and their conjugates mean "including but not limited to". It should also be noted that the device is suitable for both male and female, with male pronouns sometimes being used for convenience.

It will be appreciated by a person skilled in the art that the present invention is not limited by what has thus far been described. Rather, the scope of the present invention is limited only by the following claims.

The invention claimed is:

1. A rehabilitation device, comprising:
a movement element capable of controlling at least one motion parameter of a portion of a patient;
a non-invasive brain monitor which generates a brain activity signal indicative of brain activity; and
circuitry of a controller including a memory having stored therein rehabilitation information and which inter-relates said brain activity signal and a mechanical movement signal, said mechanical movement signal derived by the controller and that is not based on the brain activity signal, to control said movement element as part of a rehabilitation process which utilizes said rehabilitation information and wherein said circuitry is adapted to change at least one motion parameter responsive to said brain activity signal.

2. A device according to claim 1, wherein said portion is a limb.

3. A device according to claim 1, wherein said circuitry controls at least one of the direction and location of a movement or a reach point.

4. A device according to claim 1, wherein said circuitry controls at least one of resistance to movement, speed and movement mode.

5. A device according to claim 1, wherein said circuitry measures at least one parameter of motion of said movement element.

6. A device according to claim 5, wherein said circuitry measures at least one of force, movement vector and speed of said movement.

7. A device according to claim 1, wherein said rehabilitation information comprises a rehabilitation plan.

8. A device according to claim 1, wherein said rehabilitation information comprises a rehabilitation diagnosis.

9. A device according to claim 1, wherein said rehabilitation information comprises at least one template of expected brain-motion relationship.

10. A device according to claim 1, wherein said circuitry is adapted to generate an expected motion based on said signal.

11. A device according to claim 1, wherein said circuitry is adapted to generate an expected brain activity based on movement of said movement element.

12. A device according to claim 1, wherein said circuitry is adapted to compare said signal to said rehabilitation information.

13. A device according to claim 1, wherein said circuitry is adapted to compare rehabilitation improvements of said patient to trends in said rehabilitation information.

14. A device according to claim 1, wherein said change is within a time frame of said movement.

15. A device according to claim 1, wherein said circuitry is adapted to detect an intent to move of said patient and provide control of said movement element in response thereto.

16. A device according to claim 1, wherein said circuitry is adapted to detect a readiness to move and provide control of said movement element in response thereto.

17. A device according to claim 1, wherein said circuitry is adapted to change a signal processing of said signal responsive to a detection of movement or lack thereof.

18. A device according to claim 1, wherein said brain monitor comprises an EEG monitor.

19. A device according to claim 1, wherein said brain monitor comprises a blood flow measuring device.

20. A device according to claim 1, wherein said brain monitor comprises an fMRI system.

21. A device according to claim 1, wherein said movement element comprises a robotic manipulator.

22. A device according to claim 1, wherein said movement element comprises a resistive movement element which resists motion in a controllable manner.

23. A device according to claim 1, wherein said movement element is adapted to be capable of substantially unrestricted movement in 3D space over a volume of at least 30 cm in minimum dimension.

24. A device according to claim 1, wherein said movement element is adapted to be selectively coupled and decoupled to at least one type of body portion.

25. A device according to claim 1, wherein said circuitry is adapted to provide cognitive rehabilitation to said patient.

26. A device according to claim 1, wherein said circuitry comprises a memory which stores a rehabilitation progress of said patient.

27. A device according to claim 1, comprising at least two movement elements which said circuitry is configured to identify as being associated with opposite limbs.

28. A device according to claim 1, wherein said at least one motion parameter is a rehabilitation parameter.

29. A method of rehabilitation, comprising:

controlling the motion of at least part of a patient as part of a rehabilitation process using a movement element;

measuring a first brain activity signal of said patient using a non-invasive first brain monitor, in association with said controlling;

deciding on a desired brain rehabilitation using circuitry of a controller including a memory having stored therein rehabilitation information and which inter-relates said brain activity signal and a mechanical movement signal, said mechanical movement signal derived by the controller and is not based on the brain activity signal, to control said movement element as part of a rehabilitation process which utilizes said rehabilitation information; and, changing said motion using said circuitry based on said measuring the brain activity signal to affect said rehabilitation.

30. A method according to claim 29, wherein said desired brain rehabilitation comprises cortical reorganization.

31. A method according to claim 29, comprising diagnosing the patient based on said measuring.

32. A method according to claim 31, wherein diagnosing comprises controlling said motion to achieve a plurality of desired motions for said diagnosis.

33. A method according to claim 31, wherein diagnosing comprises generating at least an indication of brain plasticity for said patient.

34. A method according to claim 29, comprising controlling said motion in response to said measuring.

35. A method according to claim 29, comprising controlling said measuring in response to said motion.

36. A method according to claim 29, comprising measuring the first brain activity of the patient during said motion.

37. A method according to claim 29, comprising repeating said controlling and said measuring for a same motion at least 10 times.

38. A method according to claim 29, comprising repeating said controlling and said measuring for at least 20 different motions in a same day of rehabilitation.

39. A method according to claim 29, comprising comparing brain activity signal measurements for a healthy side and a paretic side.

40. A method according to claim 29, comprising comparing movements for a healthy side and a paretic side.

41. A method according to claim 29, comprising measuring said motion.

42. A method according to claim 29, comprising measuring a quality of said motion.

43. A method according to claim 29, comprising tracking a progress of said rehabilitation process of said patient based on said measurements.

44. A method according to claim 29, comprising training a patient to control cortical activity using said controlling of motion as feedback.

45. A method of rehabilitation according to claim 29, wherein the measuring is of a patient locally activating a brain region; and, wherein deciding and changing are applied to said brain region in synchrony to said activating.

46. A method according to claim 45, wherein the rehabilitation process comprises physical rehabilitation which uses said brain region.

47. A method according to claim 45, wherein the rehabilitation process comprises delivering a drug.

48. A method according to claim 45, wherein the brain region is stimulated using an external means that directly stimulates brain tissue.

49. A method according to claim 45, wherein said locally activating comprises forcing a patient to locally activate a region using a physical exercise.

50. A method according to claim 45, wherein said locally activating comprises detecting local activation of said region.

51. A method of rehabilitation according to claim 29, further comprising:

causing the generation of brain activity by at least guiding a patient to at least intend to carry out a known physical activity;

measuring a second brain activity signal using a second brain monitor of a different type from the first brain monitor;

determining a correspondence between results of said first and said second brain activity signals measured;

performing rehabilitation on said patient using said second monitor; and assessing a brain activity of said patient during said performing utilizing a correspondence between said first and said second brain activity signals.

52. A method according to claim 51, wherein said assessing comprises assuming a fixed relationship between said results.

53. A method according to claim 51, wherein said generating brain activity comprises generating under computer control.

54. A method according to claim 51, wherein said generating brain activity comprises repeating a same at least intent to carry out a known physical activity at least 10 times.

55. A method according to claim 51, wherein measuring said second brain activity signal comprises electrical monitoring.

56. A method according to claim 51, wherein measuring said second brain activity signal is significantly lower cost than measuring said first brain activity signal.

57. A method according to claim 51, wherein measuring said first brain activity signal comprises fMRI.

* * * * *